United States Patent
Yokoyama et al.

(10) Patent No.: US 9,123,897 B2
(45) Date of Patent: Sep. 1, 2015

(54) BENZOTRIAZOLE DERIVATIVES AND ORGANIC ELECTROLUMINESCENT DEVICES USING THE DERIVATIVES

(71) Applicant: HODOGAYA CHEMICAL CO., LTD., Tokyo (JP)

(72) Inventors: Norimasa Yokoyama, Tokyo (JP); Shigetaka Numazawa, Ibaraki (JP); Shirou Irisa, Hyogo (JP); Shuichi Hayashi, Tokyo (JP)

(73) Assignee: HODOGAYA CHEMICAL CO., LTD., Tokyo (JP)

(*) Notice: Subject to any disclaimer, the term of this patent is extended or adjusted under 35 U.S.C. 154(b) by 0 days.

(21) Appl. No.: 14/345,513

(22) PCT Filed: Oct. 5, 2012

(86) PCT No.: PCT/JP2012/075994
§ 371 (c)(1),
(2) Date: Mar. 18, 2014

(87) PCT Pub. No.: WO2013/054764
PCT Pub. Date: Apr. 18, 2013

(65) Prior Publication Data
US 2014/0374721 A1    Dec. 25, 2014

(30) Foreign Application Priority Data

Oct. 14, 2011  (JP) ................. 2011-226501

(51) Int. Cl.
| | |
|---|---|
| *C07D 401/00* | (2006.01) |
| *H01L 51/00* | (2006.01) |
| *C07D 401/14* | (2006.01) |
| *C07D 401/10* | (2006.01) |
| *C07D 401/04* | (2006.01) |
| *H01L 51/50* | (2006.01) |

(52) U.S. Cl.
CPC .......... *H01L 51/0058* (2013.01); *C07D 401/04* (2013.01); *C07D 401/10* (2013.01); *C07D 401/14* (2013.01); *H01L 51/0052* (2013.01); *H01L 51/0067* (2013.01); *H01L 51/0072* (2013.01); *H01L 51/5012* (2013.01)

(58) Field of Classification Search
None
See application file for complete search history.

(56) References Cited

U.S. PATENT DOCUMENTS

| | | |
|---|---|---|
| 5,869,199 A | 2/1999 | Kido |
| 6,878,469 B2 | 4/2005 | Yoon et al. |
| 2008/0027226 A1 | 1/2008 | Rogers et al. |
| 2012/0012831 A1* | 1/2012 | Yokoyama et al. ............. 257/40 |
| 2013/0328040 A1 | 12/2013 | Yokoyama et al. |
| 2014/0124756 A1 | 5/2014 | Yokoyama et al. |

FOREIGN PATENT DOCUMENTS

| | | |
|---|---|---|
| GB | 2480813 | 12/2011 |
| JP | 2734341 | 1/1998 |
| WO | 03/060956 | 7/2003 |
| WO | 2005/054212 | 6/2005 |
| WO | 2010/107074 | 9/2010 |

OTHER PUBLICATIONS

CAPLUS 2011:1571990.*
U.S. Appl. No. 14/349,438 to Norimasa Yokoyama et al., filed Apr. 3, 2014.
International Search Report Issued in PCT/JP2012/075994 on Nov. 6, 2012.

* cited by examiner

*Primary Examiner* — Heidi Reese
(74) *Attorney, Agent, or Firm* — Greenblum & Bernstein, P.L.C.

(57) ABSTRACT

Benzotriazole derivatives represented by the following general formula (1),

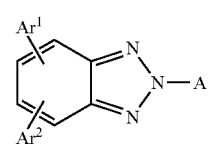

(1)

wherein $Ar^1$ and $Ar^2$ are, for example, aromatic hydrocarbon groups or aromatic heterocyclic ring groups, and A is a group including a pyridine ring. The compounds excel in electron injection/transport capability, feature a high hole-blocking power and a high stability in their thin-film form, and are useful as materials for producing highly efficient and highly durable organic electroluminescent devices.

12 Claims, 21 Drawing Sheets

8: CATHODE
7: ELECTRON INJECTION LAYER
6: ELECTRON-TRANSPORTING LAYER
5: HOLE-BLOCKING LAYER
4: LUMINOUS LAYER
3: HOLE - TRANSPORTING LAYER
2: TRANSPARENT ANODE
1: GLASS SUBSTRATE

BENZOTRIAZOLE DERIVATIVES AND ORGANIC ELECTROLUMINESCENT DEVICES USING THE DERIVATIVES

FIELD OF THE INVENTION

This invention relates to novel benzotriazole derivatives. More specifically, the invention relates to novel benzotriazole derivatives into which a pyridine ring structure has been introduced and to organic electroluminescent devices that have an organic layer containing the above derivatives between the electrodes.

BACKGROUND ART

An organic electroluminescent device (hereinafter often called organic EL device) is a spontaneously luminous device which features higher brightness and higher legibility than those of the liquid crystal devices enabling vivid display to be attained and has, therefore, been vigorously studied.

In 1987, C. W. Tang et al. of the Eastman Kodak Co. have developed a device of a layer-laminated structure comprising various kinds of materials to bear individual roles, and have put an organic EL device using organic materials into a practical use. The above organic EL device is constituted by laminating layers of a fluorescent body capable of transporting electrons and an organic material capable of transporting holes. Upon injecting both electric charges into the layer of the fluorescent body to emit light, the device is capable of attaining a brightness of as high as 1000 cd/m$^2$ or more with a voltage of not higher than 10 V.

So far, very many improvements have been made to put the organic EL device to practical use. For example, the organic EL device has been widely known having a structure comprising an anode, a hole injection layer, a hole-transporting layer, a luminous layer, an electron-transporting layer, an electron injection layer and a cathode which are arranged in this order on a substrate more finely dividing their roles than ever before. The device of this kind is achieving a high efficiency and a high durability.

To further improve the luminous efficiency, attempts have been made to utilize triplet excitons and study has been forwarded to utilize a phosphorescent luminous compound.

In the organic EL device, the electric charges injected from the two electrodes recombine together in the luminous layer to emit light. Here, however, the hole migration rate is higher than the electron migration rate arousing a problem of a decrease in the efficiency since the holes partly pass through the luminous layer. Therefore, it has been desired to provide an electron-transporting material that has a higher electron migration rate.

Tris(8-hydroxyquinoline)aluminum (hereinafter abbreviated as Alq$_3$) which is a representative luminous material has also been generally used as an electron-transporting material having, however, a low electron mobility and a work function of 5.6 eV and, therefore, having a hole-locking capability which is far from satisfactory.

A method of inserting a hole-blocking layer is one of the measures for preventing the holes from partly passing through the luminous layer to improve the probability of recombination of the electric charge in the luminous layer.

As a hole-blocking material used for forming the hole-blocking layer, for example, a patent document 1 discloses a 3-(4-biphenylyl)-4-phenyl-5-(4-t-butylphenyl)-1,2,4-triazole (hereinafter abbreviated as TAZ).

As the hole-blocking material, there have, further, been known a bathocuproin (hereinafter abbreviated as BCP) and a mixed ligand complex of aluminum such as aluminum (III) bis(2-methyl-8-quinolinato)-4-phenyl phenolate (hereinafter abbreviated as BAlq).

The TAZ has a work function of as large as 6.6 eV and a large hole-blocking power, and is used for forming an electron-transporting hole-blocking layer that is laminated on the cathode side of a fluorescent luminous layer or a phosphorescent luminous layer prepared by vacuum evaporation or by coating and, therefore, contributes to improving the efficiency of the organic EL devices.

Because of its low electron-transporting capability, however, the TAZ had to be used in combination with an electron-transporting material having a higher electron-transporting capability. The BCP, on the other hand, has a work function of as large as 6.7 eV and a large hole-blocking power but a glass transition point (Tg) of as low as 83° C. In the form of a thin film, therefore, the BCP lacks stability and still leaves much room for improvement for forming a hole-blocking layer that works maintaining stability.

A patent document 2 discloses a general electron-transporting compound which, however, still lacks stability when it is formed into a film or lacks the function for blocking the holes to a sufficient degree.

In order to improve characteristics of the organic electroluminescent devices, therefore, it has been desired to provide an organic compound that excels in electron injection/transport capability and in hole-blocking power, and features high stability in the form of a thin film.

PRIOR ART DOCUMENTS

Patent document 1: Japanese Patent No. 2734341
Patent document 2: WO2003/060956

OUTLINE OF THE INVENTION

Problems that the Invention is to Solve

The object of the present invention is to provide a novel organic compound that excels in electron injection/transport capability, features a high hole-blocking power and a high stability in the form of a thin film, and can be used as a material for producing highly efficient and highly durable organic electroluminescent devices.

Another object of the invention is to provide a highly efficient and highly durable organic electroluminescent device having an organic layer that is formed by using the above organic compound.

Means for Solving the Problems

To achieve the above objects, the present inventors have paid attention to that a nitrogen atom of a pyridine ring having affinity to electron has a capability of being coordinated on a metal, that a benzotriazole ring structure has a high electron transport capability, that the pyridine ring and the benzotriazole ring structure have resistance against the heat, and have designed and chemically synthesized a compound that has the benzotriazole ring structure and the pyridine ring structure, have prepared various organic electroluminescent devices by using the above compound on an experimental basis, have keenly evaluated the properties of the device and, as a result, have confirmed that a high efficiency and a high durability can be obtained and have thus completed the present invention.

According to the present invention, there are provided benzotriazole derivatives represented by the following general formula (1),

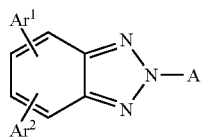

(1)

wherein,
Ar¹ is an aromatic hydrocarbon group or an aromatic heterocyclic group,
Ar² is a hydrogen atom, a deuterium atom, an aromatic hydrocarbon group or an aromatic heterocyclic group, and
A is a monovalent group represented by the following formula (2),

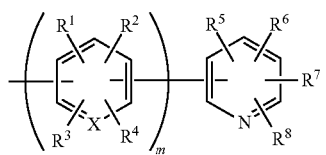

(2)

wherein,
m is an integer of 0, 1 or 2,
X is a carbon atom or a nitrogen atom,
$R^1$ to $R^8$ are, respectively, hydrogen atoms, deuterium atoms, fluorine atoms, chlorine atoms, cyano groups, alkyl groups having 1 to 6 carbon atoms, aromatic hydrocarbon groups or aromatic heterocyclic groups, when X is a nitrogen atom, none of the groups $R^1$ to $R^4$ are bonded to the nitrogen atom, and any one of $R^1$ to $R^4$ is not present, and
when m is 2, a plurality of $R^1$ to $R^4$ and X may be the same or different from each other.

According to the present invention, further, there is provided an organic electroluminescent device having a pair of electrodes and at least one organic layer interposed therebetween, wherein at least one of the organic layers contains the benzotriazole derivative.

In the organic EL device of the invention, the organic layer containing the benzotriazole derivative is, for example, an electron-transporting layer, a hole-blocking layer, a luminous layer or an electron injection layer.

Effects of the Invention

The benzotriazole derivative of the invention represented by the above general formula (1) is a novel compound and has a benzotriazole ring and a pyridine ring. The benzotriazole derivative having the above structure features the following properties.
(A) The electrons can be favorably injected.
(B) The electrons migrate at a high rate.
(C) The holes can be blocked favorably.
(D) Remains stable in a thin-film state.
(E) Excellent heat resistance.
Owing to its stability in the thin-film state, the benzotriazole derivative of the present invention can be used as an organic layer that is provided between the electrodes of an organic electroluminescent device, and imparts the following properties to the organic EL device.
(F) A high luminous efficiency and a high power efficiency.
(G) A low luminescence start voltage.
(H) A low practical driving voltage.
(I) A long service life of the device (large durability).

For instance, the organic EL device forming the electron injection layer and/or the electron-transporting layer by using the benzotriazole derivative of the invention, features a high electron injection/migration rate, an improved electron transport efficiency from the electron-transporting layer into the luminous layer and, therefore, features a high luminous efficiency, a low driving voltage and a large durability.

Further, the organic EL device having a hole-blocking layer formed by using the benzotriazole derivative of the invention features excellent hole-blocking power and electron transport capability and, therefore, requires a decreased driving voltage yet maintaining a high luminous efficiency and, besides, features an improved resistance against the electric current and an improved maximum brightness.

Further, the benzotriazole derivative of the invention features excellent electron transport capability and a wide band gap and can, therefore, be used as a host material for the luminous layer. By using the benzotriazole derivative of the invention as a luminous layer which, further, carries a fluorescent material or a luminous phosphor called dopant thereon, it is made possible to lower the driving voltage of the organic EL device and to improve the luminous efficiency.

As described above, the benzotriazole derivative of the present invention is useful as a material for constituting the electron injection layer, electron-transporting layer, hole-blocking layer or luminous layer of the organic EL device, works to improve the luminous efficiency and the power efficiency of the organic EL device, to lower the practical driving voltage, to realize a low luminescence start voltage and to increase the durability.

MODES FOR CARRYING OUT THE INVENTION

Figure 1:
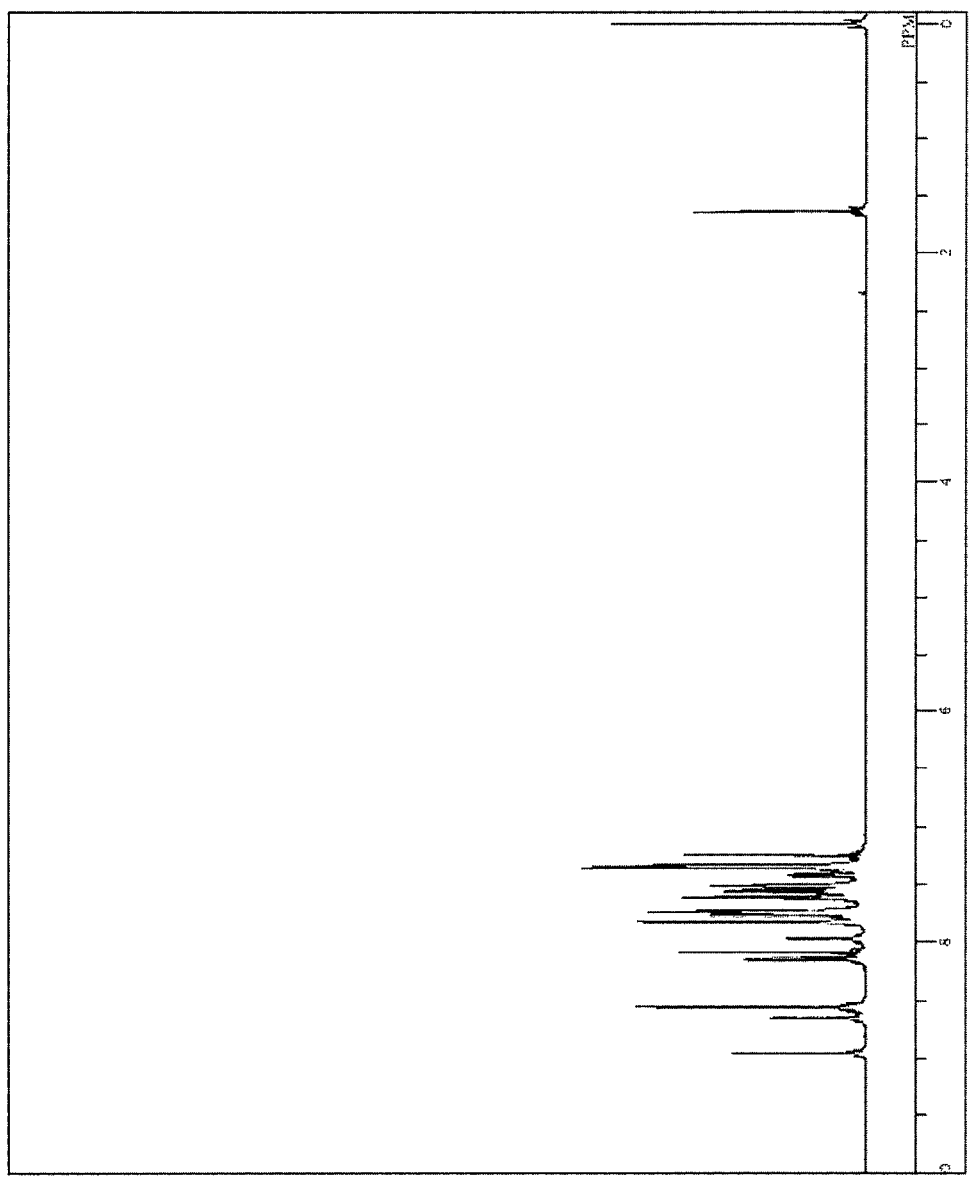
FIG. 1 is a ¹H-NMR chart of a compound (compound 4) of Example 1.

The novel benzotriazole derivative of the present invention is represented by the following formula (1) and has a structure in which a group A having a pyridine ring is bonded to a benzotriazole ring,

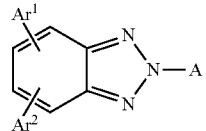

(1)

In the above general formula (1), $Ar^1$ is an aromatic hydrocarbon group or an aromatic heterocyclic group, and $Ar^2$ is a deuterium atom, an aromatic hydrocarbon group or an aromatic heterocyclic group.

The aromatic hydrocarbon group and the aromatic heterocyclic group in $Ar^1$ and $Ar^2$ may have a monocyclic structure or a condensed polycyclic structure.

Examples of these aromatic groups include phenyl group, biphenylyl group, terphenylyl group, tetrakisphenyl group, styryl group, naphthyl group, anthryl group, acenaphthenyl group, phenanthryl group, fluorenyl group, indenyl group, pyrenyl group, triazyl group, pyrimidyl group, furanyl group, pyrolyl group, thienyl group, quinolyl group, isoquinolyl group, benzofuranyl group, benzothienyl group, indolyl group, carbazolyl group, benzooxazolyl group, benzothiazolyl group, quinoxalyl group, benzoimidazolyl group, pyrazolyl group, dibenzofuranyl group, dibenzothienyl group, naphthyridinyl group, phenanthrolinyl group and acridinyl group.

Among these aromatic heterocyclic groups, preferred are sulfur-containing aromatic heterocyclic groups such as thienyl group, benzothienyl group, benzothiazolyl group and dibenzothienyl group. However, nitrogen-containing aromatic heterocyclic groups and, specifically, such groups as pyridyl group and the like groups are not desired from the standpoint of bipolar property.

The above aromatic groups (aromatic hydrocarbon groups and aromatic heterocyclic groups) may have a substituent.

As the substituent, there can be exemplified deuterium atom; fluorine atom; chlorine atom; cyano group; hydroxyl group; nitro group; straight-chain or branched alkyl group having 1 to 6 carbon atoms; cyclic alkyl group (e.g., cyclopentyl group, cyclohexyl group); straight-chain or branched alkoxy group having 1 to 6 carbon atoms; dialkylamino group substituted with a straight-chain or branched alkyl group having 1 to 6 carbon atoms; aryl groups such as phenyl group, naphthyl group, anthryl group, fluorenyl group and styryl group; and aromatic heterocyclic groups such as pyridyl group, pyridoindolyl group, quinolyl group and benzothiazolyl group. These substituents may, further, have a substituent like trifluoromethyl group.

Examples of the alkyl group portion of the alkyl group and the alkoxy group in the above-mentioned substituents may be the same as those exemplified for the alkyl groups represented by $R^1$ to $R^8$ in the general formula (2) that will be described below.

In the above general formula (1), the monovalent group A has a pyridine ring, and is represented by the following formula (2),

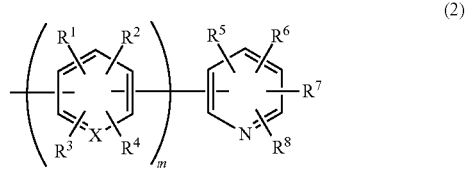

(2)

In the above formula (2), m is an integer of 0, 1 or 2. Further, X in the ring is a carbon atom or a nitrogen atom. $R^1$ to $R^8$ are, respectively, hydrogen atoms, deuterium atoms, fluorine atoms, chlorine atoms, cyano groups, alkyl groups having 1 to 6 carbon atoms, aromatic hydrocarbon groups or aromatic heterocyclic groups.

There is no specific limitation on the alkyl group so far as it has carbon atoms in a number in a range of 1 to 6; i.e., the alkyl group may have a straight-chain or branched structure, and may be methyl group, ethyl group, n-propyl group, i-propyl group, n-butyl group, 2-methylpropyl group, t-butyl group, n-pentyl group, 3-methylbutyl group, t-pentyl group, n-hexyl group, i-hexyl group or t-hexyl group. The alkyl group, too, may have a substituent. As the substituent, there can be exemplified deuterium atom; fluorine atom; chlorine atom; cyano group; aryl groups such as phenyl group, naphthyl group, anthrilyl group, fluorenyl group and stylyl group; and aromatic heterocyclic groups such as pyridyl group, pyridoindolyl group, quinolyl group and benzothiazolyl group. A representative example of the substituted alkyl group is a trifluoromethyl group.

The above aromatic hydrocarbon groups and aromatic heterocyclic groups may be the same groups as those exemplified for the groups $Ar^1$ and $Ar^2$. Further, these aromatic groups may have substituents and, besides, the kinds of the substituents may be the same as those exemplified for the groups $Ar^1$ and $Ar^2$.

In the above formula (2), when X is a nitrogen atom (i.e., when the ring that includes X is a pyridine ring), none of the groups $R^1$ to $R^4$ are bonded to the nitrogen atom, and any one of $R^1$ to $R^4$ is not present.

When m is 2, further, a plurality of $R^1$, $R^2$, $R^3$ or $R^4$ may be the same or different from each other. Further, a plurality of X may be different from each other. For instance, the benzene ring (X=C) and the pyridine ring (X=N) may be bonded in a form of being mixed together to the pyridine ring at a terminal.

The benzotriazole derivative of the invention represented by the above general formula (1) is synthesized, for example, by a method described below.

First, a 2-aminoarylazobenzene derivative including a pyridyl group that has the groups $R^5$ to $R^8$ in the general formula (2) is synthesized from a 1,2-diaminobenzene derivative and a nitroarylpyridine derivative according to a known method.

The 2-aminoarylazobenzene derivative is subjected to an oxidative cyclization reaction with an iodobenzenediacetate to synthesize a 2-arylbenzotriazole derivative having the above pyridyl group as a substituent (e.g., see Aust. J. Chem., 45, 371 (1992)).

The thus obtained 2-arylbenzotriazole derivative and various arylboron acid derivatives are subjected to a cross-coupling reaction such as Suzuki coupling to synthesize the benzotriazole derivative of the present invention represented by the general formula (1).

The obtained compound is refined by a column chromatography, by an adsorption refining using silica gel, activated carbon or activated clay, by a recrystallization method using a solvent or by a crystallization method. The compound is identified by the NMR analysis.

In the benzotriazole derivative of the invention, X in the group represented by the above formula (2) is desirably a carbon atom. The benzotriazole derivative, in this case, is represented by the following general formula (1-1),

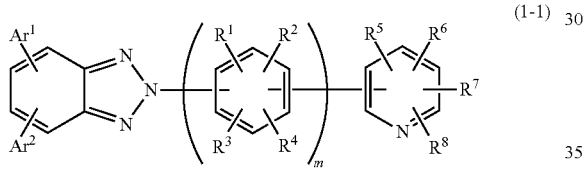

(1-1)

wherein,
$Ar^1, Ar^2, R^1$ to $R^8$ and m are as defined in the above general formula (1).

In the benzotriazole derivative represented by the above general formula (1-1), further, m is desirably 1. The benzotriazole derivative, in this case, is represented by the following general formula (1a),

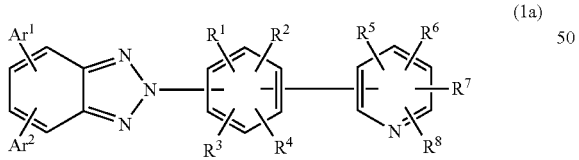

(1a)

wherein,
$Ar^1, Ar^2, R^1$ to $R^8$ and m are as defined in the above general formula (1).

Further, the benzotriazole derivatives represented by the above general formula (1a) can be classified into the compounds represented, for example, by the following general formulas (1a-1) to (1a-4) depending upon the coupling position of the benzene ring that is interposed between the benzotriazole ring and the pyridine ring.

Benzotriazole Derivative of the General Formula (1a-1):

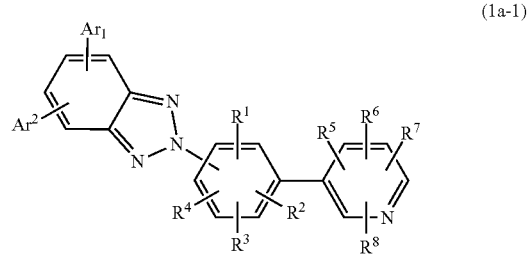

(1a-1)

wherein,
$Ar^1, Ar^2, R^1$ to $R^8$ and m are as defined in the above general formula (1).

Benzotriazole Derivative of the General Formula (1a-2):

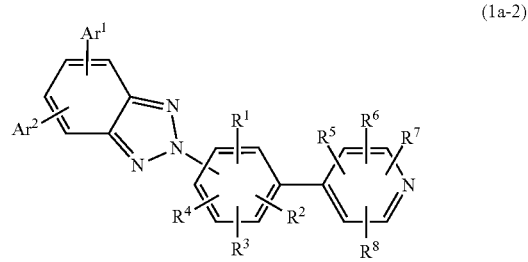

(1a-2)

wherein,
$Ar^1, Ar^2, R^1$ to $R^8$ and m are as defined in the above general formula (1).

Benzotriazole Derivative of the General Formula (1a-3):

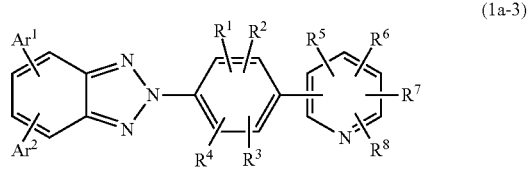

(1a-3)

wherein,
$Ar^1, Ar^2, R^1$ to $R^8$ and m are as defined in the above general formula (1).

Benzotriazole Derivative of the General Formula (1a-4):

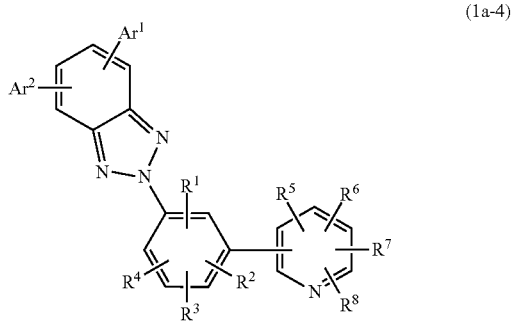

(1a-4)

wherein,

Ar$^1$, Ar$^2$, R$^1$ to R$^8$ and m are as defined in the above general formula (1).

Described below are concrete examples of the benzotriazole derivative of the present invention to which only, however, the invention is in no way limited.

In the compounds concretely exemplified below, there are shown the values of m and the kinds of X in the general formula (2) that represents the group A. Further, specifically preferred compounds are attached with the numbers of the corresponding formulas (1a-1) to (1a-4). In the following compounds, the compound numbers 1 and 2 are not listed.

(Compound 3)

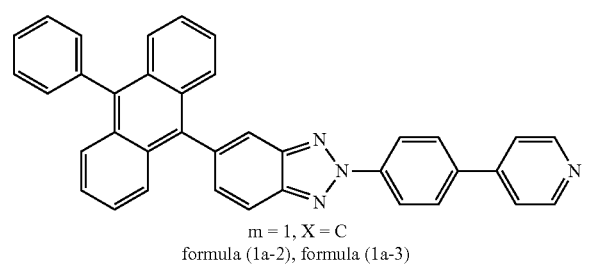

m = 1, X = C
formula (1a-2), formula (1a-3)

(Compound 4)

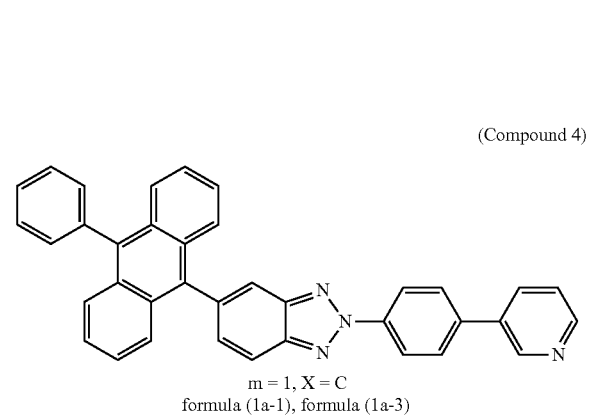

m = 1, X = C
formula (1a-1), formula (1a-3)

(Compound 5)

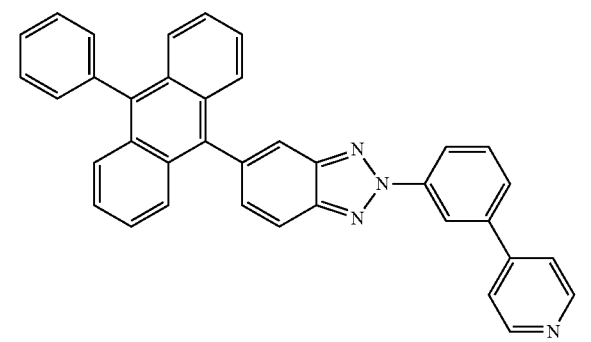

m = 1, X = C
formula (1a-2), formula (1a-4)

(Compound 6)

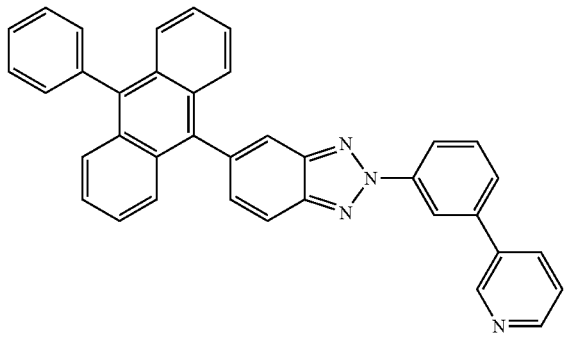

m = 1, X = C
formula (1a-1), formula (1a-4)

(Compound 7)

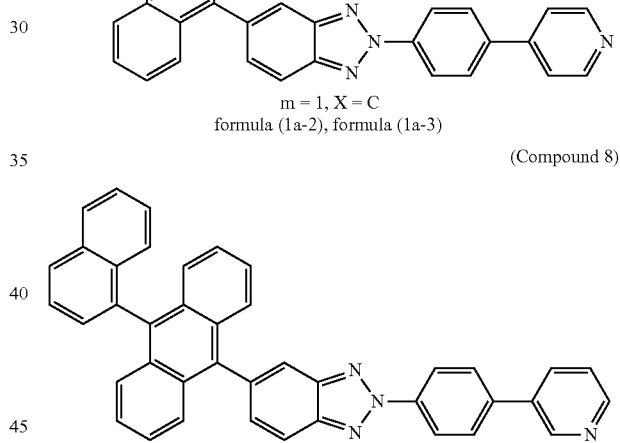

m = 1, X = C
formula (1a-2), formula (1a-3)

(Compound 8)

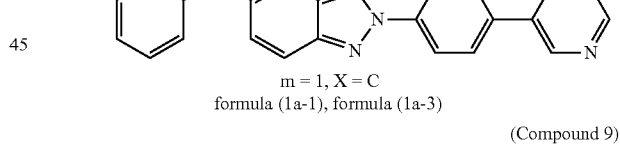

m = 1, X = C
formula (1a-1), formula (1a-3)

(Compound 9)

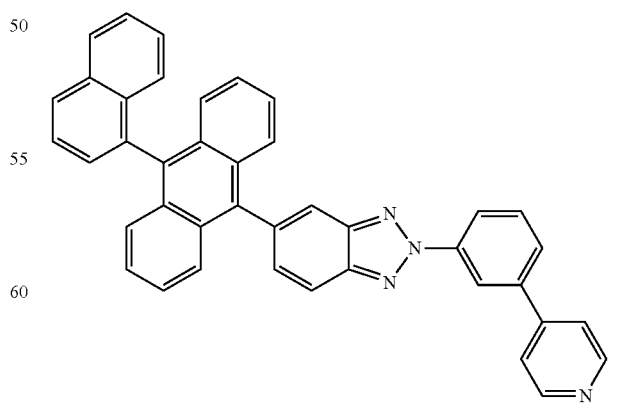

m = 1, X = C
formula (1a-2), formula (1a-4)

(Compound 10)
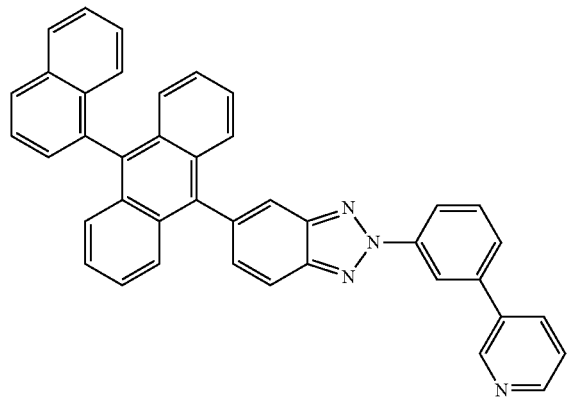
m = 1, X = C
formula (1a-2), formula (1a-4)
(Compound 11)
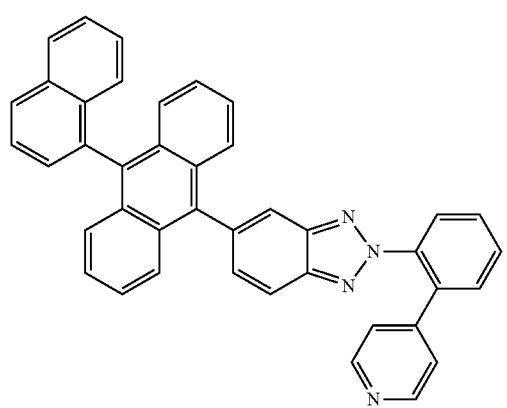
m = 1, X = C
formula (1a-1)
(Compound 12)
m = 1, X = C
formula (1a-2)
(Compound 13)
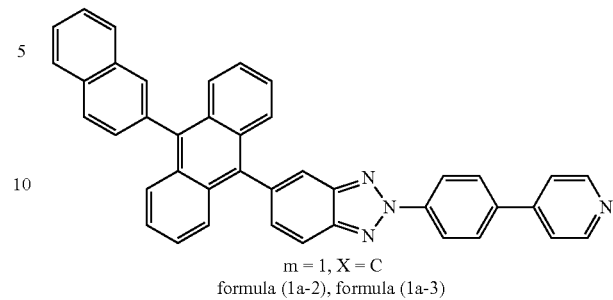
m = 1, X = C
formula (1a-2), formula (1a-3)
(Compound 14)
m = 1, X = C
formula (1a-1), formula (1a-3)
(Compound 15)
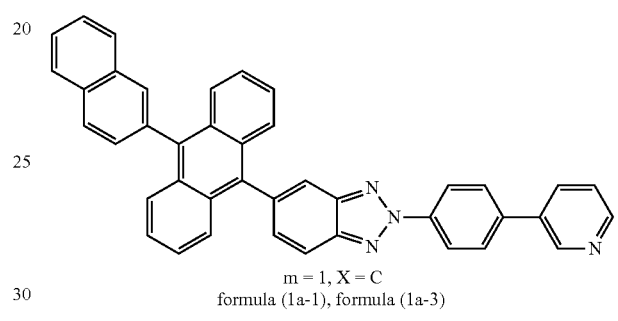
m = 1, X = C
formula (1a-1), formula (1a-4)
(Compound 16)
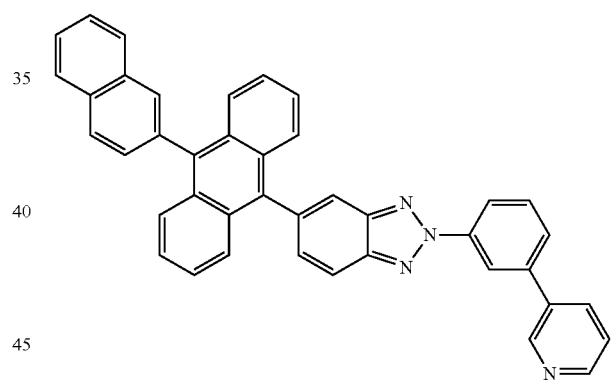
m = 1, X = C
formula (1a-2), formula (1a-4)

(Compound 17)
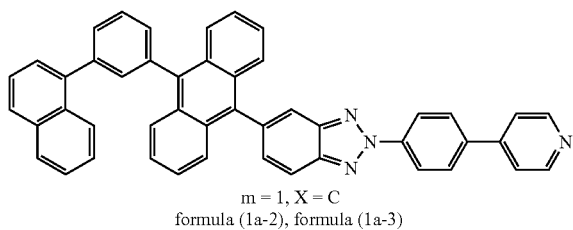
m = 1, X = C
formula (1a-2), formula (1a-3)
(Compound 18)
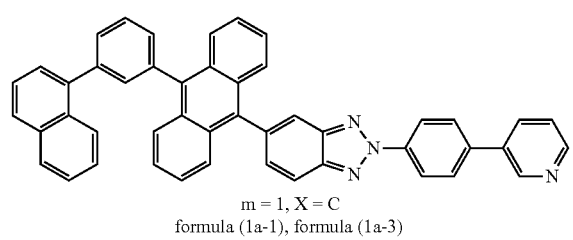
m = 1, X = C
formula (1a-1), formula (1a-3)
(Compound 19)
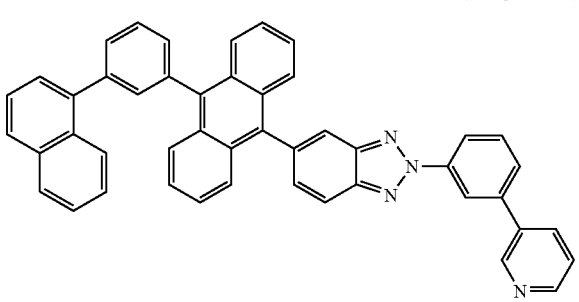
m = 1, X = C
formula (1a-1), formula (1a-4)
(Compound 20)
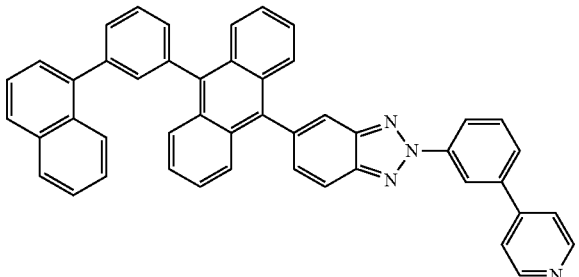
m = 1, X = C
formula (1a-2), formula (1a-4)
(Compound 21)
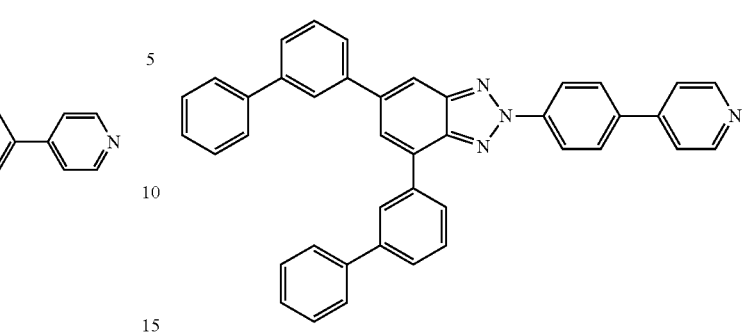
m = 1, X = C
formula (1a-2), formula (1a-3)
(Compound 22)
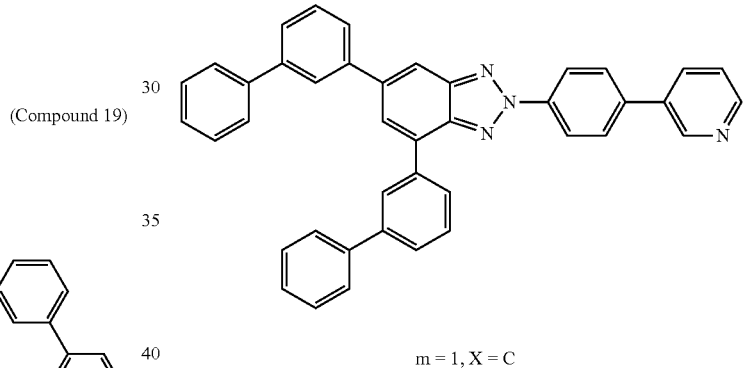
m = 1, X = C
formula (1a-1), formula (1a-3)
(Compound 23)
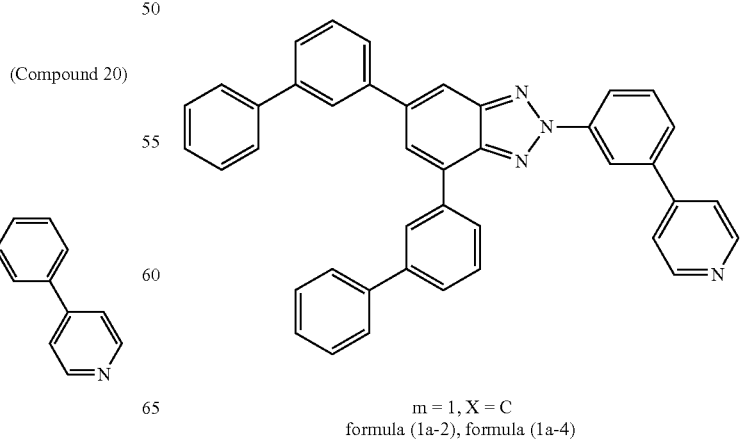
m = 1, X = C
formula (1a-2), formula (1a-4)

(Compound 24)
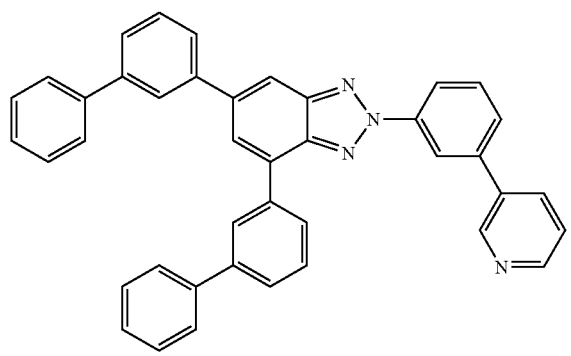
m = 1, X = C
formula (1a-1), formula (1a-4)
(Compound 25)
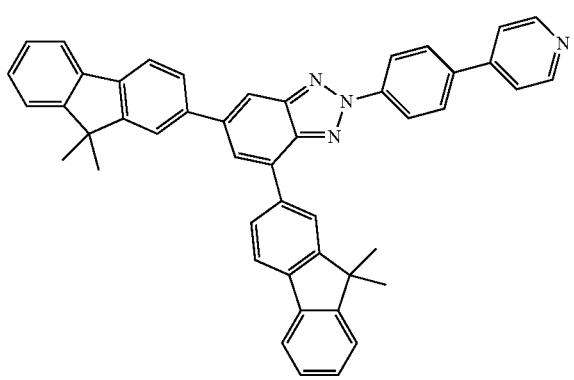
m = 1, X = C
formula (1a-2), formula (1a-3)
(Compound 26)
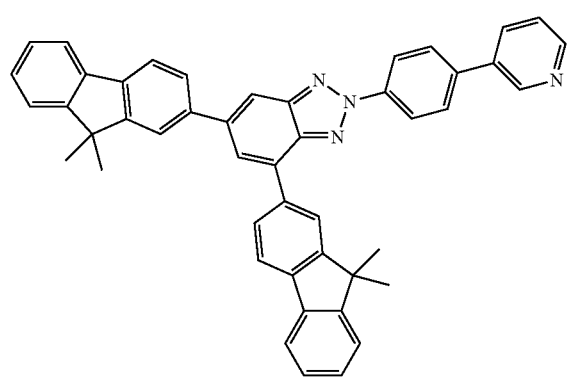
m = 1, X = C
formula (1a-1), formula (1a-3)
(Compound 27)
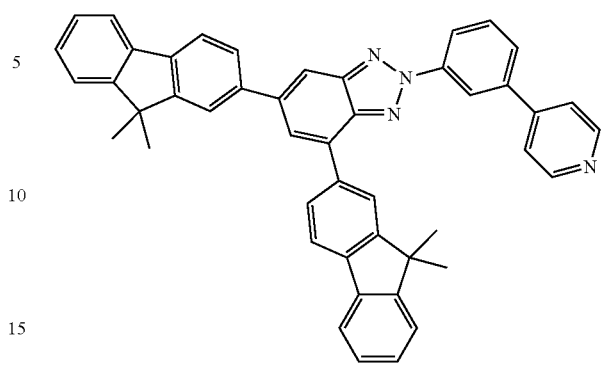
m = 1, X = C
formula (1a-2), formula (1a-4)
(Compound 28)
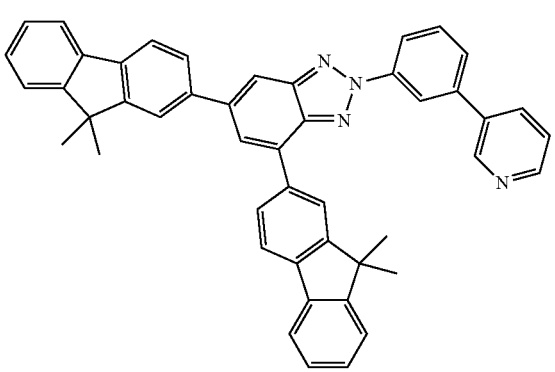
m = 1, X = C
formula (1a-1), formula (1a-4)
(Compound 29)
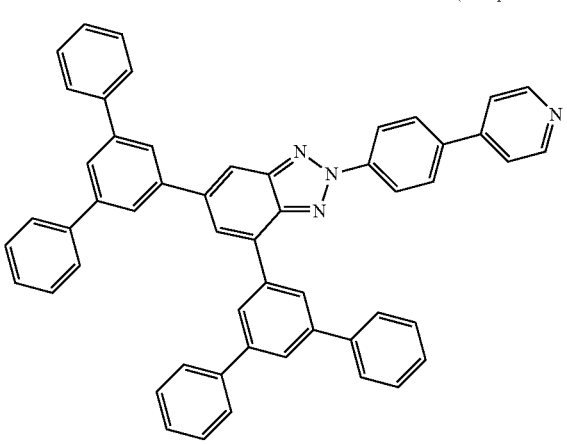
m = 1, X = C
formula (1a-2), formula (1a-3)

(Compound 30)
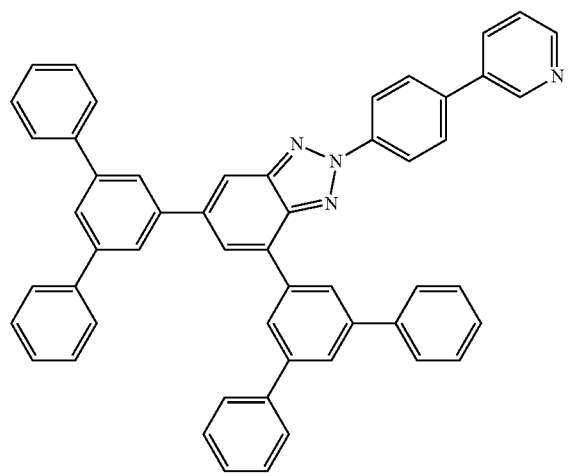
m = 1, X = C
formula (1a-1), formula (1a-3)
(Compound 31)
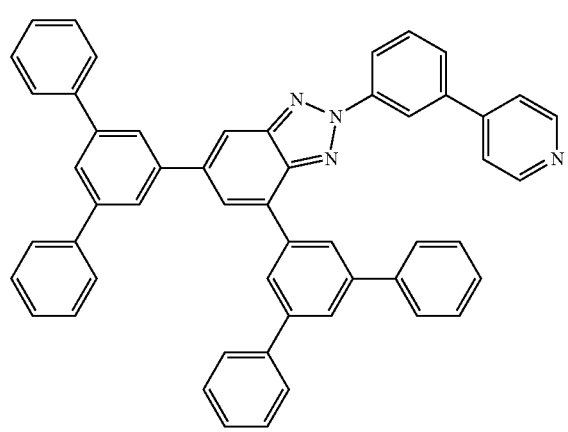
m = 1, X = C
formula (1a-2), formula (1a-4)
(Compound 32)
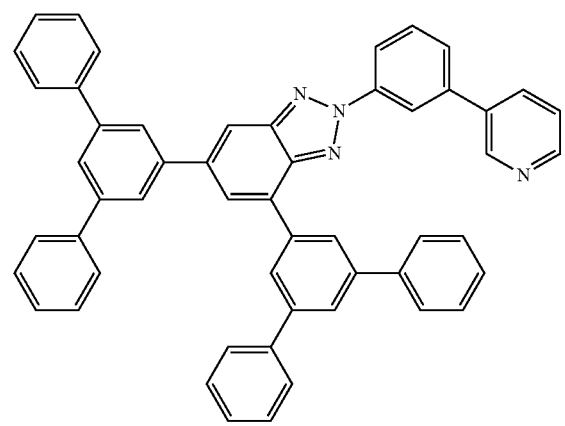
m = 1, X = C
formula (1a-1), formula (1a-4)
(Compound 33)
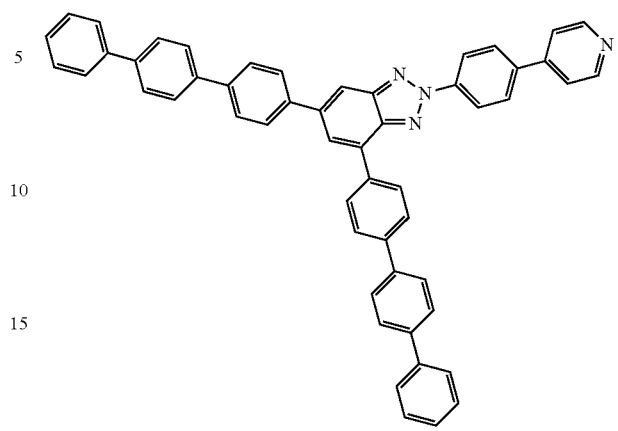
m = 1, X = C
formula (1a-2), formula (1a-3)
(Compound 34)
m = 1, X = C
formula (1a-1), formula (1a-3)
(Compound 35)
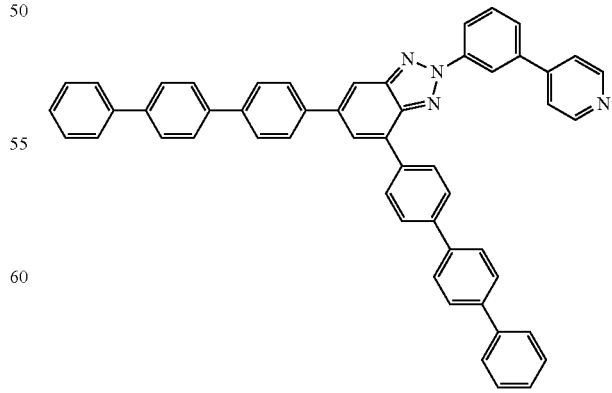
m = 1, X = C
formula (1a-2), formula (1a-4)

(Compound 36)
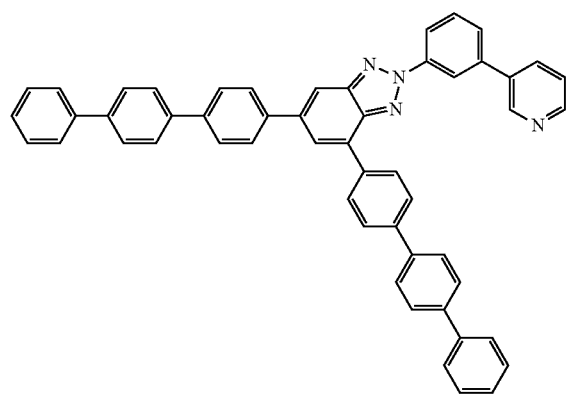
m = 1, X = C
formula (1a-1), formula (1a-4)
(Compound 37)
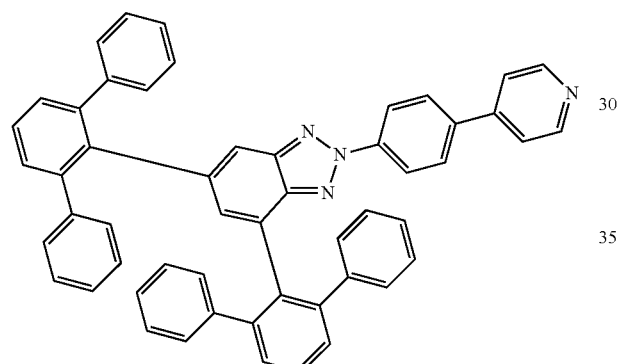
m = 1, X = C
formula (1a-2), formula (1a-3)
(Compound 38)
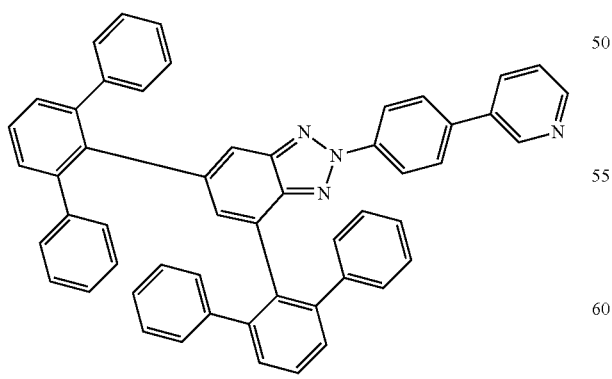
m = 1, X = C
formula (1a-1), formula (1a-3)
(Compound 39)
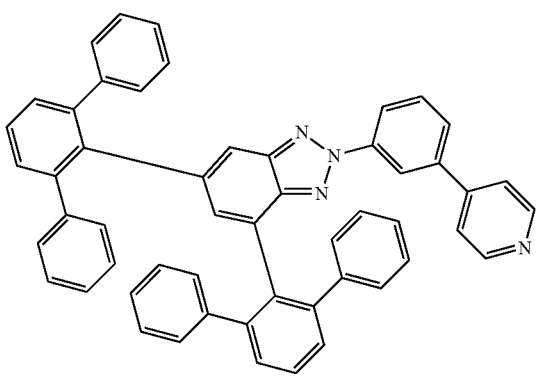
m = 1, X = C
formula (1a-2), formula (1a-4)
(Compound 40)
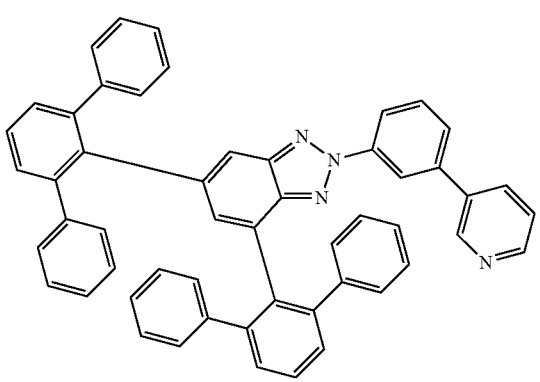
m = 1, X = C
formula (1a-1), formula (1a-4)
(Compound 41)
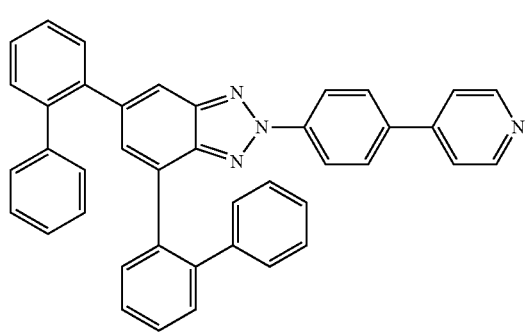
m = 1, X = C
formula (1a-2), formula (1a-3)

(Compound 42)
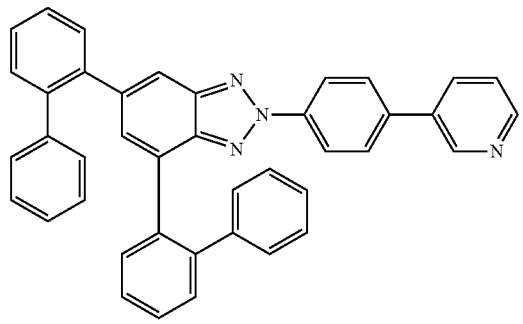
m = 1, X = C
formula (1a-1), formula (1a-3)
(Compound 43)
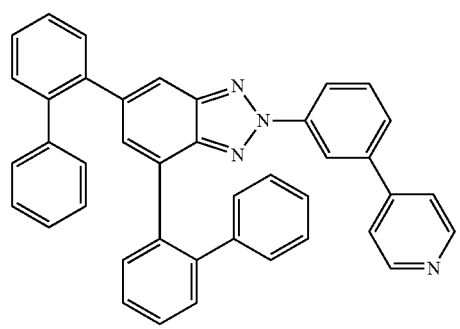
m = 1, X = C
formula (1a-2), formula (1a-4)
(Compound 44)
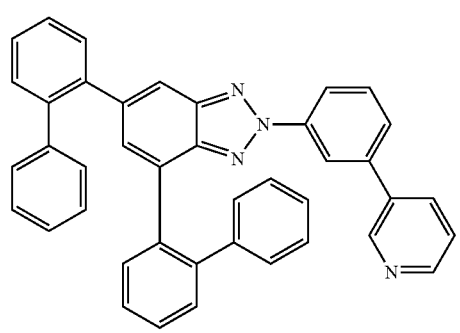
m = 1, X = C
formula (1a-1), formula (1a-4)
(Compound 45)
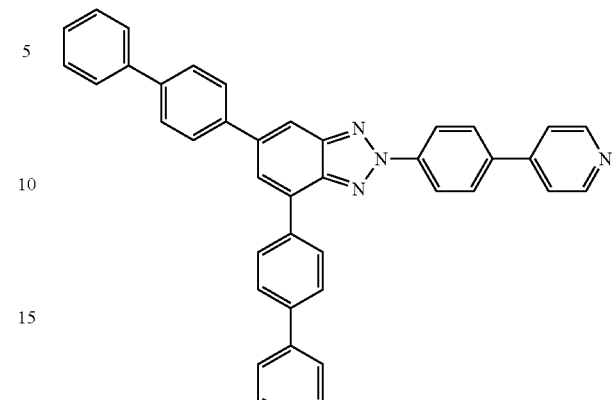
m = 1, X = C
formula (1a-2), formula (1a-3)
(Compound 46)
m = 1, X = C
formula (1a-1), formula (1a-3)
(Compound 47)
m = 1, X = C
formula (1a-2), formula (1a-4)

(Compound 48)
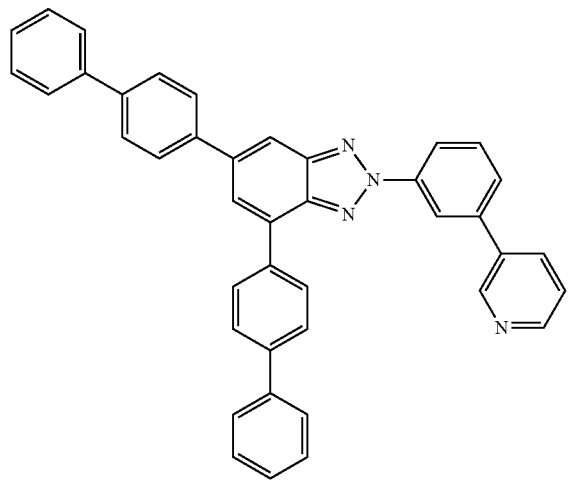
m = 1, X = C
formula (1a-1), formula (1a-4)
(Compound 49)
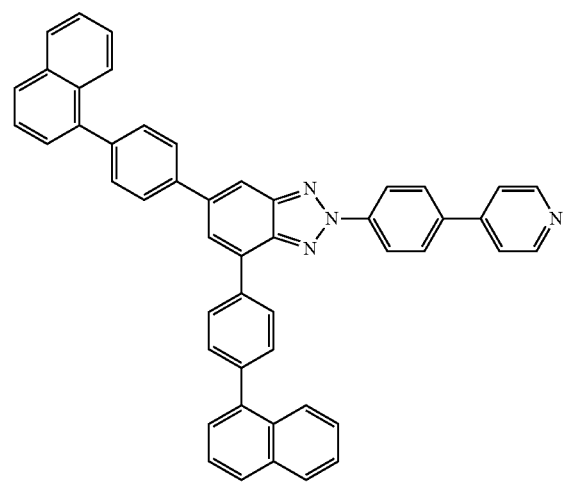
m = 1, X = C
formula (1a-2), formula (1a-3)
(Compound 50)
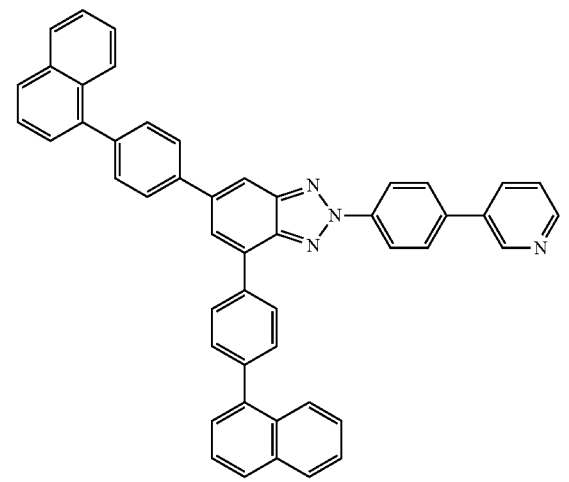
m = 1, X = C
formula (1a-1), formula (1a-3)
(Compound 51)
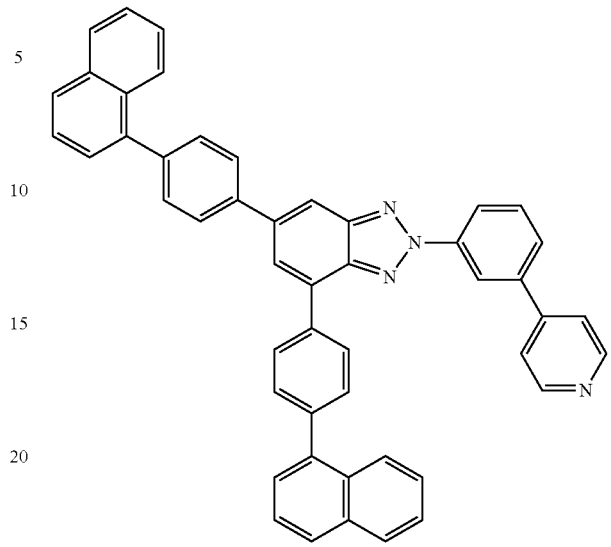
m = 1, X = C
formula (1a-2), formula (1a-4)
(Compound 52)
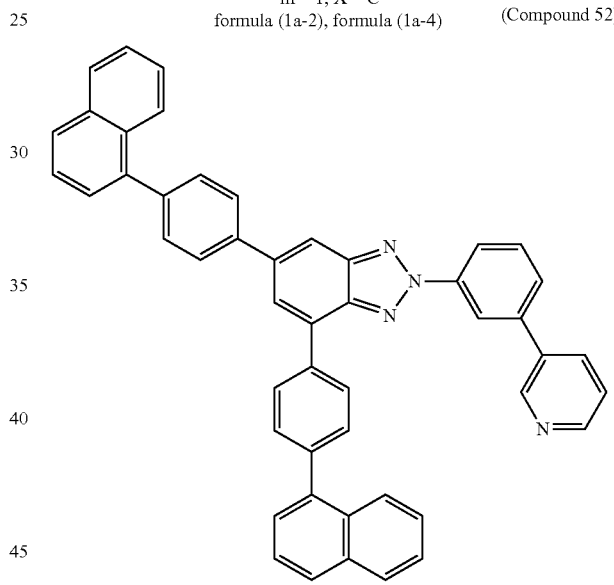
m = 1, X = C
formula (1a-1), formula (1a-4)
(Compound 53)
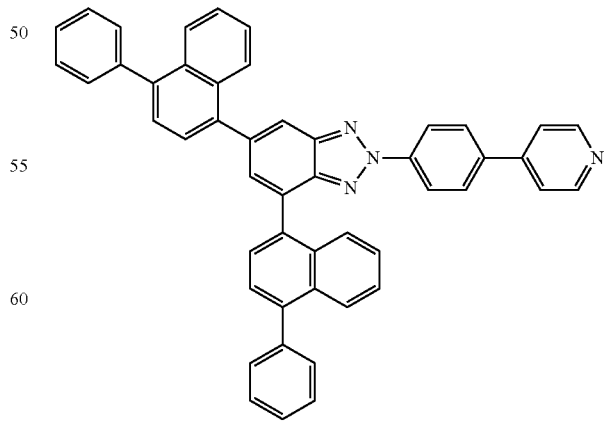
m = 1, X = C
formula (1a-2), formula (1a-3)

(Compound 54)
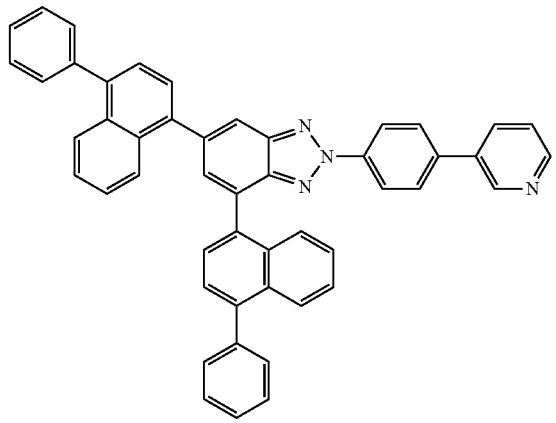
m = 1, X = C
formula (1a-1), formula (1a-3)
(Compound 55)
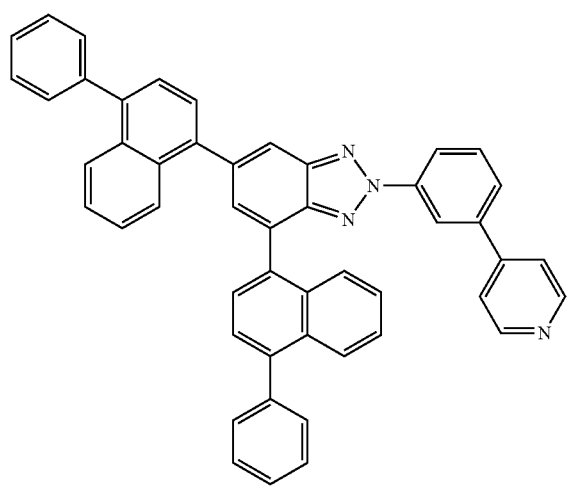
m = 1, X = C
formula (1a-2), formula (1a-4)
(Compound 56)
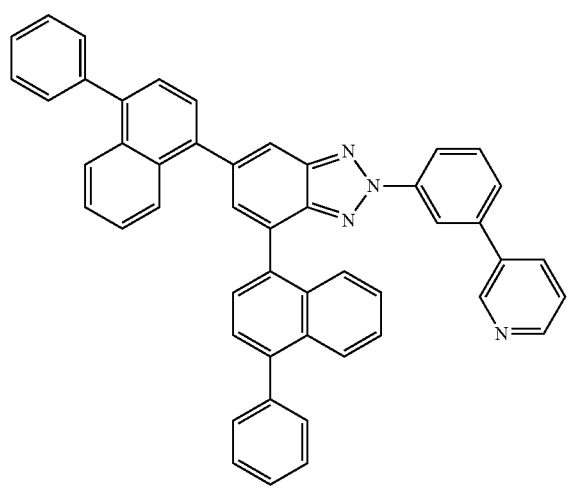
m = 1, X = C
formula (1a-1), formula (1a-4)
(Compound 57)
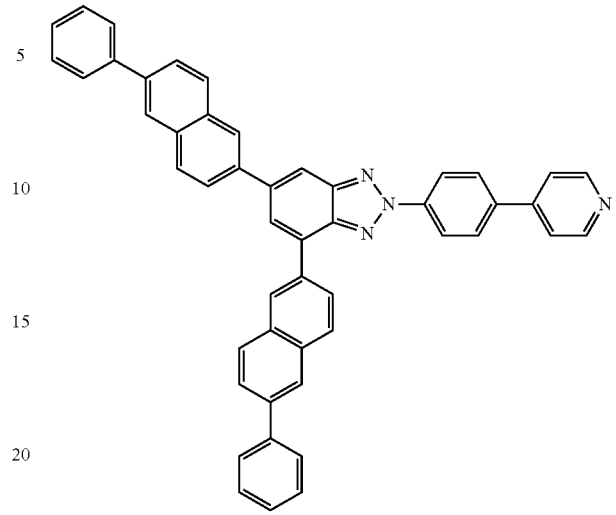
m = 1, X = C
formula (1a-2), formula (1a-3)
(Compound 58)
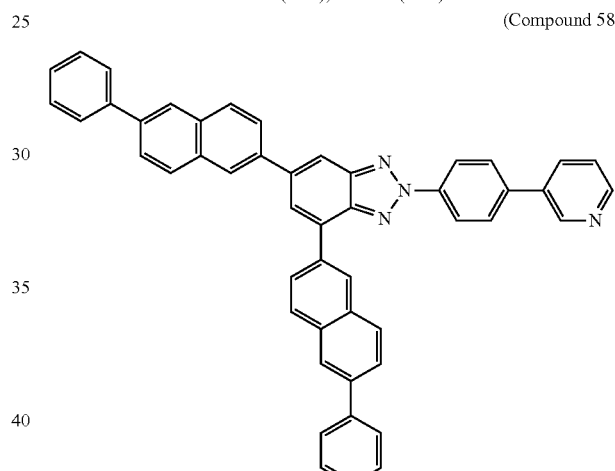
m = 1, X = C
formula (1a-1), formula (1a-3)
(Compound 59)
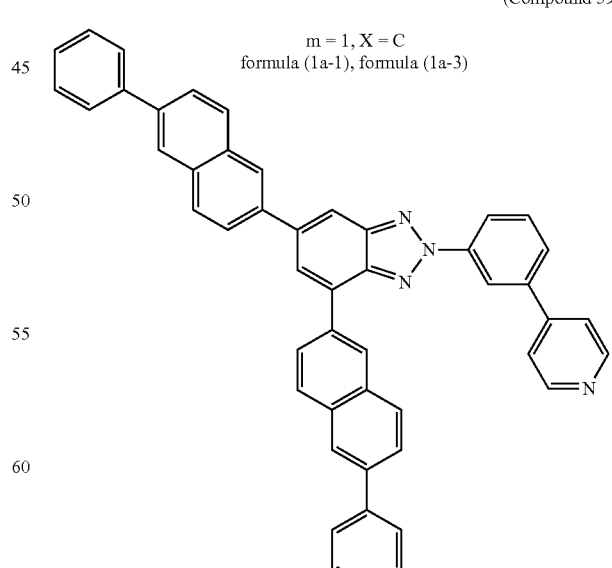
m = 1, X = C
formula (1a-2), formula (1a-4)

(Compound 60)
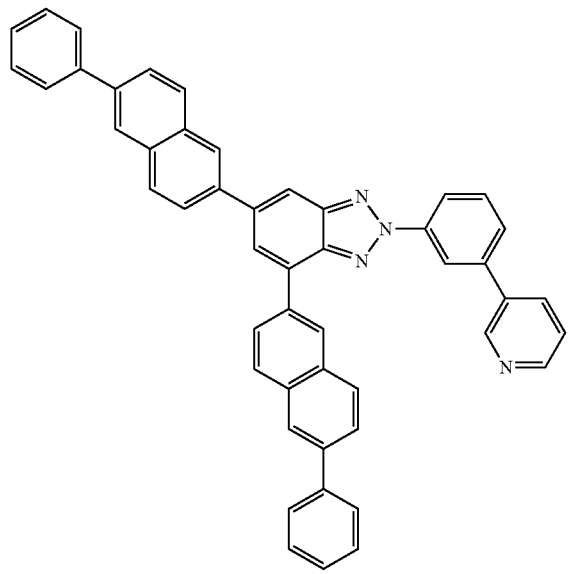
m = 1, X = C
formula (1a-1), formula (1a-4)
(Compound 61)
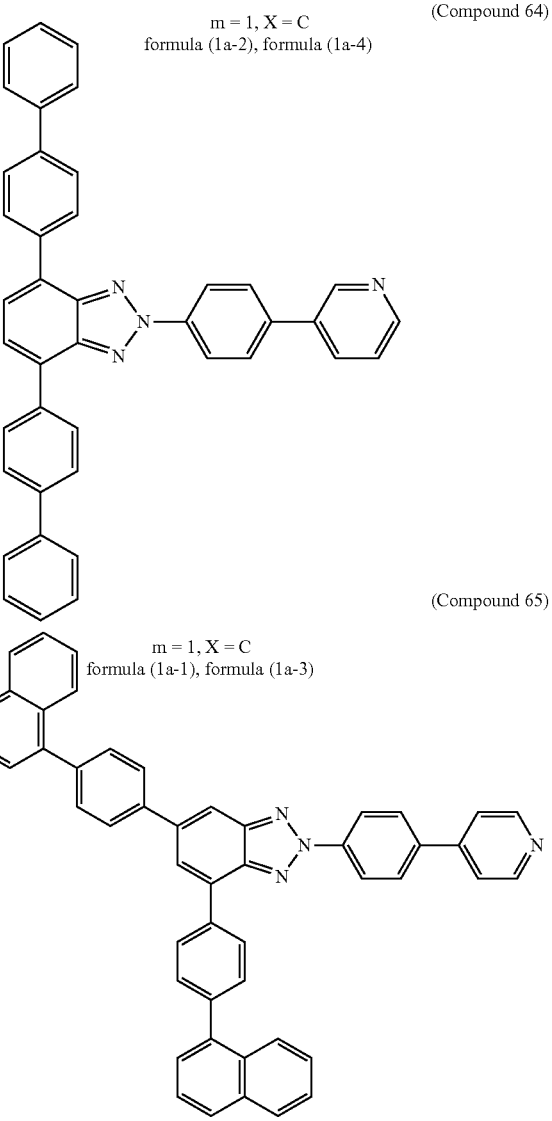
m = 1, X = C
formula (1a-2), formula (1a-3)
(Compound 62)
m = 1, X = C
formula (1a-1), formula (1a-3)
(Compound 63)
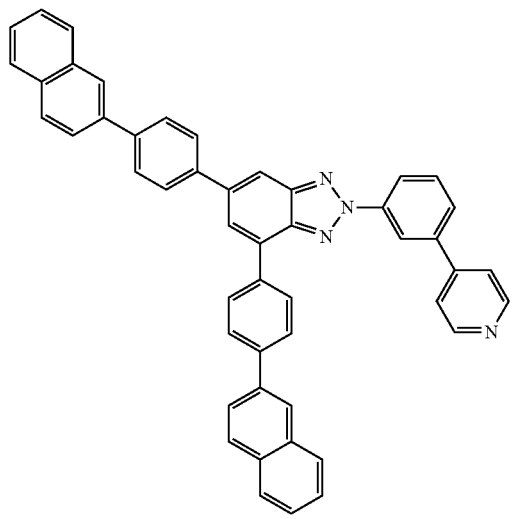
m = 1, X = C
formula (1a-2), formula (1a-4)
(Compound 64)
m = 1, X = C
formula (1a-1), formula (1a-3)
(Compound 65)
m = 1, X = C
formula (1a-2), formula (1a-3)

-continued
(Compound 66)
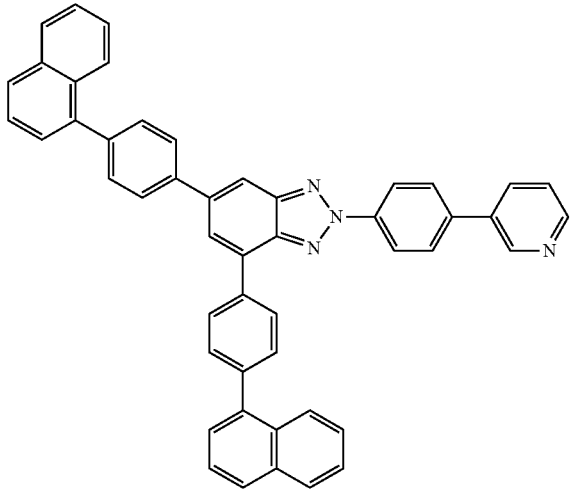
m = 1, X = C
formula (1a-1), formula (1a-3)
(Compound 67)
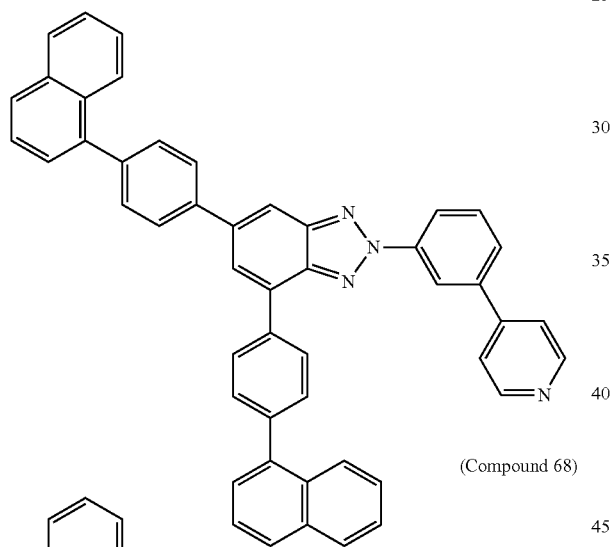
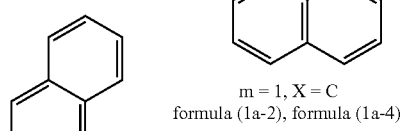
m = 1, X = C
formula (1a-2), formula (1a-4)
(Compound 68)
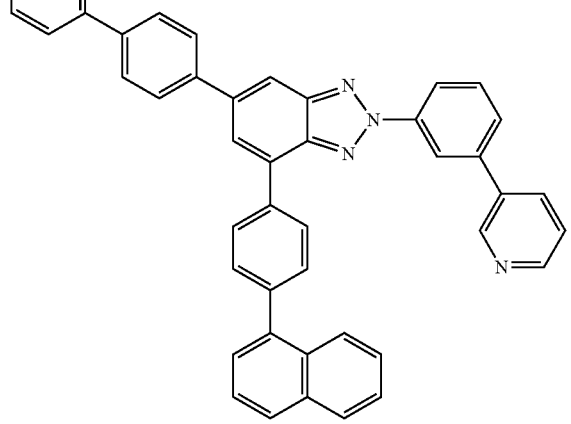
m = 1, X = C
formula (1a-1), formula (1a-4)
-continued
(Compound 69)
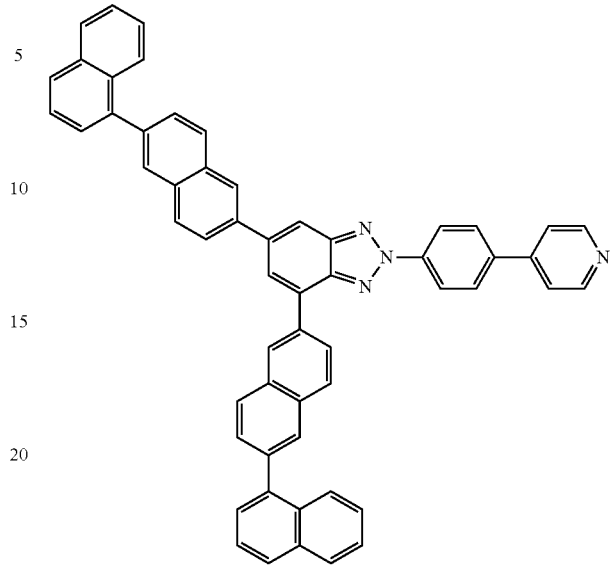
m = 1, X = C
formula (1a-2), formula (1a-3)
(Compound 70)
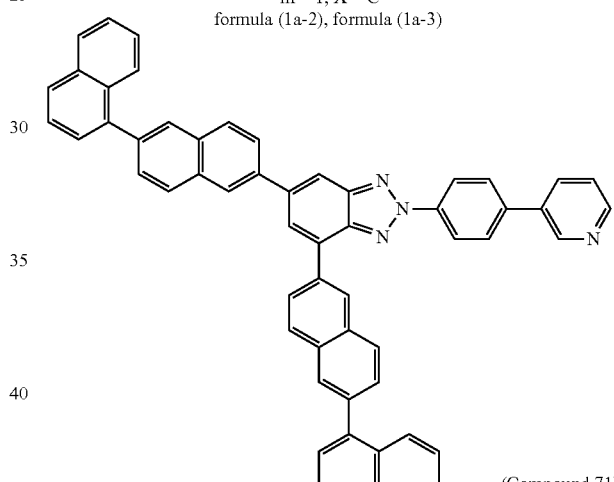
m = 1, X = C
formula (1a-1), formula (1a-3)
(Compound 71)
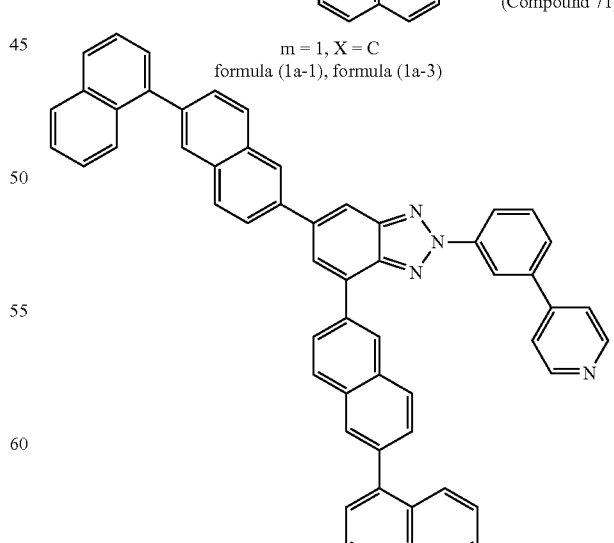
m = 1, X = C
formula (1a-2), formula (1a-4)

(Compound 72)
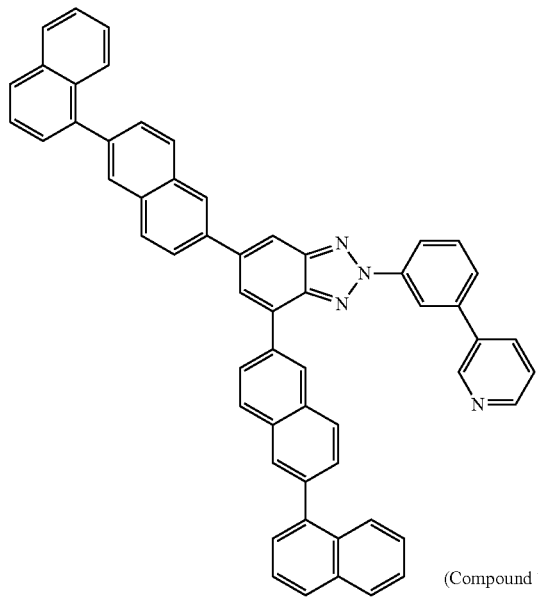
(Compound 73)
m = 1, X = C
formula (1a-1), formula (1a-4)
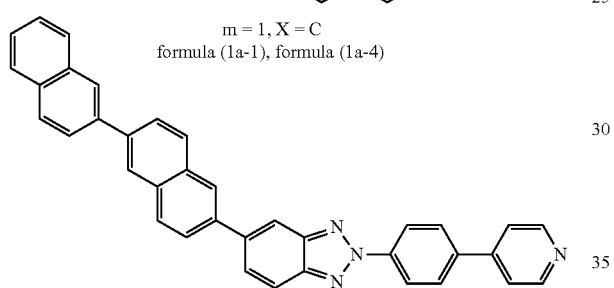
(Compound 74)
m = 1, X = C
formula (1a-2), formula (1a-3)
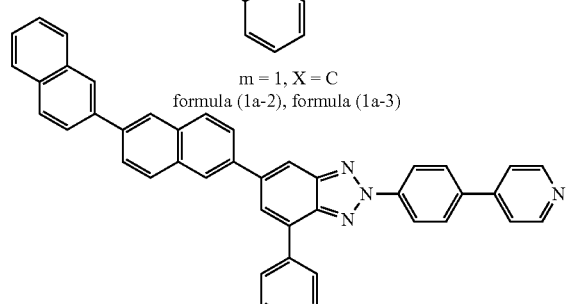
m = 1, X = C
formula (1a-1), formula (1a-3)
(Compound 75)
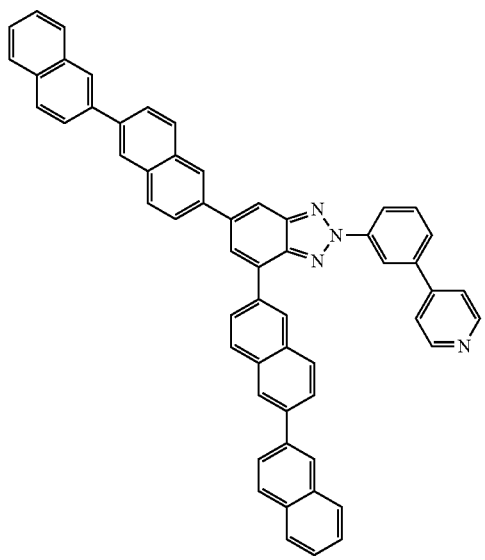
(Compound 76)
m = 1, X = C
formula (1a-2), formula (1a-4)
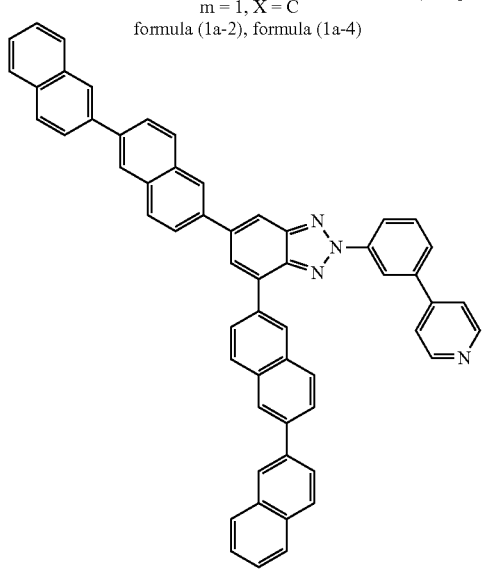
(Compound 77)
m = 1, X = C
formula (1a-1), formula (1a-4)
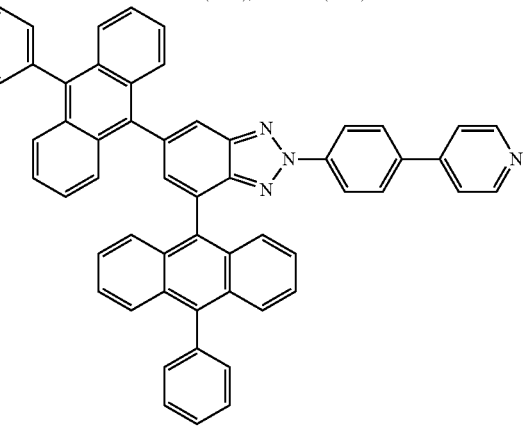
m = 1, X = C
formula (1a-2), formula (1a-3)

(Compound 78)
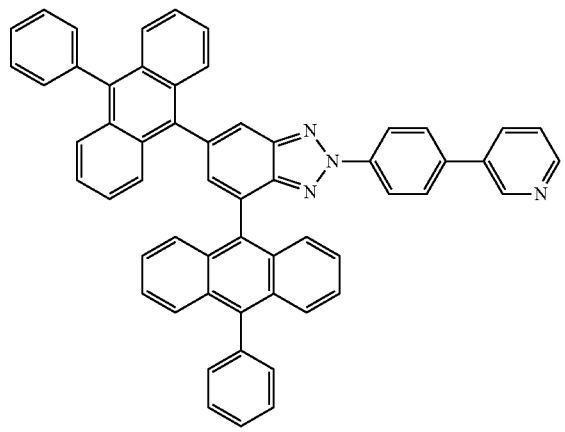
m = 1, X = C
formula (1a-1), formula (1a-3)
(Compound 79)
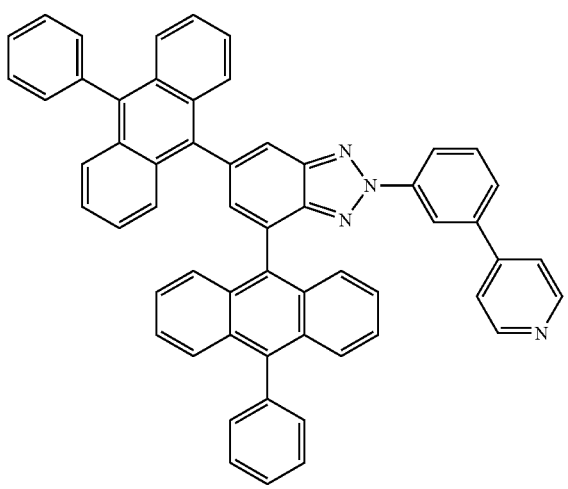
m = 1, X = C
formula (1a-2), formula (1a-4)
(Compound 80)
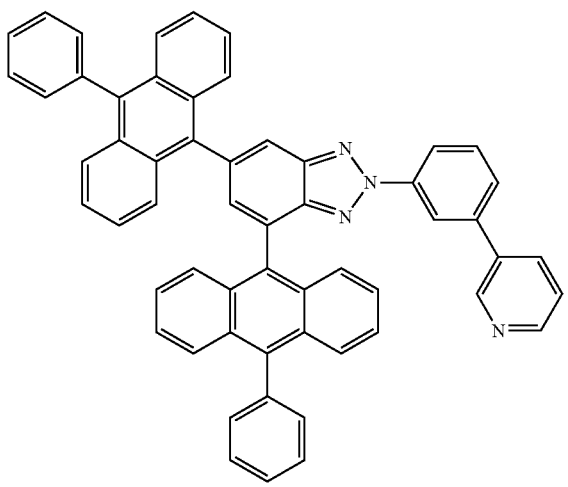
m = 1, X = C
formula (1a-1), formula (1a-4)
(Compound 81)
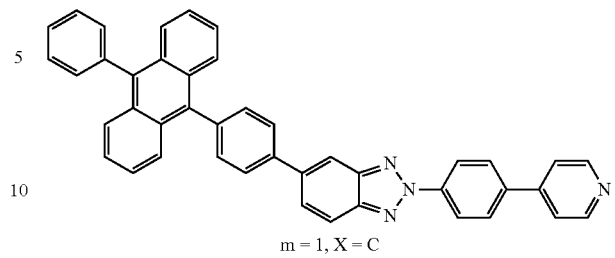
m = 1, X = C
formula (1a-2), formula (1a-3)
(Compound 82)
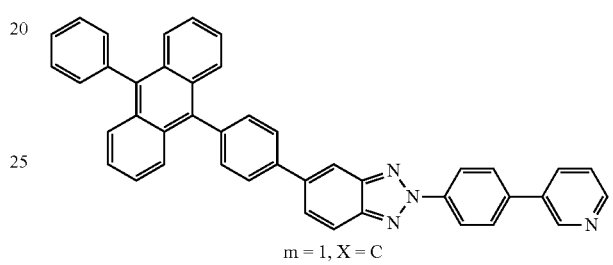
m = 1, X = C
formula (1a-1), formula (1a-3)
(Compound 83)
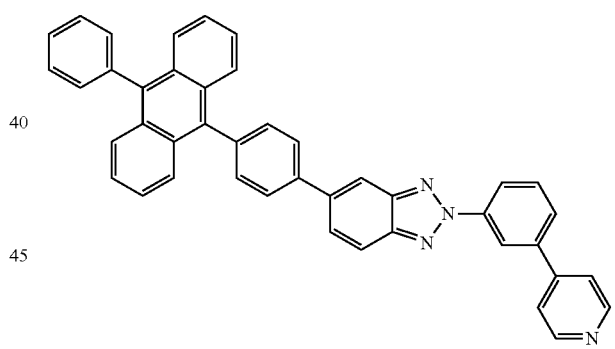
m = 1, X = C
formula (1a-2), formula (1a-4)
(Compound 84)
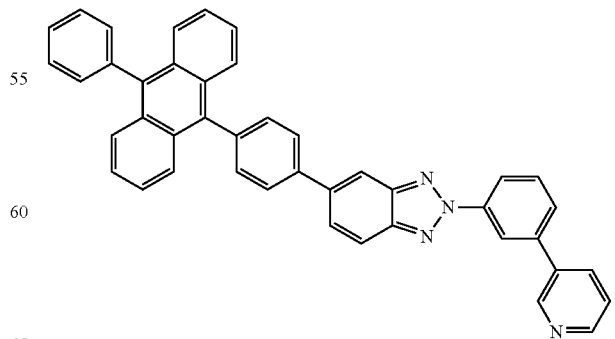
m = 1, X = C
formula (1a-1), formula (1a-4)

(Compound 85)
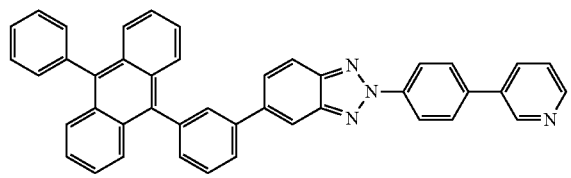
m = 1, X = C
formula (1a-1), formula (1a-3)
(Chmeical 86)
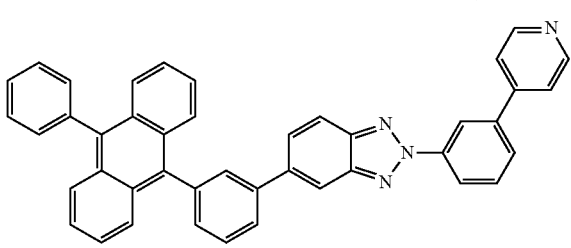
m = 1, X = C
formula (1a-2), formula (1a-4)
(Compound 87)
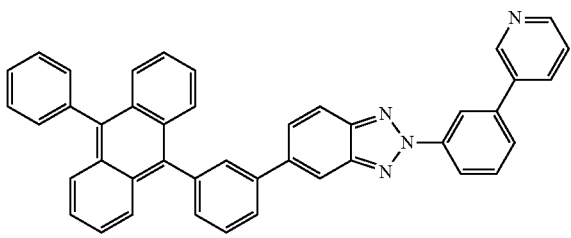
m = 1, X = C
formula (1a-2), formula (1a-4)
(Compound 88)
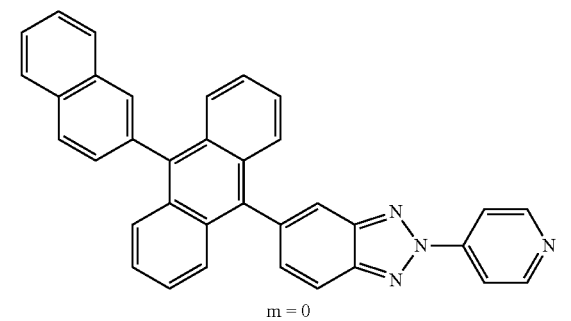
m = 0
(Compound 89)
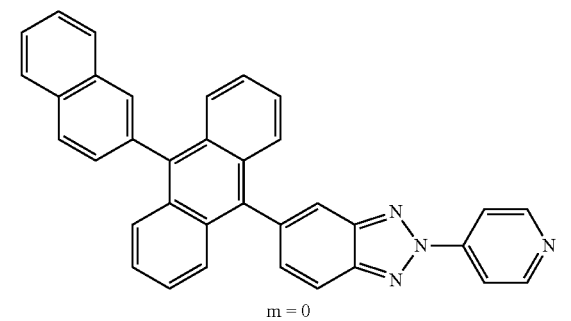
m = 0
(Compound 90)
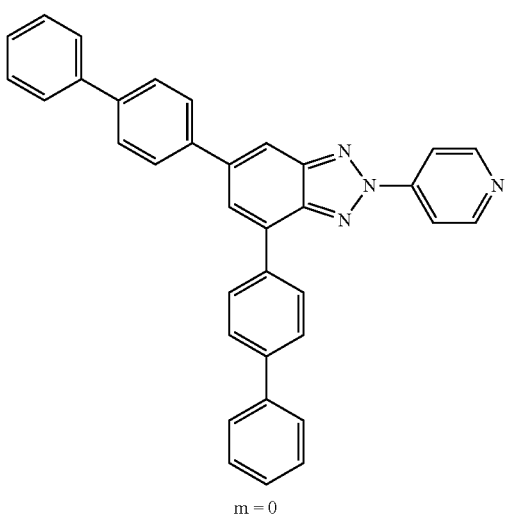
m = 0
(Compound 91)
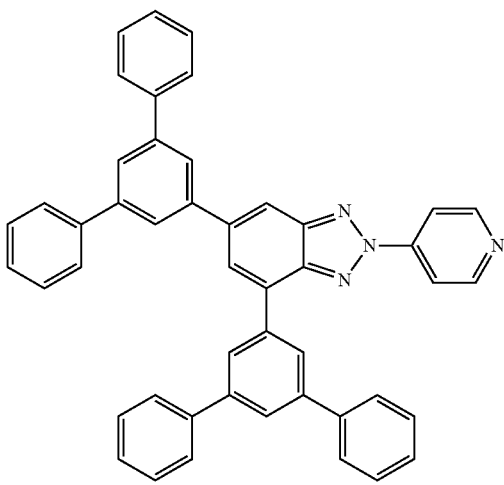
m = 0
(Compound 92)
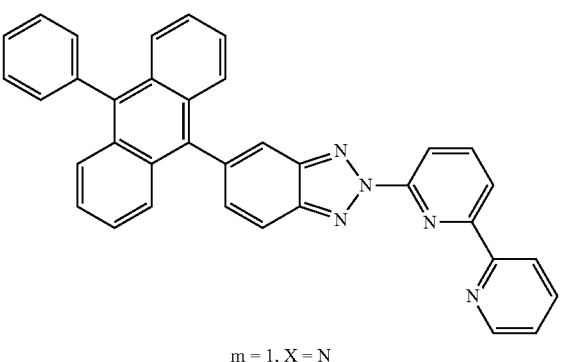
m = 1, X = N -continued
(Compound 93)
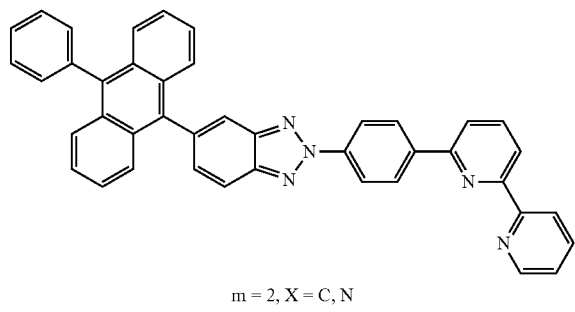
m = 2, X = C, N
(Compound 94)
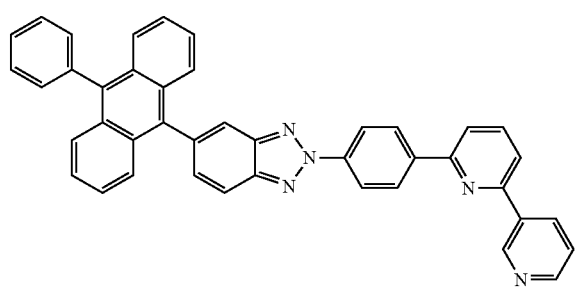
m = 2, X = C, N
(Compound 95)
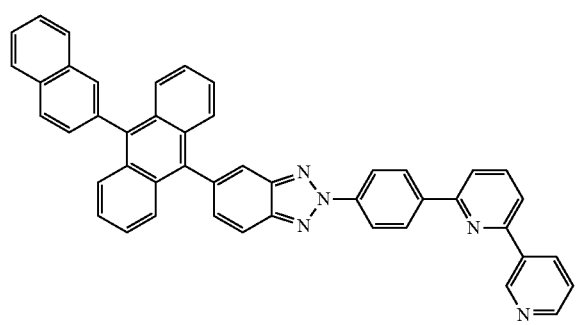
m = 2, X = C, N
(Compound 96)
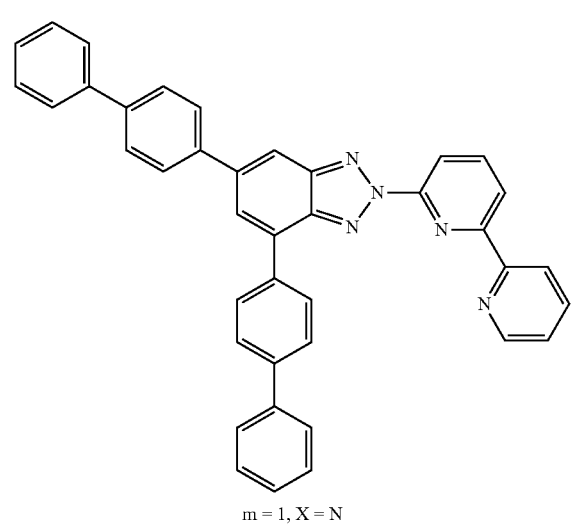
m = 1, X = N
-continued
(Compound 97)
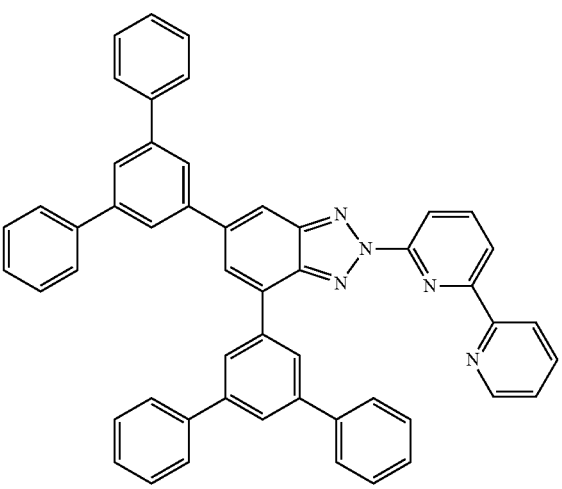
m = 1, X = N
(Compound 98)
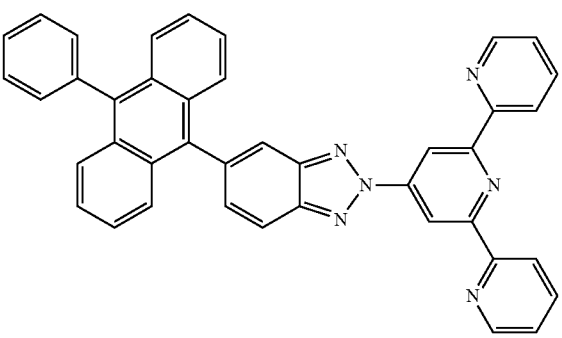
m = 1, X = N
(Compound 99)
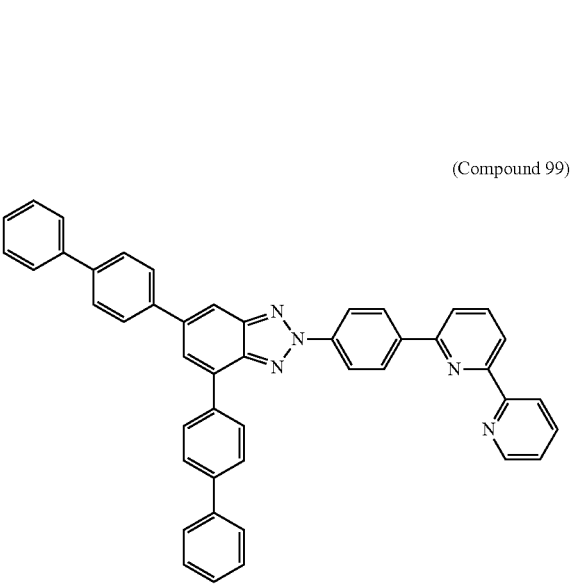
m = 2, X = C, N (Compound 100)
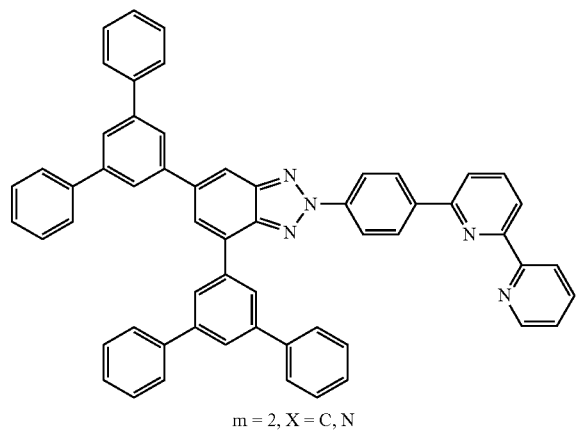
m = 2, X = C, N
(Compound 101)
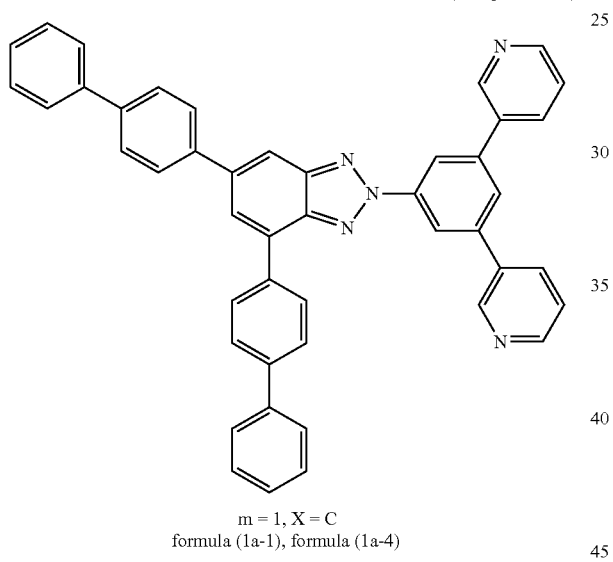
m = 1, X = C
formula (1a-1), formula (1a-4)
(Compound 102)
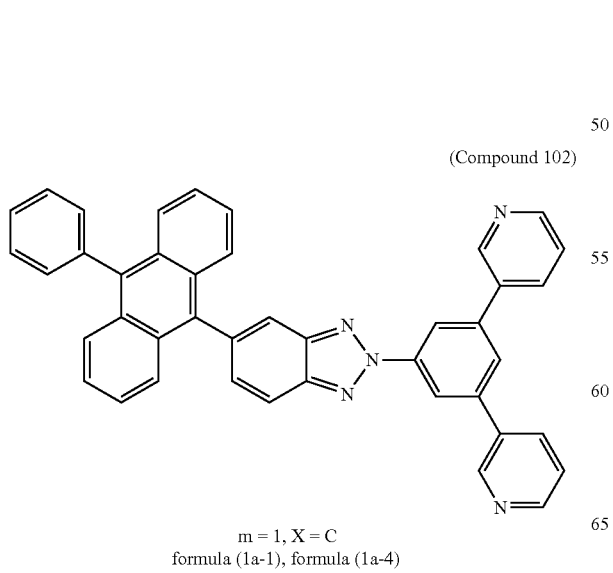
m = 1, X = C
formula (1a-1), formula (1a-4)
(Compound 103)
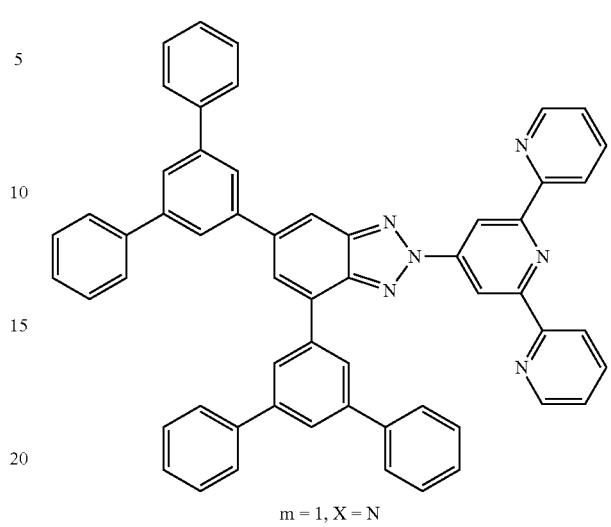
m = 1, X = N
(Compound 104)
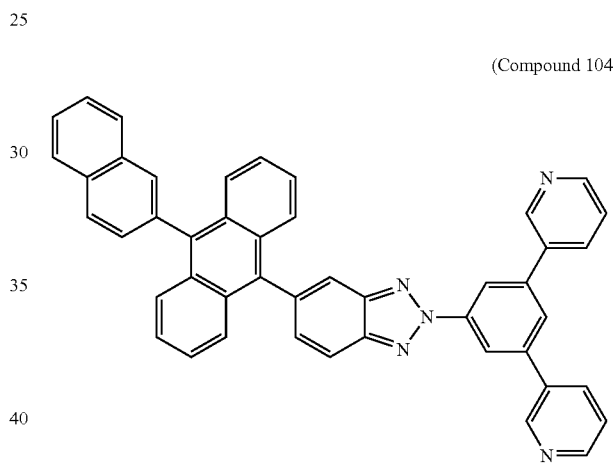
m = 1, X = C
formula (1a-1), formula (1a-4)
(Compound 105)
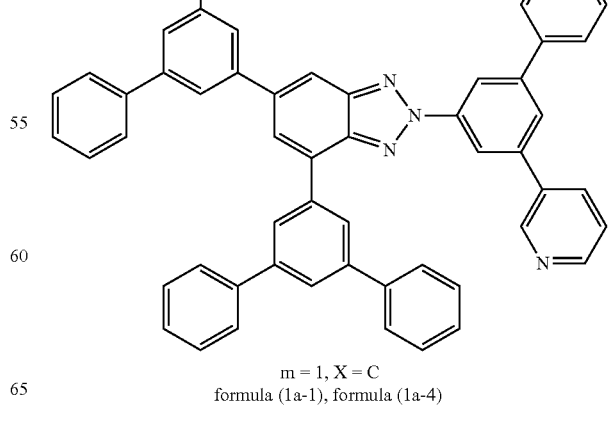
m = 1, X = C
formula (1a-1), formula (1a-4)

(Compound 106)
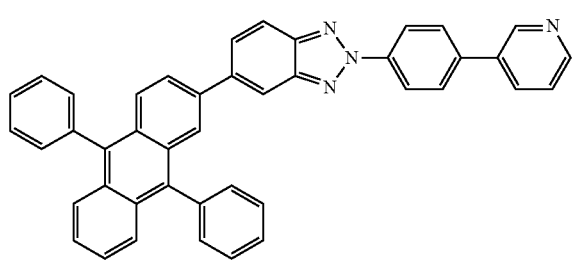
m = 1, X = C
formula (1a-1), formula (1a-3)
(Compound 107)
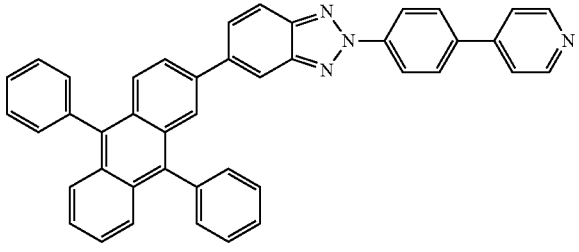
m = 1, X = C
formula (1a-2), formula (1a-3)
(Compound 108)
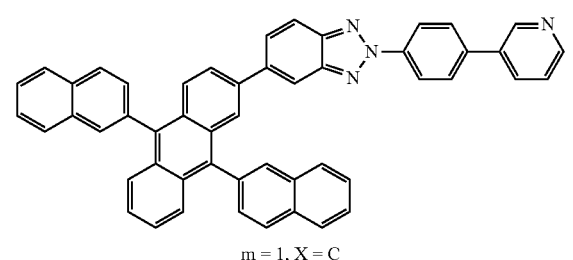
m = 1, X = C
formula (1a-1), formula (1a-3)
(Compound 109)
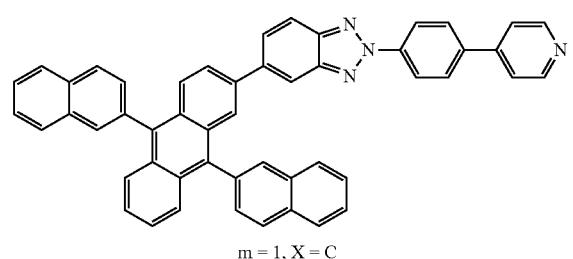
m = 1, X = C
formula (1a-2), formula (1a-3)
(Compound 110)
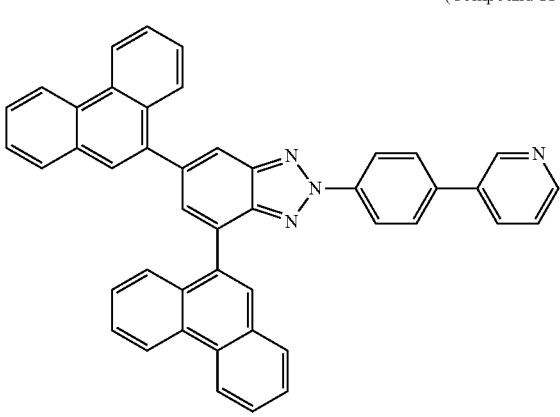
m = 1, X = C
formula (1a-1), formula (1a-3)
(Compound 111)
m = 1, X = C
formula (1a-1), formula (1a-3)
(Compound 112)
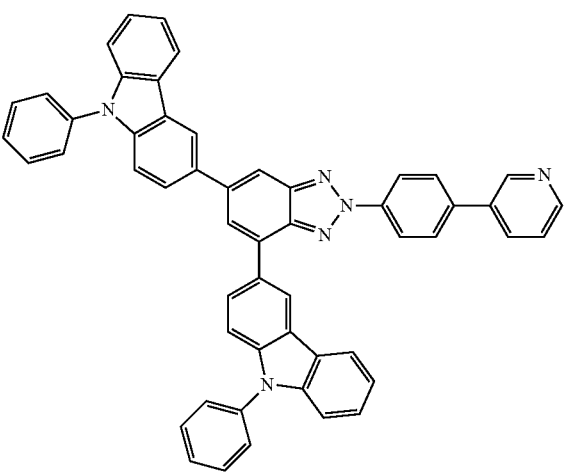
m = 1, X = C
formula (1a-1), formula (1a-3)

-continued (Compound 113)

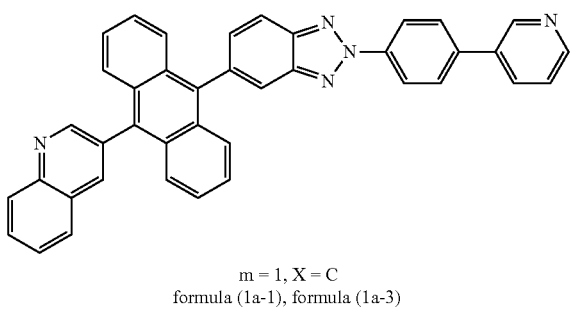

m = 1, X = C
formula (1a-1), formula (1a-3)

The above-mentioned benzotriazole derivative of the invention has a high glass transition point (Tg), is capable of forming a thin film excellent in heat resistance, maintains an amorphous state with stability, and is capable of maintaining the state of a thin film with stability. Moreover, the benzotriazole derivative of the invention features good electron injection property, a high electron migration rate and a high electron-blocking power. For example, a film formed by vapor-depositing the compound of the invention in a thickness of 100 nm can be measured for its work function to exhibit a very high value.

Therefore, the benzotriazole derivative of the invention is very useful as a material for forming an organic layer of an organic EL device.

<Organic EL Device>

Figure 21:
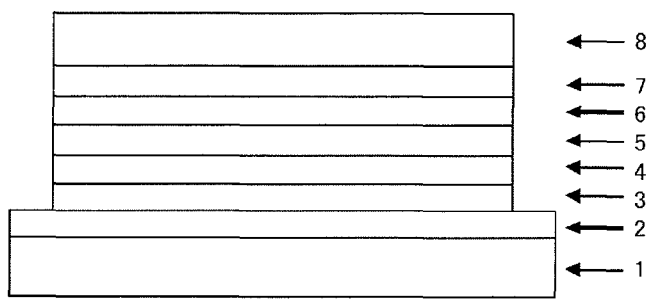
FIG. 21 is a view illustrating the structure of layers of an organic EL device.

The organic EL device having the organic layer formed by using the above compound of the present invention has a structure of layers as shown, for example, in FIG. 21.

Namely, a transparent anode 2, a hole-transporting layer 3, a luminous layer 4, a hole-blocking layer 5, an electron-transporting layer 6, an electron injection layer 7 and a cathode 8 are formed on a glass substrate 1 (which may be any transparent substrate such as transparent resin substrate or the like substrate).

The organic EL device to which the compound of the present invention is applied is not limited to the one of the above layer structure, as a matter of course. For instance, the organic EL device may have an electron-blocking layer formed between the luminous layer 4 and the hole-transporting layer 3, or may have a simplified layer structure omitting the electron injection layer 7 and the hole-blocking layer 5. For instance, some layers can be omitted from the above multilayer structure. Namely, the organic EL device can be fabricated in a simple layer structure having the anode 2, hole-transporting layer 3, luminous layer 4, electron-transporting layer 6 and cathode 8 formed on the substrate 1.

That is, the benzotriazole derivative of the invention is preferably used as a material for forming organic layers (e.g., electron injection layer 7, electron-transporting layer 6, hole-blocking layer 5 and luminous layer 4) between the anode 2 and the cathode 8.

In the organic EL device, the transparent anode 2 may be formed by using an electrode material which has been known per se, i.e., by vapor-depositing an electrode material having a large work function, such as ITO or gold on the substrate 1.

Further, the hole injection layer that is not shown (and that can be formed between the transparent electrode 2 and the hole-transporting layer 3) can be formed by using the material that have been known per se, such as those described below.

Porphyrin compound as represented by copper phthalocyanine;

Triphenylamine derivative of the star burst type;

Arylamine having a structure in which a plurality of triphenylamine skeletons are coupled together via a single bond or a divalent group without hetero atom (e.g., trimer or tetramer of triphenylamine);

High molecular materials of the application type, such as poly(3,4-ethylenedioxythiophene) (PEDOT), poly(styrene sulfonate) (PSS), etc.; and Acceptor-type heterocyclic compounds such as hexacyanoazatriphenylene and the like.

The layer (thin film) can be formed by using the above materials relying not only upon the vacuum evaporation method but also upon the known methods such as spin-coating method or ink-jet method. The layers described below, too, can similarly be formed by the vacuum evaporation, the spin-coating or the ink-jet method.

The hole-transporting layer 3, too, can be formed by using a hole-transporting material that has been known per se. Representative examples of the hole materials are:

Benzidine derivatives such as,

N,N'-Diphenyl-N,N'-di(m-tolyl)benzidine (hereinafter abbreviated as TPD);

N,N'-Diphenyl-N,N'-di(α-naphthyl)benzidine (hereinafter abbreviated as NPD); and N,N,N',N'-Tetrabiphenylylbenzidine; and Amine derivatives such as, 1,1-Bis[4-(di-4-tolylamino)phenyl]cyclohexane (hereinafter abbreviated as TAPC);

Various triphenylamine trimers and tetramers; and

The above-mentioned application-type high molecular materials that can also be used for forming the hole injection layer.

The compounds which are the hole-transporting materials may be used alone to form a film or may be used being mixed together in two or more kinds to form a film. Or the above compounds may be used in one kind or in a plurality of kinds to form a plurality of layers, and a multiplicity of films formed by laminating such layers may be used as a hole-transporting layer.

In forming the hole-transporting layer 3 (the same also holds for the hole injection layer, too), the material usually used for forming the layer may, further, be P-doped with a trisbromophenylaminehexachloroantimony or the like. It is also allowable to form the hole-transporting layer 3 (or the hole injection layer) by using a high molecular compound having a basic skeleton of TPD.

Further, as the electron-blocking layer (that can be formed between the luminous layer 4 and the hole-transporting layer 3) that has not been shown, there can be used a known compound having the electron-blocking action, such as carbazole derivative or a compound that has a triphenylsilyl group yet having a triarylamine structure. Described below are concrete examples of the carbazole derivative and the compound having the triarylamine structure.

<Carbazole Derivatives>

4,4',4''-Tri(N-carbazolyl)triphenylamine (hereinafter abbreviated as TCTA);

9,9-Bis[4-(carbazol-9-yl)phenyl]fluorene;

1,3-Bis(carbazol-9-yl)benzene (hereinafter abbreviated as mCP); and 2,2-Bis[4-(carbazol-9-yl)phenyl]adamantane (hereinafter abbreviated as Ad-Cz).

<Compounds Having a Triarylamine Structure>
9-[4-(carbazol-9-yl)phenyl]-9-[4-(triphenylsilyl)phenyl]-9H-fluorene.

The electron-blocking layer is formed by using one, two or more kinds of the above known hole-transporting materials. It is, however, also allowable to form a plurality of layers by using one or a plurality of kinds of the hole-transporting materials, and use a multiplicity of films formed by laminating such layers as the electron-blocking layer.

The luminous layer 4 of the organic EL device can be formed by using the above benzotriazole derivative of the invention as the luminous material. The luminous layer 4, however, can also be formed by using luminous materials such as a metal complex of a quinolynol derivative as represented by $Alq_3$ as well as various metal complexes such as of zinc, beryllium and aluminum, anthracene derivative, bis-styrylbenzene derivative, pyrene derivative, oxazole derivative and olyparaphenylenevinylene derivative.

It is also allowable to constitute the luminous layer 4 by using a host material and a dopant material.

As the host material in this case, there can be used thiazole derivative, benzimidazole derivative and polydialkylfluorene derivative in addition to the above luminous materials.

As the dopant material, there can be used quinacridone, cumalin, rubrene, perylene and derivatives thereof, benzopyran derivative, Rhodamine derivative and aminostyryl derivative.

The luminous layer 4, too, can be formed in a single-layer structure by using one or two or more kinds of the luminous materials, or in a multi-layer structure by laminating a plurality of layers.

It is, further, allowable to form the luminous layer 4 by using a phosphorescent luminous material as the luminous material.

As the phosphorescent luminous material, there can be used a phosphorescent luminous body of a metal complex such as of iridium or platinum. For example, there can be used a green luminous phosphor such as $Ir(ppy)_3$, a blue luminous phosphor such as Flrpic or $Flr_6$, and a red luminous phosphor such as $Btp_2Ir(acac)$. These phosphorescent luminous materials are used by being doped to the hole-transporting host material or the electron-transporting host material.

As the hole-transporting host material, there can be used carbazole derivative such as 4,4'-di(N-carbazolyl)biphenyl (hereinafter abbreviated as CBP), TCTA or mCP, as well as the compound of the present invention.

As the electron-transporting host material, there can be used p-bis(triphenylsilyl)benzene (hereinafter abbreviated as UGH2) or 2,2',2''-(1,3,5-phenylene)-tris(1-phenyl-1H-benzimidazole) (hereinafter abbreviated as TPBI).

To avoid the concentration quenching, the host material is desirably doped with the phosphorescent luminous material in an amount in a range of 1 to 30% by weight relative to the whole luminous layer relying on the vacuum coevaporation.

The hole-blocking layer 5 of the organic EL element can also be formed by using a compound having hole-blocking action that has been known per se. In addition to using the benzotriazole derivative of the present invention.

As the known compound having the hole-blocking action, there can be exemplified phenanthroline derivatives such as bathocuproin (hereinafter abbreviated as BCP), metal complexes of quinolinol derivatives such as aluminum (III) bis(2-methyl-8-quinolinato)-4-phenylphenolate (hereinafter abbreviated as BAlq) and the like, as well as triazole derivatives, triazine derivatives and oxadiazole derivatives.

These materials can also be used for forming the electron-transporting layer 6 that will be described below. Moreover, the hole-blocking layer 5 and the electron-transporting layer 6 can be formed as one layer.

The hole-blocking layer 5, too, can be formed in the structure of a single layer or of a laminate of a multiplicity of layers, the layers being formed by using one kind, two kinds or more kinds of the above-mentioned compounds having hole-blocking action.

The electron-transporting layer 6 can be formed by using electron-transporting compounds that have been known per se. Such as metal complexes of quinolinol derivatives like $Alq_3$, BAlq, as well as various metal complexes such as of zinc, beryllium and aluminum, triazole derivatives, triazine derivatives, oxadiazole derivatives, thiadiazole derivatives, carbodiimide derivatives, quinoxaline derivatives, phenanthroline derivatives and silole derivatives in addition to using the benzotriazole derivatives of the present invention.

The electron-transporting layer 6, too, can be formed in the structure of a single layer or of a laminate of a multiplicity of layers, the layers being formed by using one kind, two kinds or more kinds of the above-mentioned electron-transporting compounds.

The electron injection layer 7, too, can be formed by using known compounds, i.e., by using alkal metal salts such as lithium fluoride and cesium fluoride, alkaline earth metal salts such as magnesium fluoride, and metal oxides such as aluminum oxide in addition to using the benzotriazole derivatives of the present invention.

As the cathode 8 of the organic EL device, there can be used an electrode material having a low work function, such as aluminum, or an electrode material of an alloy having a lower work function, such as magnesium-silver alloy, magnesium-indium alloy or aluminum-magnesium alloy.

The organic EL device forming at least one of the organic layers (e.g., at least any one of electron injection layer 7, electron-transporting layer 6, hole-blocking layer 5 or luminous layer 4) by using the benzotriazole derivative of the present invention, features a high luminous efficiency, a high power efficiency, a low practical driving voltage, a low luminance start voltage and very excellent durability.

EXAMPLES

The invention will now be concretely described by way of Examples to which only, however, the invention is in no way limited.

Example 1

Synthesis of a 5-(10-phenyl-anthracen-9-yl)-2-{4-(pyridin-3-yl)phenyl}-2H-benzotriazole (Synthesis of a Compound 4)

(Compound 4)

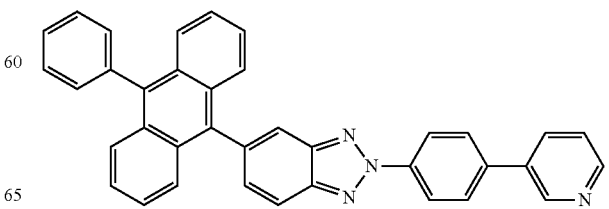

| | |
|---|---|
| 1-Bromo-4-nitrobenzene | 50 g, |
| 3-Pyridineboronic acid | 31.9 g, |
| 2M Potassium carbonate aqueous solution | 309 ml, |
| Toluene | 200 ml, |
| Ethanol | 40 ml, and |
| Tetrakistriphenylphosphine palladium (0) | 11.0 g, | were put into a reaction vessel purged with nitrogen, and were heated and refluxed for 14 hours with stirring. The reaction solution was concentrated and the precipitated crystals were picked up by filtration. Through the dispersion washing with an isopropanol, there was obtained a grey powder of 3-(4-nitrophenyl)pyridine crystals in an amount of 43.5 g (yield, 88.80).

| | |
|---|---|
| The thus obtained 3-(4-nitrophenyl)pyridine | 3.5 g, |
| 4-Bromo-1,2-diaminobenzene | 3.6 g, |
| Caustic soda | 1.4 g, and |
| Toluene | 50 ml, | were put into the reaction vessel purged with nitrogen, and were heated and refluxed for 7 hours with stirring.

100 Milliliters of toluene was added thereto to extract the reaction solution which was then concentrated under a reduced pressure and was refined by the column chromatography to obtain 1.83 g of a red powder of 5-bromo-2-{4-(pyridin-3-yl)phenylazo}phenylamine crystals (yield, 38.10).

| | |
|---|---|
| The thus obtained amine | 1.5 g, |
| Iodobenzene diacetate | 2.0 g, and |
| Toluene | 30 ml, | were put into the reaction vessel purged with nitrogen, and were stirred at 74° C. for one hour. The organic layer was picked up by the separating operation, concentrated under a reduced pressure and was refined by the column chromatography to obtain 0.8 g of a white powder of 5-bromo-2-{4-(pyridin-3-yl)phenyl}-2H-benzotriazole crystals (yield, 58.60).

| | |
|---|---|
| The thus obtained 5-bromo-2-{4-(pyridin-3-yl)phenyl}-2H-benzotriazole | 5.0 g, |
| 9-Phenylanthracen-10-ylboronic acid | 4.7 g, |
| 2M Potassium carbonate aqueous solution | 21 ml, |
| Toluene | 50 ml, |
| Ethanol | 10 ml, and |

Tetrakistriphenylphosphine palladium (0) 0.8 g, were put into the reaction vessel purged with nitrogen, and were heated and refluxed for 8.5 hours with stirring.

The organic layer was picked up by the separating operation, concentrated under a reduced pressure and was refined by the column chromatography to obtain 10.4 g of a yellow powder of 5-(10-phenyl-anthracen-9-yl)-2-{4-(pyridin-3-yl)phenyl}-2H-benzotriazole (compound 4) (yield, 82.7%).

The obtained yellow powder was identified for its structure by the NMR. FIG. 1 shows the results of the $^1$H-NMR measurement.

The following 24 signals of hydrogen were detected by the $^1$H-NMR (CDCl$_3$).

$\delta$(ppm) = 8.97 (1H)

8.66 (2H)

8.57 (2H)

8.16 (1H)

8.10 (1H)

7.98 (1H)

7.83 (2H)

7.76 – 7.73 (4H)

7.57 (6H)

7.43 (1H)

7.35 (4H)

Example 2

Synthesis of a 5-(10-phenyl-anthracen-9-yl)-2-{3-(pyridin-4-yl)phenyl}-2H-benzotriazole (Synthesis of a Compound 5)

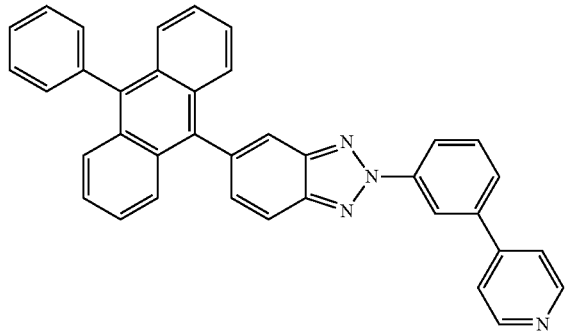

(Compound 5)

A 5-bromo-2-{3-(pyridin-4-yl)phenyl}-2H-benzotriazole was synthesized from a 1-bromo-3-nitrobenzene and a pyridin-4-ylboronic acid in the same manner as in Example 1.

| | |
|---|---|
| The above 5-bromo-2-{3-(pyridin-4-yl)phenyl}-2H-benzotriazole | 2.9 g, |
| 9-Phenylanthracen-10-ylboronic acid | 2.6 g, |
| 2M Potassium carbonate aqueous solution | 12 ml, |
| Toluene | 30 ml, |
| Ethanol | 5.6 ml, and |

Tetrakistriphenylphosphine palladium (0) 0.4 g, were put into the reaction vessel purged with nitrogen, and were heated and refluxed for 7.5 hours with stirring.

The organic layer was picked up by the separating operation, concentrated under a reduced pressure and was refined by the column chromatography to obtain 1.7 g of a yellow powder of 5-(10-phenyl-anthracen-9-yl)-2-{3-(pyridin-4-yl)phenyl}-2H-benzotriazole (compound 5) (yield, 38.7%).

Figure 2:
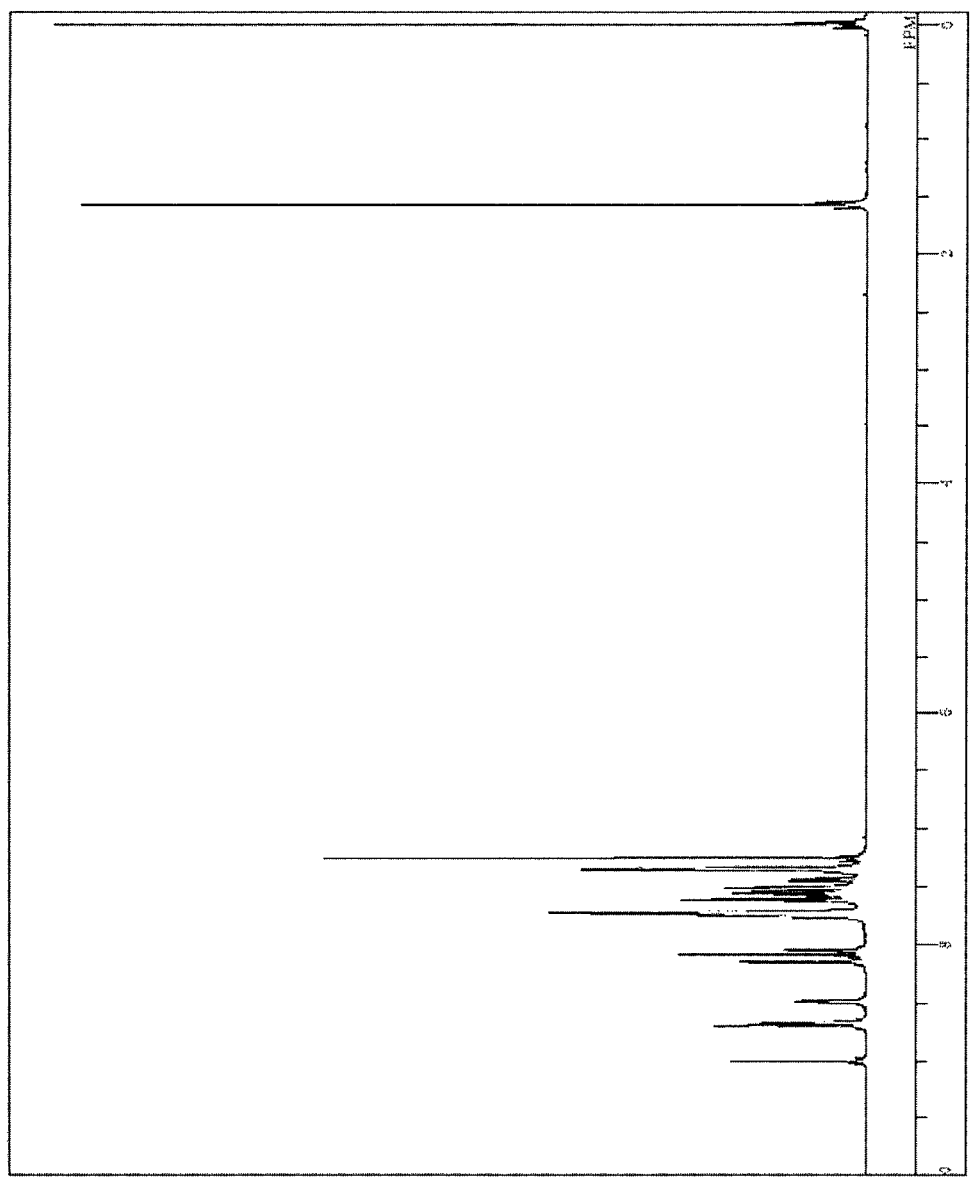
FIG. 2 is a ¹H-NMR chart of a compound (compound 5) of Example 2.

The obtained yellow powder was identified for its structure by the NMR. FIG. 2 shows the results of the $^1$H-NMR measurement.

The following 24 signals of hydrogen were detected by the $^1$H-NMR (CDCl$_3$).

$\delta$(ppm) = 9.02 (1H)
8.69 (2H)
8.5 (1H)
8.16 (1H)
8.1 (1H)
8.06 (1H)
7.76 – 7.71 (6H)
7.63 (2H)
7.57 (2H)
7.51 (2H)
7.45 (1H)
7.36 (4H)

Example 3

Synthesis of a 5-{10-naphthalen-1-yl)anthracen-9-yl}-2-{4-(pyridin-3-yl)phenyl}-2H-benzotriazole
(Synthesis of a Compound 8)

(Compound 8)

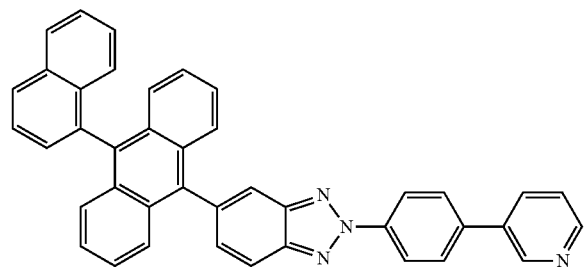

| The above 5-bromo-2-{4-(pyridin-3-yl)phenyl}-2H-benzotriazole synthesized in Example 1 | 4.0 g, |
| --- | --- |
| 10-(Naphthalen-1-yl)anthracen-9-ylboronic acid | 4.8 g, |
| 2M Potassium carbonate aqueous solution | 17 ml, |
| Toluene | 28 ml, and |
| Ethanol | 7 ml, | were put into the reaction vessel purged with nitrogen, and through which the nitrogen gas was flown for 60 minutes with stirring.

Next, 0.7 g of the tetrakistriphenylphosphine palladium (0) was added thereto, and the mixture was heated and refluxed for 10.5 hours with stirring. The organic layer was picked up by the separating operation, concentrated under a reduced pressure and was refined by the column chromatography to obtain 3.5 g of a yellow powder of 5-{10-(naphthalen-1-yl)anthracen-9-yl}-2-{4-(pyridin-3-yl)phenyl}-2H-benzotriazole (compound 8) (yield, 53.5%).

Figure 3:
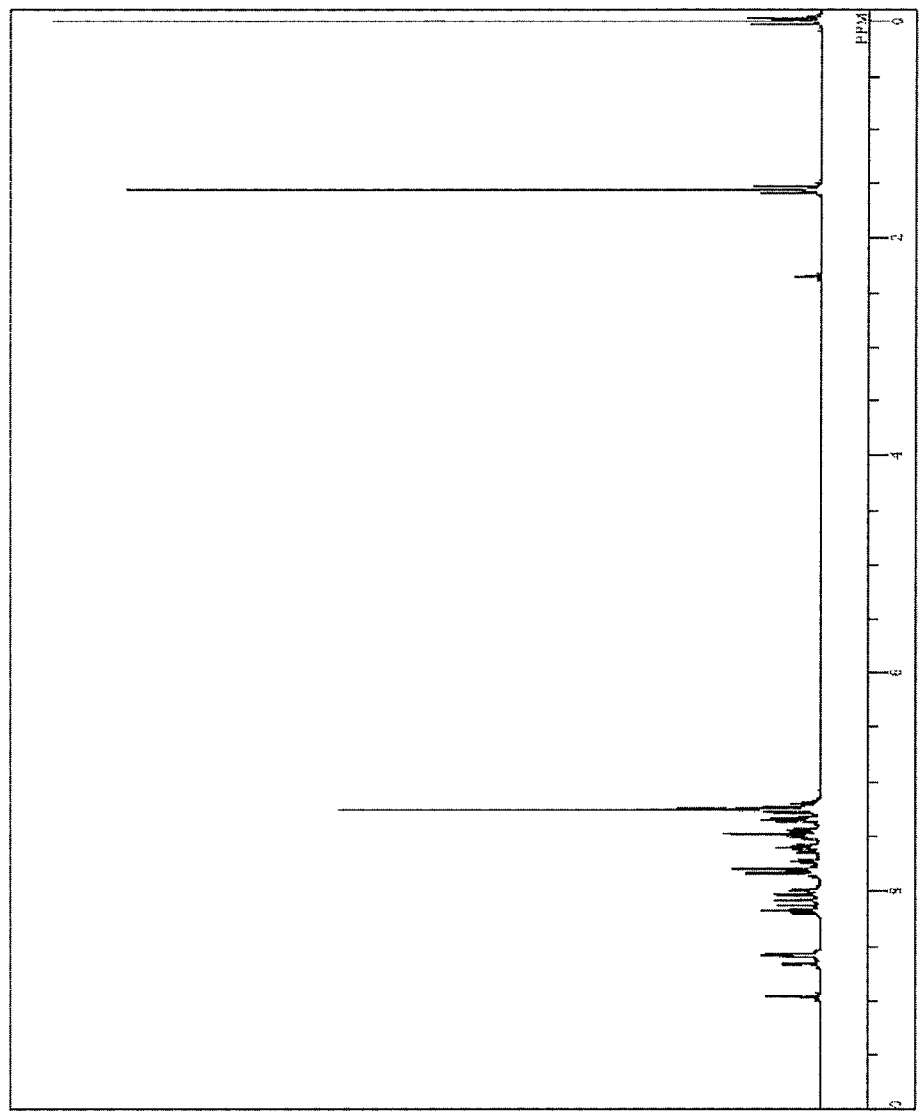
FIG. 3 is a ¹H-NMR chart of a compound (compound 8) of Example 3.

The obtained yellow powder was identified for its structure by the NMR. FIG. 3 shows the results of the $^1$H-NMR measurement.

The following 26 signals of hydrogen were detected by the $^1$H-NMR (CDCl$_3$).

$\delta$(ppm) = 8.98 (1H)
8.67 (1H)
8.59 (2H)
8.19 (2H)
8.09 (1H)
8.04 (1H)
8.00 (1H)
7.84 (1H)
7.80 (1H)
7.73 (1H)
7.61 (1H)
7.47 (4H)
7.35 (2H)
7.25 (7H)

Example 4

Synthesis of a 5-{10-naphthalen-1-yl)anthracen-9-yl}-2-{3-(pyridin-3-yl)phenyl}-2H-benzotriazole
(Synthesis of a Compound 10)

(Compound 10)

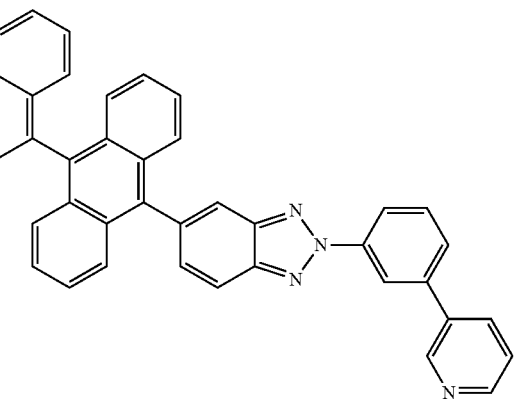

A 5-bromo-2-{3-(pyridin-3-yl)phenyl}-2H-benzotriazole was synthesized from the 1-bromo-3-nitrobenzene and a 3-pyridineboronic acid in the same manner as in Example 1.

| The above 5-bromo-2-{3-(pyridin-3-yl)phenyl}-2H-benzotriazole | 2.9 g, |
| --- | --- |
| 10-(Naphthalen-1-yl)anthracen-9-ylboronic acid | 3.5 g, |
| 2M Potassium carbonate aqueous solution | 12 ml, |
| Toluene | 20 ml, |

| | |
|---|---|
| Ethanol | 5 ml, and |
| Tetrakistriphenylphosphine palladium (0) | 0.5 g, | were put into the reaction vessel purged with nitrogen, and were heated and refluxed for 8.5 hours with stirring.

The organic layer was picked up by the separating operation, concentrated under a reduced pressure and was refined by the column chromatography to obtain 2.1 g of a yellow powder of 5-{10-(naphthalen-1-yl)anthracen-9-yl}-2-{3-(pyridin-3-yl)phenyl}-2H-benzotriazole (compound 10) (yield, 44.0%).

Figure 4:
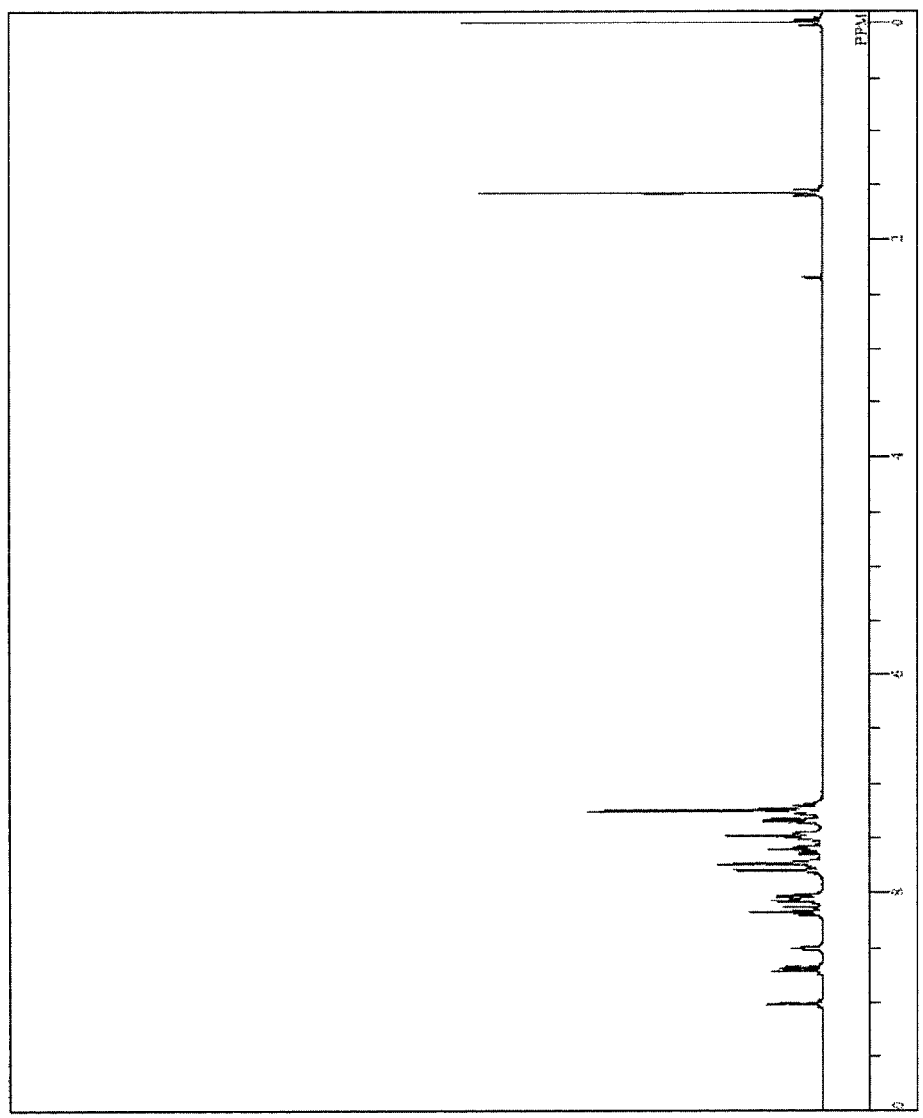
FIG. 4 is a ¹H-NMR chart of a compound (compound 10) of Example 4.

The obtained yellow powder was identified for its structure by the NMR. FIG. 4 shows the results of the $^1$H-NMR measurement.

The following 26 signals of hydrogen were detected by the $^1$H-NMR (CDCl$_3$).

$\delta$(ppm) = 9.02 (1H)

8.70 (2H)

8.51 (1H)

8.19 (1H)

8.06 (3H)

7.80 (2H)

7.73 (2H)

7.60 (2H)

7.49 (4H)

7.34 (2H)

7.23 (6H)

Example 5

Synthesis of a 5-{10-naphthalen-2-yl)anthracen-9-yl}-2-{4-(pyridin-3-yl)phenyl}-2H-benzotriazole
(Synthesis of a Compound 14)

(Compound 14)

| | |
|---|---|
| The 5-bromo-2-{4-(pyridin-3-yl)phenyl}-2H-benzotriazole synthesized in Example 1 | 4.0 g, |
| 10-(Naphthalen-2-yl)anthracen-9-ylboronic acid | 4.76 g, |
| 2M Potassium carbonate aqueous solution | 17 ml, |
| Toluene | 28 ml, |

| | |
|---|---|
| Ethanol | 7 ml, and |
| Tetrakistriphenylphosphine palladium (0) | 0.4 g, | were put into the reaction vessel purged with nitrogen, and were heated and refluxed for 8.5 hours with stirring. The organic layer was picked up by the separating operation, concentrated under a reduced pressure and was refined by the column chromatography to obtain 1.5 g of a yellow powder of 5-{10-(naphthalen-2-yl)anthracen-9-yl}-2-{4-(pyridin-3-yl)phenyl}-2H-benzotriazole (compound 14) (yield, 22.9%).

Figure 5:
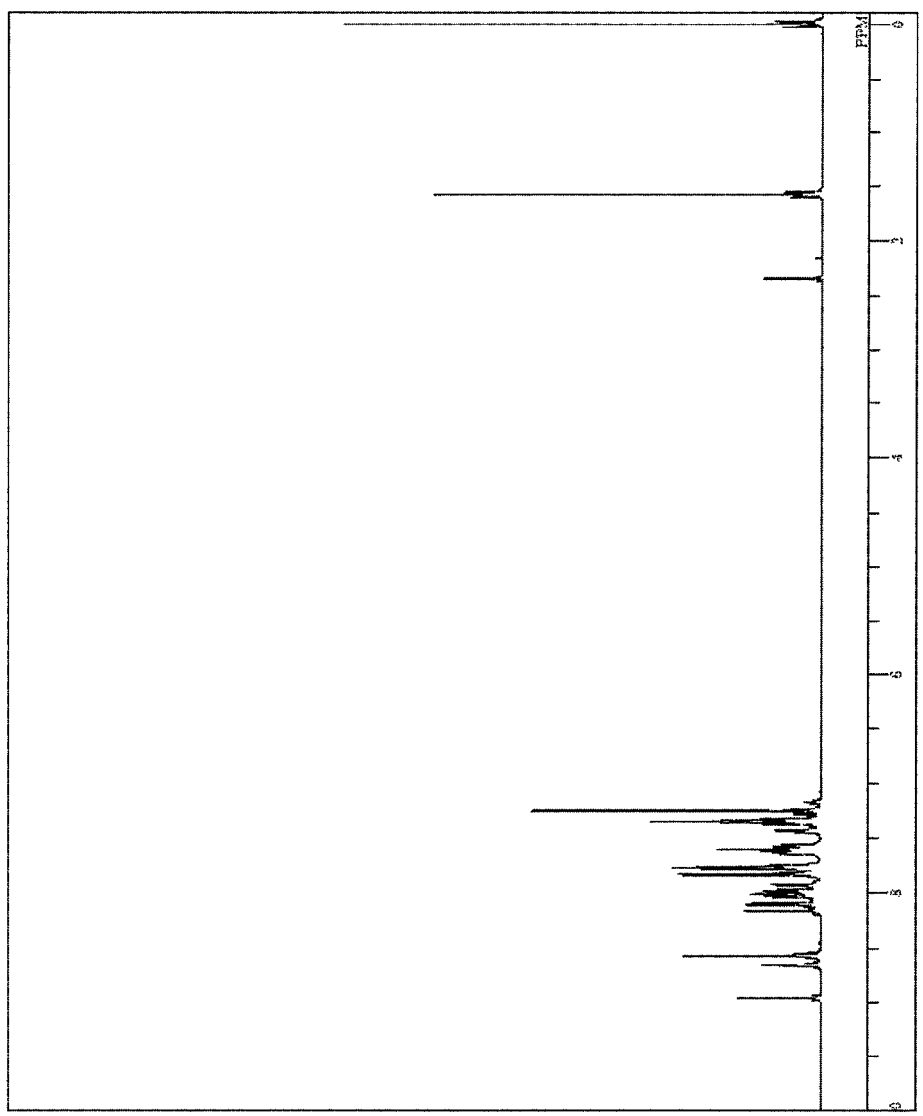
FIG. 5 is a ¹H-NMR chart of a compound (compound 14) of Example 5.

The obtained yellow powder was identified for its structure by the NMR. FIG. 5 shows the results of the $^1$H-NMR measurement.

The following 26 signals of hydrogen were detected by the $^1$H-NMR (CDCl$_3$).

$\delta$(ppm) = 8.97 (1H)

8.67 (1H)

8.58 (2H)

8.18 (1H)

8.11 (2H)

8.05 – 7.98 (2H)

7.94 (1H)

7.84 (2H)

7.77 (4H)

7.61 (4H)

7.44 (1H)

7.37 – 7.32 (4H)

7.26 (1H)

Example 6

Synthesis of a 5-{10-naphthalen-2-yl)anthracen-9-yl}-2-{3-(pyridin-3-yl)phenyl}-2H-benzotriazole
(Synthesis of a Compound 15)

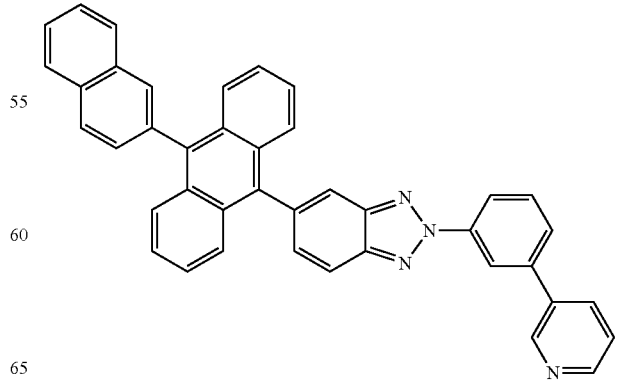

(Compound 15)

| | |
|---|---|
| The 5-bromo-2-{3-(pyridin-3-yl)phenyl}-2H-benzotriazole synthesized in Example 4 | 5.0 g, |
| 10-(Naphthalen-2-yl)anthracen-9-ylboronic acid | 5.95 g, |
| 2M Potassium carbonate aqueous solution | 21 ml, |
| Toluene | 35 ml, |
| Ethanol | 9 ml, and |
| Tetrakistriphenylphosphine palladium (0) | 0.5 g, | were put into the reaction vessel purged with nitrogen, and were heated and refluxed for 8.5 hours with stirring.

The organic layer was picked up by the separating operation, concentrated under a reduced pressure and was refined by the column chromatography to obtain 6.3 g of a yellow powder of 5-{10-(naphthalen-2-yl)anthracen-9-yl)-2-{3-(pyridin-3-yl)phenyl}-2H-benzotriazole (compound 15) (yield, 76.5%).

Figure 6:
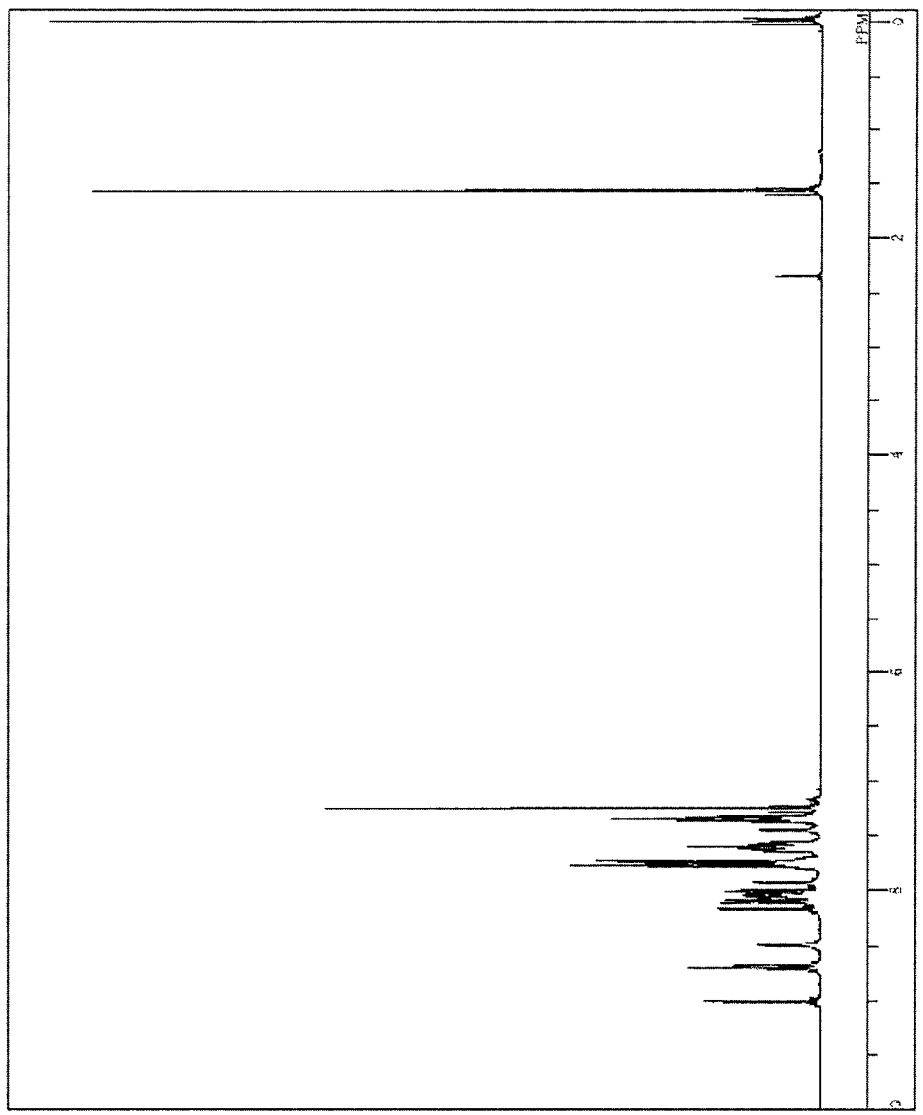
FIG. 6 is a ¹H-NMR chart of a compound (compound 15) of Example 6.

The obtained yellow powder was identified for its structure by the NMR. FIG. 6 shows the results of the $^1$H-NMR measurement.

The following 26 signals of hydrogen were detected by the $^1$H-NMR (CDCl$_3$).

$$\delta(ppm) = \begin{array}{l} 9.02\ (1H) \\ 8.71\ (1H) \\ 8.68\ (1H) \\ 8.51\ (1H) \\ 8.18\ (1H) \\ 8.07\ (5H) \\ 7.94\ (1H) \\ 7.79 - 7.73\ (6H) \\ 7.64 - 7.57\ (4H) \\ 7.45\ (1H) \\ 7.35\ (4H) \end{array}$$

Example 7

Synthesis of a 2-{4-(pyridin-3-yl)phenyl}-4,6-bis([1,1':3',1"]terphenyl-5'-yl)-2H-benzotriazole (Synthesis of a Compound 30)

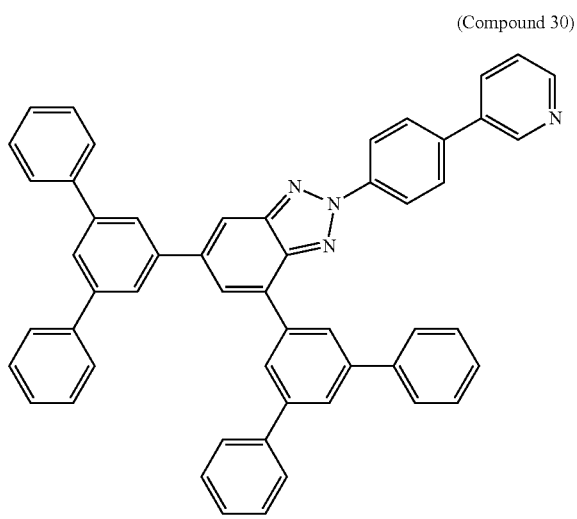 [SMILES: c1ccc(-c2cc(-c3ccccc3)cc(-c3cc(-c4cc(-c5ccccc5)cc(-c5ccccc5)c4)c4nn(-c5ccc(-c6cccnc6)cc5)nc4c3)c2)cc1]

(Compound 30)

| | |
|---|---|
| The 3-(4-nitrophenyl)pyridine synthesized in Example 1 | 10.0 g, |
| o-Phenylenediamine | 6.0 g, |
| Sodium hydroxide | 4.0 g, and |
| Toluene | 100 ml, | were put into the reaction vessel purged with nitrogen, and were heated and refluxed for 9.5 with stirring.

The organic layer was picked up by the separating operation, concentrated under a reduced pressure and was refined by the column chromatography to obtain 3.42 g of a brown powder of 2-{4-(pyridin-3-yl)phenylazo}phenylamine crystals (yield, 25.00).

3.4 Grams of the thus obtained phenylamine and 34 ml of chloroform were added to the reaction vessel purged with nitrogen, and to which a bromine solution obtained by dissolving 5.0 g of bromine in 34 ml of chloroform was added dropwise.

After stirred at room temperature for 3 hours, the reaction solution was washed with water, concentrated under a reduced pressure and was refined by the column chromatography to obtain 4.1 g of a red powder of 2,4-dibromo-6-{4-(pyridin-3-yl)phenylazo}phenylamine crystals (yield, 75.90).

| | |
|---|---|
| The above 2,4-dibromo-6-{4-(pyridin-3-yl)phenylazo}phenylamine | 4.0 g, |
| Iodobenzene diacetate | 4.5 g, and |
| Toluene | 40 ml, | were put into the reaction vessel purged with nitrogen, and were stirred at 74° C. for one hour. The organic layer was picked up by the separating operation, concentrated under a reduced pressure and was refined by the column chromatography to obtain 1.6 g of a white powder of 4,6-dibromo-2-{4-(pyridin-3-yl)phenyl}-2H-benzotriazole crystals (62.5%).

| | |
|---|---|
| The thus obtained 4,6-dibromo-2-{4-(pyridin-3-yl)phenyl}-2H-benzotriazole | 1.2 g, |
| (3,5-Diphenyl)phenylboronic acid | 1.7 g, |
| 2M Potassium carbonate aqueous solution | 4.3 ml, |
| Toluene | 10 ml, |
| Ethanol | 2 ml, and |
| Tetrakistriphenylphosphine palladium (0) | 0.3 g, | were put into the reaction vessel purged with nitrogen, and were heated and refluxed for 4.5 hours with stirring.

The organic layer was picked up by the separating operation, concentrated under a reduced pressure and was refined by the column chromatography to obtain 1.0 g of a yellow powder of 2-{4-(pyridin-3-yl)phenyl}-4,6-bis([1,1':3',1"]terphenyl-5'-yl)-2H-benzotriazole (compound 30) (yield, 50.0%).

Figure 7:
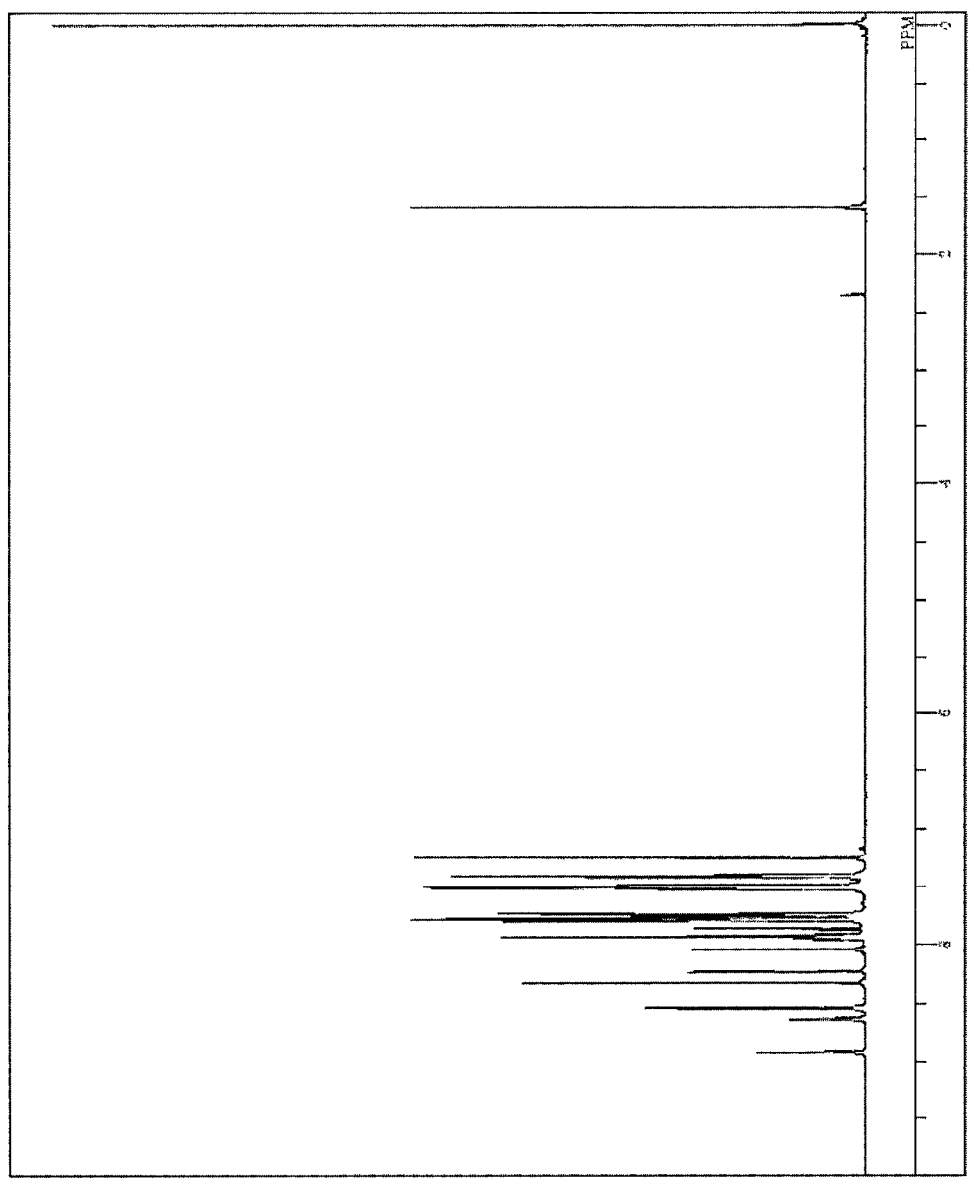
FIG. 7 is a ¹H-NMR chart of a compound (compound 30) of Example 7.

The obtained yellow powder was identified for its structure by the NMR. FIG. 7 shows the results of the $^1$H-NMR measurement.

The following 36 signals of hydrogen were detected by the $^1$H-NMR (CDCl$_3$).

δ(ppm) = 8.94 (1H)
8.65 (1H)
8.56 (2H)
8.34 (2H)
8.23 (1H)
8.05 (1H)
7.95 – 7.94 (3H)
7.92 (1H)
7.87 (1H)
7.80 – 7.74 (10H)
7.53 – 7.40 (13H)

Example 8

Synthesis of a 4,6-bis(biphenyl-4-yl)-2-{4-(pyridin-3-yl)phenyl}-2H-benzotriazole (Synthesis of a Compound 46)

(Compound 46)

| | |
|---|---|
| The 4,6-dibromo-2-{4-(pyridin-3-yl)phenyl}-2H-benzotriazole synthesized in Example 7 | 1.0 g, |
| 4-Biphenylboronic acid | 1.0 g, |
| 2M Potassium carbonate aqueous solution | 3.5 ml, |
| Toluene | 10 ml, |
| Ethanol | 2 ml, and |
| Tetrakistriphenylphosphine palladium (0) | 0.3 g, | were put into the reaction vessel purged with nitrogen, and were heated and refluxed for 4.5 hours with stirring.

The organic layer was picked up by the separating operation, concentrated under a reduced pressure and was refined by the column chromatography to obtain 0.6 g of a yellow powder of 4,6-bis(biphenyl-4-yl)-2-{4-(pyridin-3-yl)phenyl}-2H-benzotriazole (compound 46) (yield, 41.60).

Figure 8:
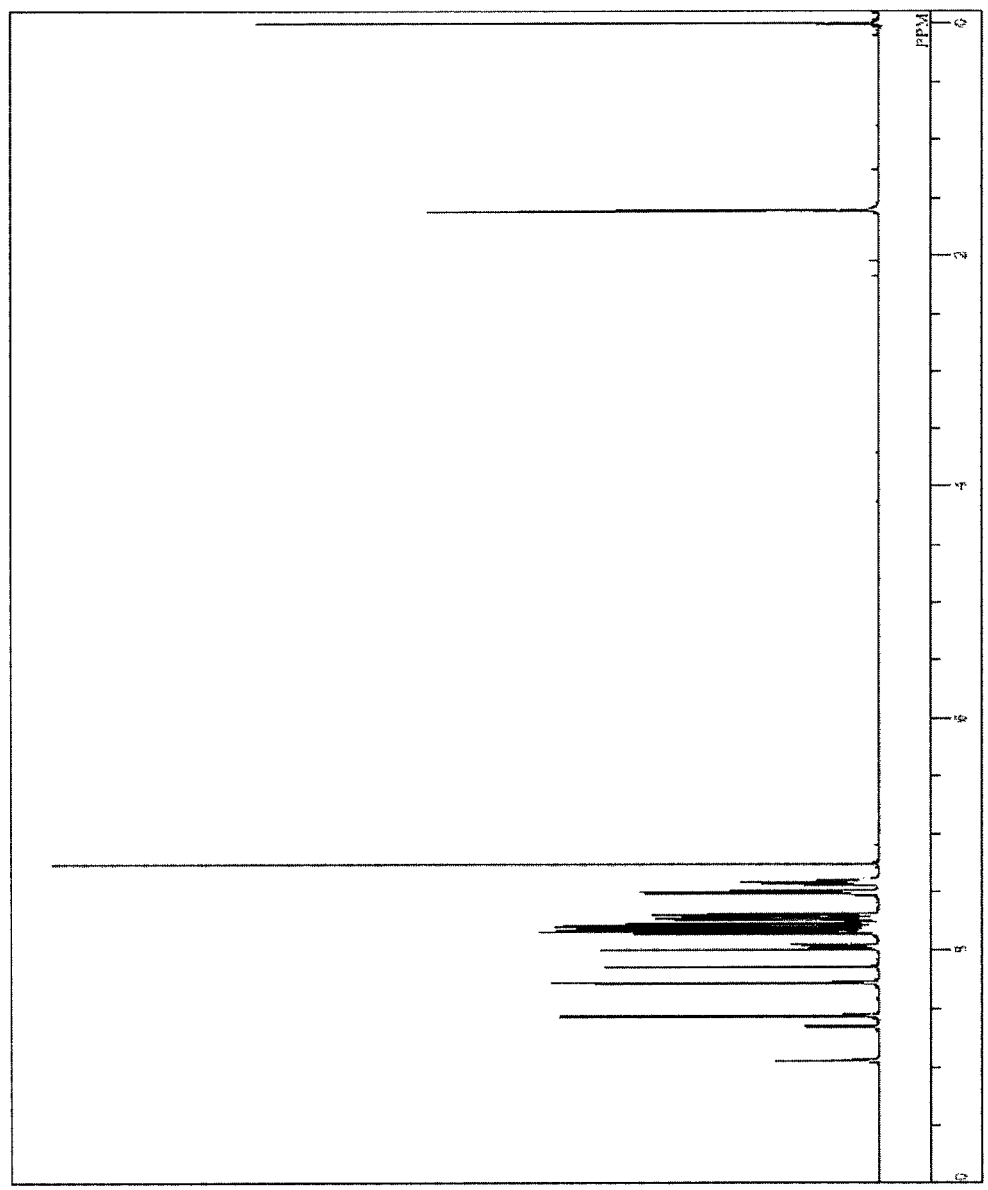
FIG. 8 is a ¹H-NMR chart of a compound (compound 46) of Example 8.

The obtained yellow powder was identified for its structure by the NMR. FIG. 8 shows the results of the $^1$H-NMR measurement.

The following 24 signals of hydrogen were detected by the $^1$H-NMR (CDCl$_3$).

δ(ppm) = 8.94 (1H)
8.65 (1H)
8.56 (2H)
8.28 (2H)
8.14 (1H)
7.98 (1H)
7.96 (1H)
7.86 – 7.68 (8H)
7.51 – 7.40 (7H)

Example 9

Synthesis of a 5-(9,10-diphenylanthracen-2-yl)-2-{4-(pyridin-3-yl)phenyl}-2H-benzotriazole (Synthesis of a Compound 106)

(Compound 106)

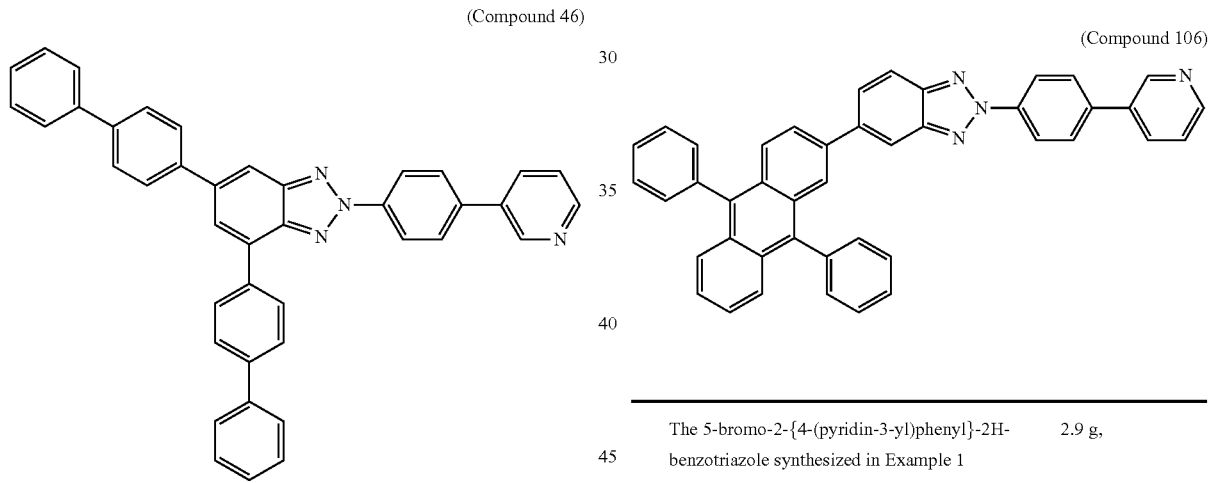

| | |
|---|---|
| The 5-bromo-2-{4-(pyridin-3-yl)phenyl}-2H-benzotriazole synthesized in Example 1 | 2.9 g, |
| 9,10-Diphenylanthracen-2-ylboronic acid | 3.7 g, |
| 2M Potassium carbonate aqueous solution | 12 ml, |
| Toluene | 30 ml, |
| Ethanol | 5.6 ml, and |
| Tetrakistriphenylphosphine palladium (0) | 0.4 g, | were put into the reaction vessel purged with nitrogen, and were heated and refluxed for 7.5 hours with stirring.

The organic layer was picked up by the separating operation, concentrated under a reduced pressure and was refined by the column chromatography to obtain 2.2 g of a faintly green powder of 5-(9,10-diphenylanthracen-2-yl)-2-{4-(pyridin-3-yl)phenyl}-2H-benzotriazole (compound 106) (yield, 43.84%).

Figure 9:
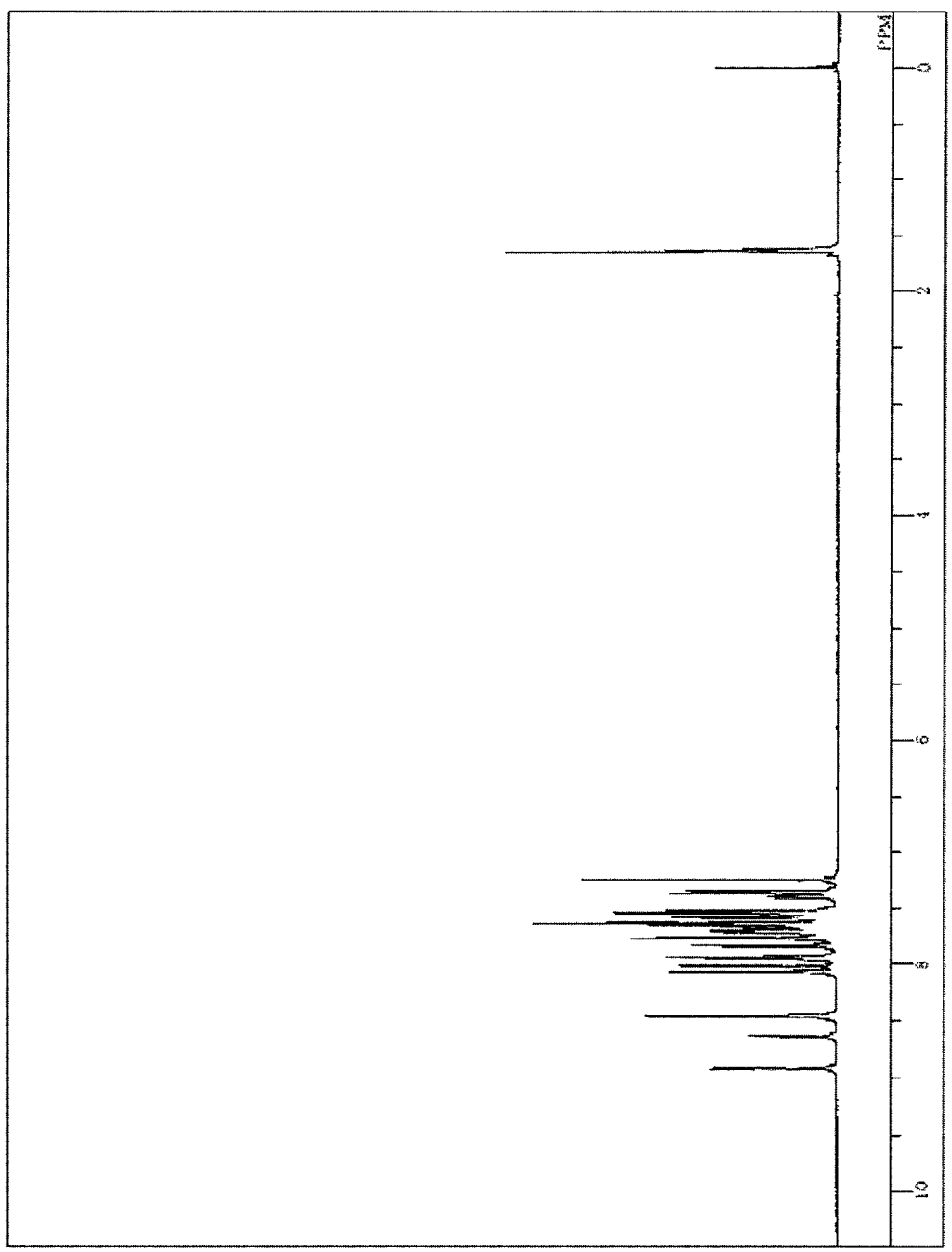
FIG. 9 is a ¹H-NMR chart of a compound (compound 106) of Example 9.

The obtained faintly green powder was identified for its structure by the NMR. FIG. 9 shows the results of the $^1$H-NMR measurement.

The following 28 signals of hydrogen were detected by the $^1$H-NMR (CDCl$_3$).

$\delta$(ppm) = 8.93 (1H)
8.64 (1H)
8.46 (2H)
8.07 (1H)
8.02 (1H)
7.94 (2H)
7.84 (1H)
7.76 (2H)
7.73 – 7.34 (17H)

Example 10

Synthesis of a 5-{9,10-di(naphthalen-2-yl)anthracen-2-yl}-2-{4-(pyridin-3-yl)phenyl}-2H-benzotriazole (synthesis of a compound 108)

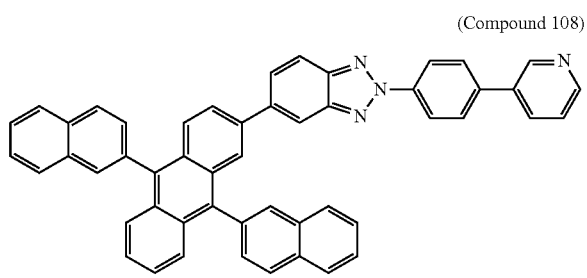 [SMILES: c1cncc(-c2ccc(-n3nc4ccc(-c5ccc6c(-c7ccc8ccccc8c7)c7ccccc7c(-c7ccc8ccccc8c7)c6c5)cc4n3)cc2)c1]

(Compound 108)

| | |
|---|---|
| The 5-bromo-2-{4-(pyridin-3-yl)phenyl}-2H-benzotriazole synthesized in Example 1 | 2.9 g, |
| 9,10-Di(naphthalen-2-yl)anthracen-2-ylboronic acid | 4.7 g, |
| 2M Potassium carbonate aqueous solution | 12 ml, |
| Toluene | 30 ml, |
| Ethanol | 5.6 ml, and |
| Tetrakistriphenylphosphine palladium (0) | 0.4 g, | were put into the reaction vessel purged with nitrogen, and were heated and refluxed for 7.5 hours with stirring.

The organic layer was picked up by the separating operation, concentrated under a reduced pressure and was refined by the column chromatography to obtain 2.4 g of a faintly green powder of 5-{9,10-di(naphthalen-2-yl)anthracen-2-yl}-2-{4-(pyridin-3-yl)phenyl}-2H-benzotriazole (compound 108) (yield, 41.330).

Figure 10:
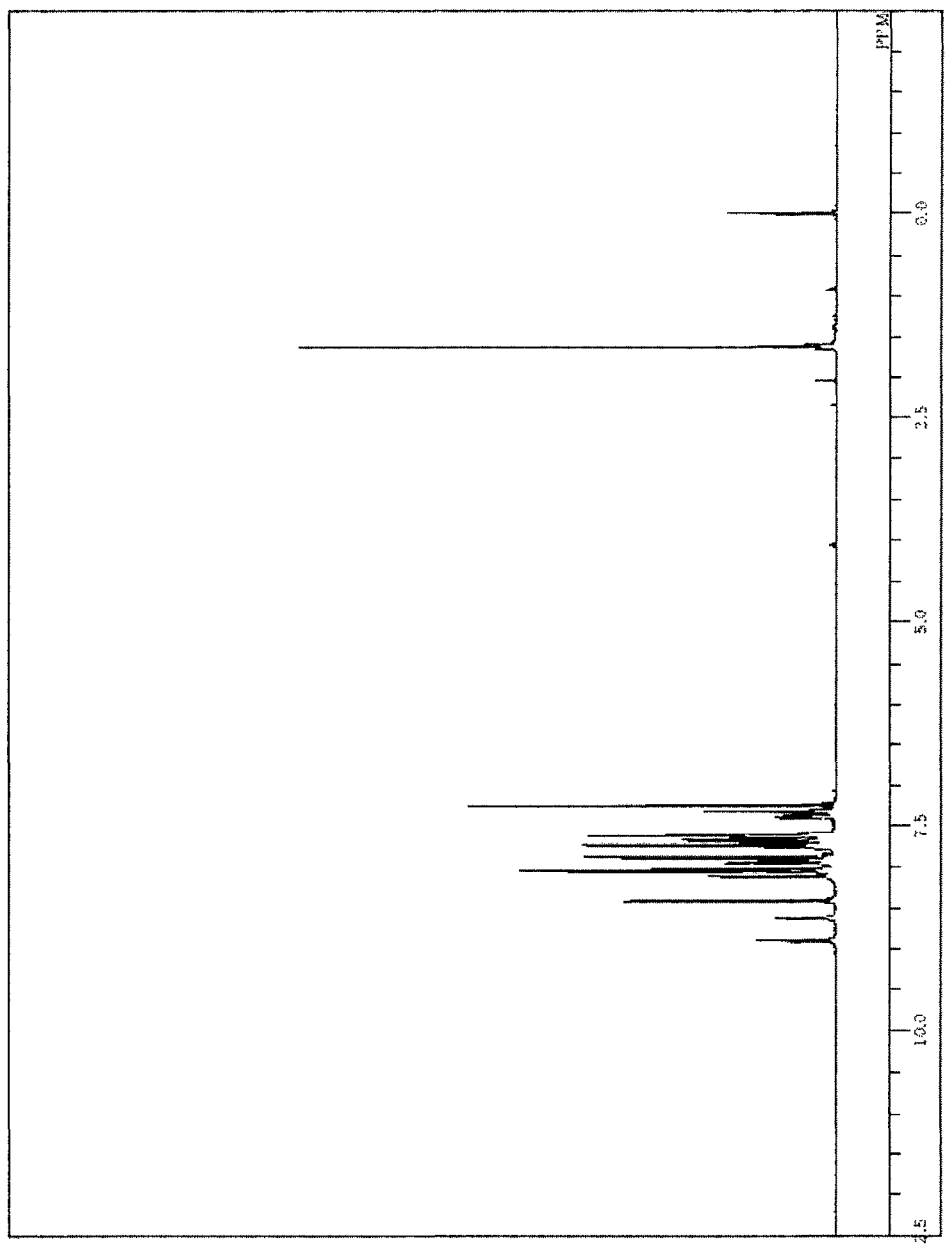
FIG. 10 is a ¹H-NMR chart of a compound (compound 108) of Example 10.

The obtained faintly green powder was identified for its structure by the NMR. FIG. 10 shows the results of the $^1$H-NMR measurement.

The following 28 signals of hydrogen were detected by the $^1$H-NMR (CDCl$_3$).

$\delta$(ppm) = 8.91 (1H)
8.63 (1H)
8.42 (2H)
8.13 (2H)
8.06 (5H)
8.03 (1H)
7.96 – 7.60 (17H)
7.40 (1H)
7.34 (2H)

Example 11

Synthesis of a 4,6-bis(9,9-dimethyl-9H-fluoren-2-yl)-2-{4-(pyridin-3-yl)phenyl}-2H-benzotriazole (Synthesis of a Compound 26)

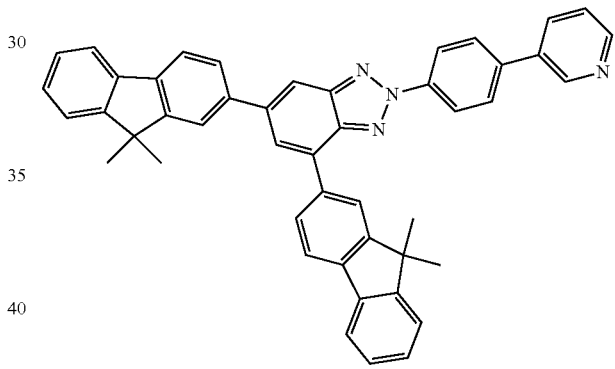

(Compound 26)

| | |
|---|---|
| The 4,6-dibromo-2-{4-(pyridin-3-yl)phenyl}-2H-benzotriazole synthesized in Example 7 | 1.5 g, |
| 9,9-Dimethyl-9H-fluoren-2-ylboronic acid | 2.8 g, |
| 2M Potassium carbonate aqueous solution | 5.3 ml, |
| Toluene | 30 ml, |
| Ethanol | 6 ml, and |
| Tetrakistriphenylphosphine palladium (0) | 0.1 g, | were put into the reaction vessel purged with nitrogen, and were heated and refluxed for 4.5 hours with stirring.

The organic layer was picked up by the separating operation, concentrated under a reduced pressure and was refined by the column chromatography to obtain 1.2 g of a yellow powder of 4,6-bis(9,9-dimethyl-9H-fluoren-2-yl)-2-{4-(pyridin-3-yl)phenyl}-2H-benzotriazole (compound 26) (yield, 51.2%).

Figure 11:
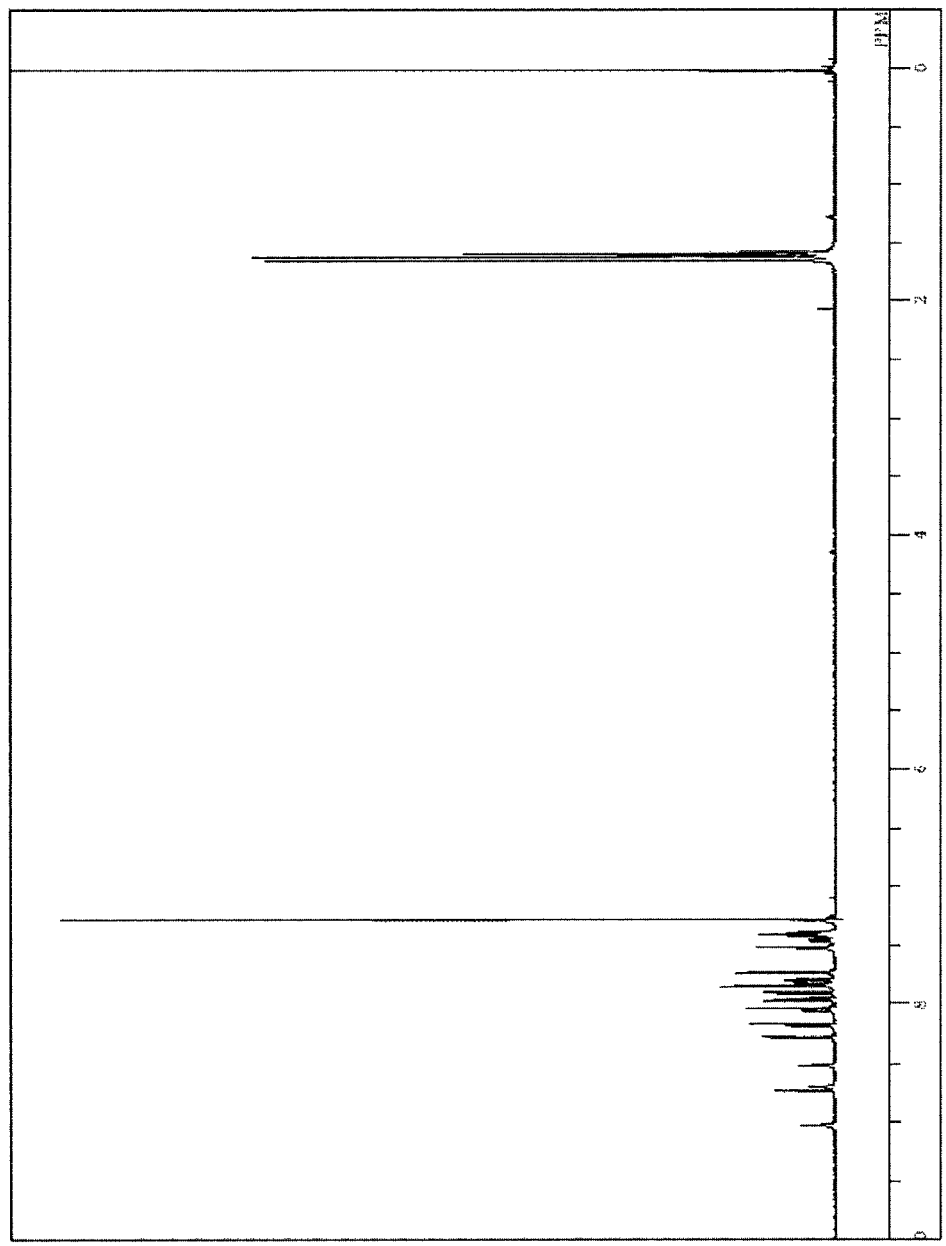
FIG. 11 is a ¹H-NMR chart of a compound (compound 26) of Example 11.

The obtained yellow powder was identified for its structure by the NMR. FIG. 11 shows the results of the $^1$H-NMR measurement.

The following 36 signals of hydrogen were detected by the $^1$H-NMR (CDCl$_3$).

δ(ppm) = 9.12 (1H)
8.74 (1H)
8.70 (1H)
8.53 (1H)
8.29 (1H)
8.18 (2H)
8.05 (2H)
7.95 (1H)
7.91 (1H)
7.83 – 7.79 (4H)
7.71 (2H)
7.52 (2H)
7.47 – 7.39 (5H)
1.55 (6H)
1.51 (6H)

Example 12

Synthesis of a 4,6-bis{4-(naphthalen-1-yl)phenyl}-2-{4-(pyridin-3-yl)phenyl}-2H-benzotriazole (Synthesis of a Compound 66)

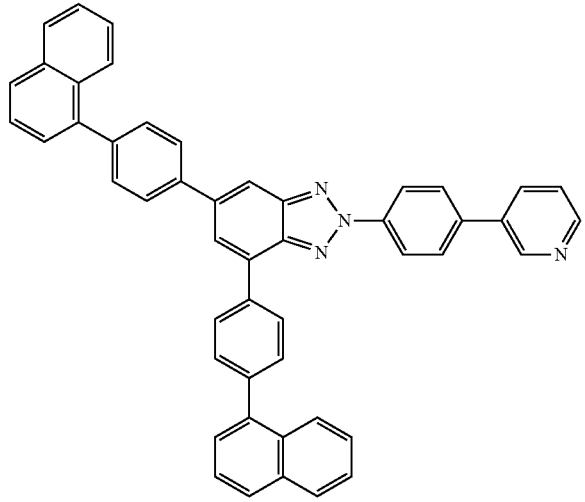

(Compound 66)

| | |
|---|---|
| The 4,6-dibromo-2-{4-(pyridin-3-yl)phenyl}-2H-benzotriazole synthesized in Example 7 | 1.5 g, |
| 4-(Naphthalen-1-yl)phenylboronic acid | 2.2 g, |
| 2M Potassium carbonate aqueous solution | 5.3 ml, |
| Toluene | 30 ml, |
| Ethanol | 6 ml, and |
| Tetrakistriphenylphosphine palladium (0) | 0.1 g, | were put into the reaction vessel purged with nitrogen, and were heated and refluxed for 4.5 hours with stirring.

The organic layer was picked up by the separating operation, concentrated under a reduced pressure and was refined by the column chromatography to obtain 2.0 g of a yellow powder of 4,6-bis{4-(naphthalen-1-yl)phenyl}-2-{4-(pyridin-3-yl)phenyl}-2H-benzotriazole (compound 66) (yield, 84.2%).

Figure 12:
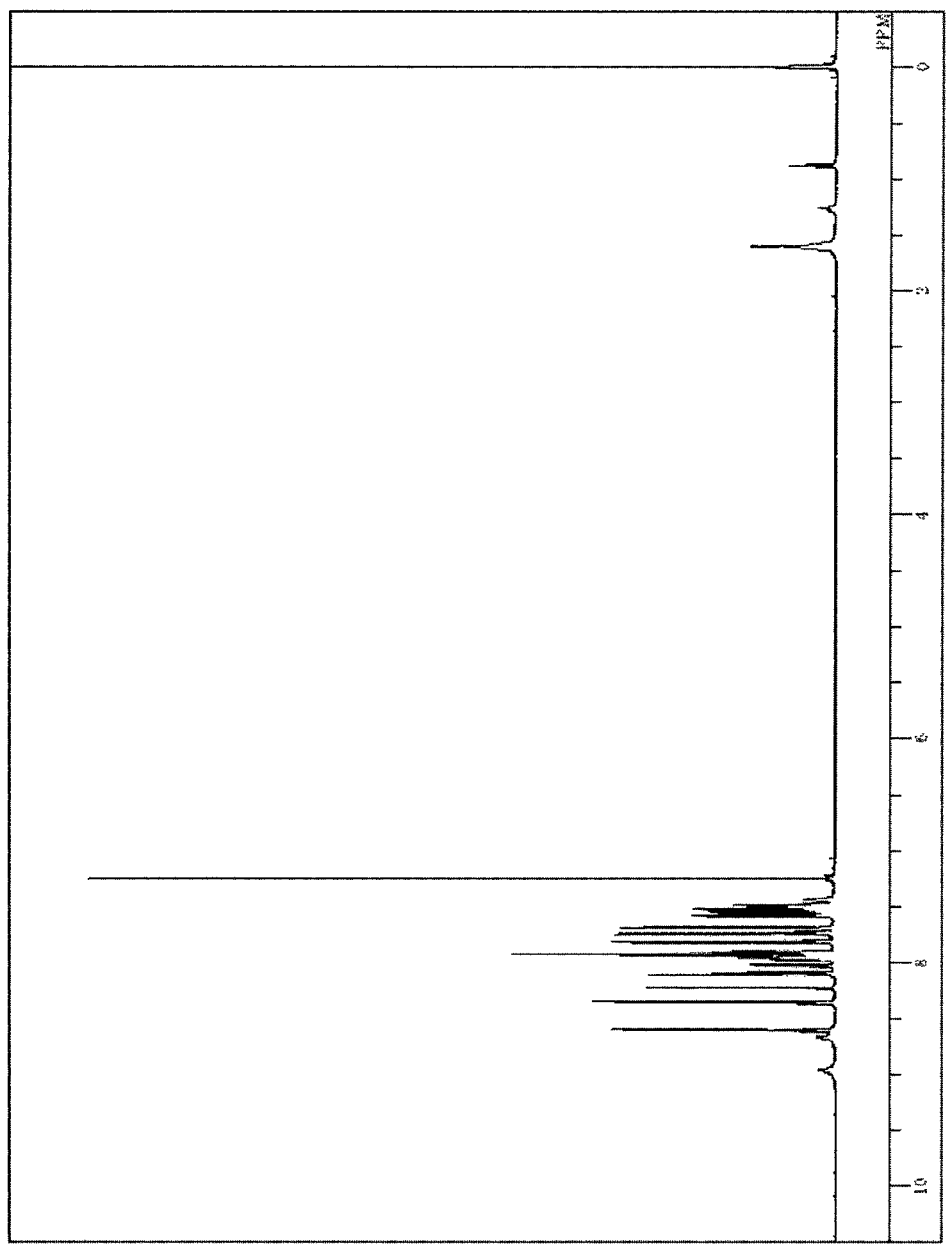
FIG. 12 is a ¹H-NMR chart of a compound (compound 66) of Example 12.

The obtained yellow powder was identified for its structure by the NMR. FIG. 12 shows the results of the $^1$H-NMR measurement.

The following 32 signals of hydrogen were detected by the $^1$H-NMR (CDCl$_3$).

δ(ppm) = 8.62 (1H)
8.61 (1H)
8.36 (2H)
8.22 (1H)
8.11 (1H)
8.08 (1H)
8.02 (1H)
7.96 – 7.83 (8H)
7.81 (2H)
7.75 (2H)
7.68 (2H)
7.59 – 7.49 (10H)

Example 13

Synthesis of a 4,6-bis{4-(naphthalen-2-yl)phenyl}-2-{4-(pyridin-3-yl)phenyl}-2H-benzotriazole (Synthesis of a Compound 62)

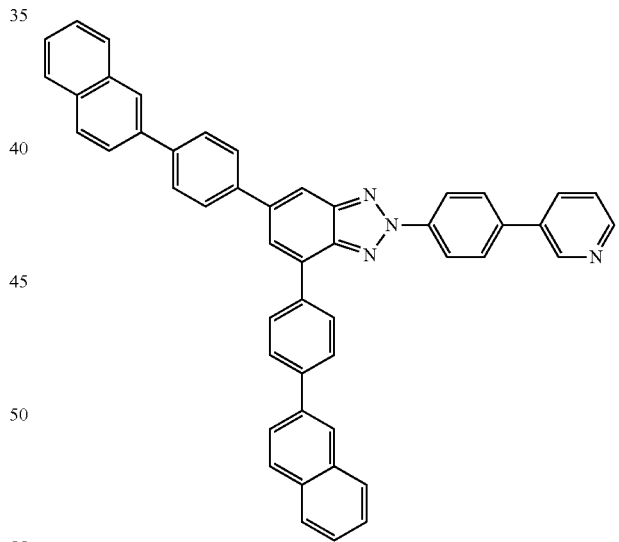

(Compound 62)

| | |
|---|---|
| The 4,6-dibromo-2-{4-(pyridin-3-yl)phenyl}-2H-benzotriazole synthesized in Example 7 | 1.5 g, |
| 4-(Naphthalen-2-yl)phenylboronic acid | 2.2 g, |
| 2M Potassium carbonate aqueous solution | 5.3 ml, |
| Toluene | 30 ml, |
| Ethanol | 6 ml, and |
| Tetrakistriphenylphosphine palladium (0) | 0.1 g, | were put into the reaction vessel purged with nitrogen, and were heated and refluxed for 4.5 hours with stirring.

The organic layer was picked up by the separating operation, concentrated under a reduced pressure and was refined by the column chromatography to obtain 1.2 g of a yellow powder of 4,6-bis{4-(naphthalen-2-yl)phenyl}-2-{4-(pyridin-3-yl)phenyl}-2H-benzotriazole (compound 62) (yield, 44.2%).

Figure 13:
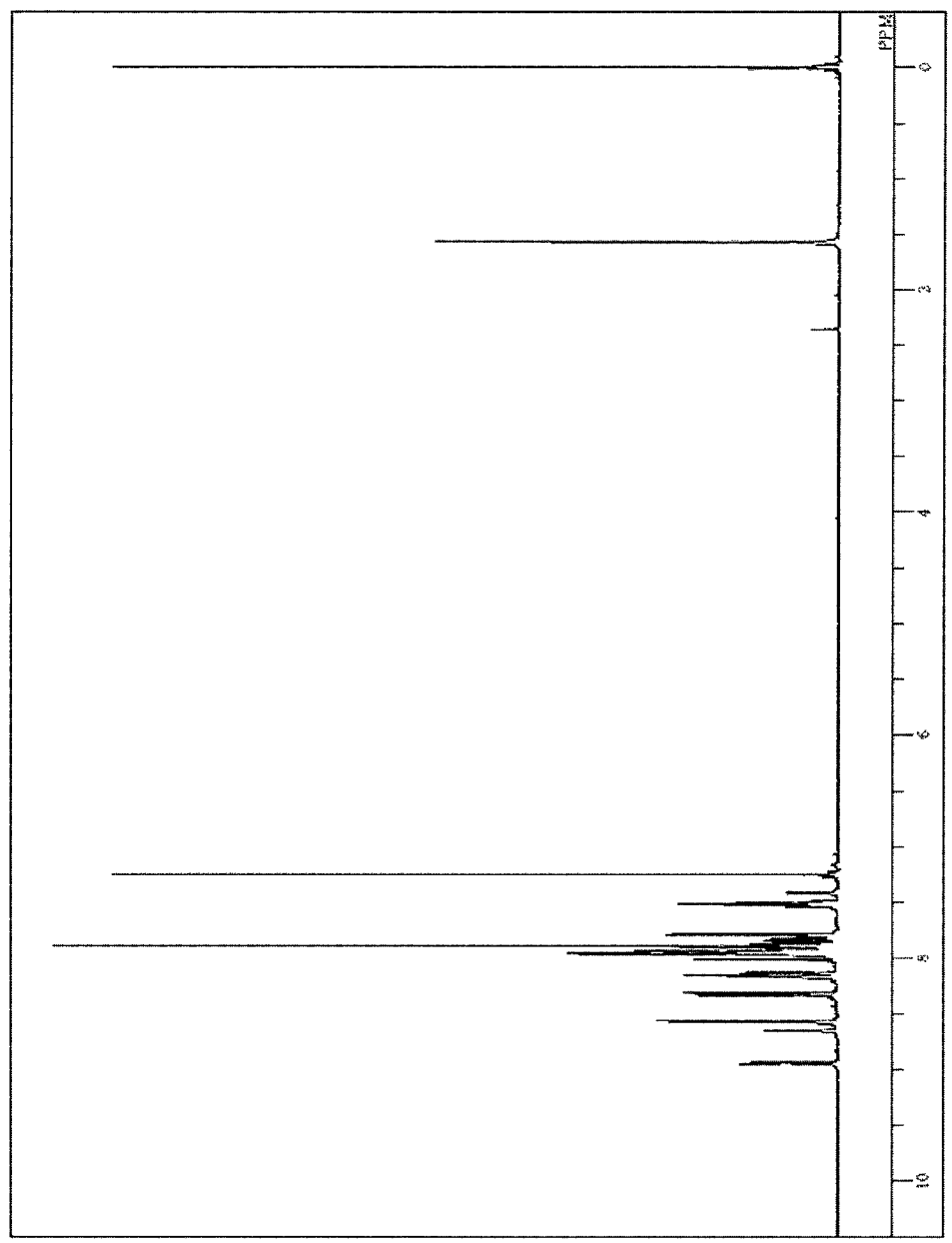
FIG. 13 is a ¹H-NMR chart of a compound (compound 62) of Example 13.

The obtained yellow powder was identified for its structure by the NMR. FIG. 13 shows the results of the $^1$H-NMR measurement.

The following 32 signals of hydrogen were detected by the $^1$H-NMR (CDCl$_3$).

δ(ppm) = 8.95 (1H)
8.66 (1H)
8.57 (2H)
8.33 (2H)
8.17 (2H)
8.13 (1H)
7.98 – 7.88 (14H)
7.80 (2H)
7.75 (2H)
7.54 (4H)
7.43 (1H)

Example 14

Synthesis of a 4,6-bis(4-phenyl-naphthalen-1-yl)-2-{4-(pyridin-3-yl)phenyl}-2H-benzotriazole (Synthesis of a Compound 54)

(Compound 54)

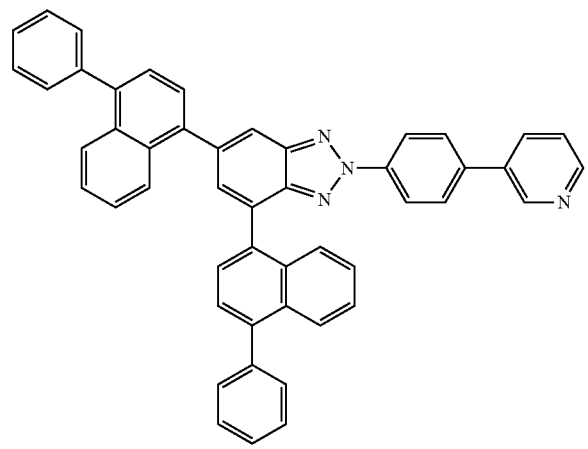

| | |
|---|---|
| The 4,6-dibromo-2-{4-(pyridin-3-yl)phenyl}-2H-benzotriazole synthesized in Example 7 | 1.5 g, |
| 4-Phenyl-naphthalen-1-ylboronic acid | 2.2 g, |
| 2M Potassium carbonate aqueous solution | 5.3 ml, |
| Toluene | 30 ml, |
| Ethanol | 6 ml, and |
| Tetrakistriphenylphosphine palladium (0) | 0.1 g, | were put into the reaction vessel purged with nitrogen, and were heated and refluxed for 4.5 hours with stirring.

The organic layer was picked up by the separating operation, concentrated under a reduced pressure and was refined by the column chromatography to obtain 1.5 g of a yellow powder of 4,6-bis(4-phenyl-naphthalen-1-yl)-2-{4-(pyridin-3-yl)phenyl}-2H-benzotriazole (compound 54) (yield, 62.0%).

Figure 14:
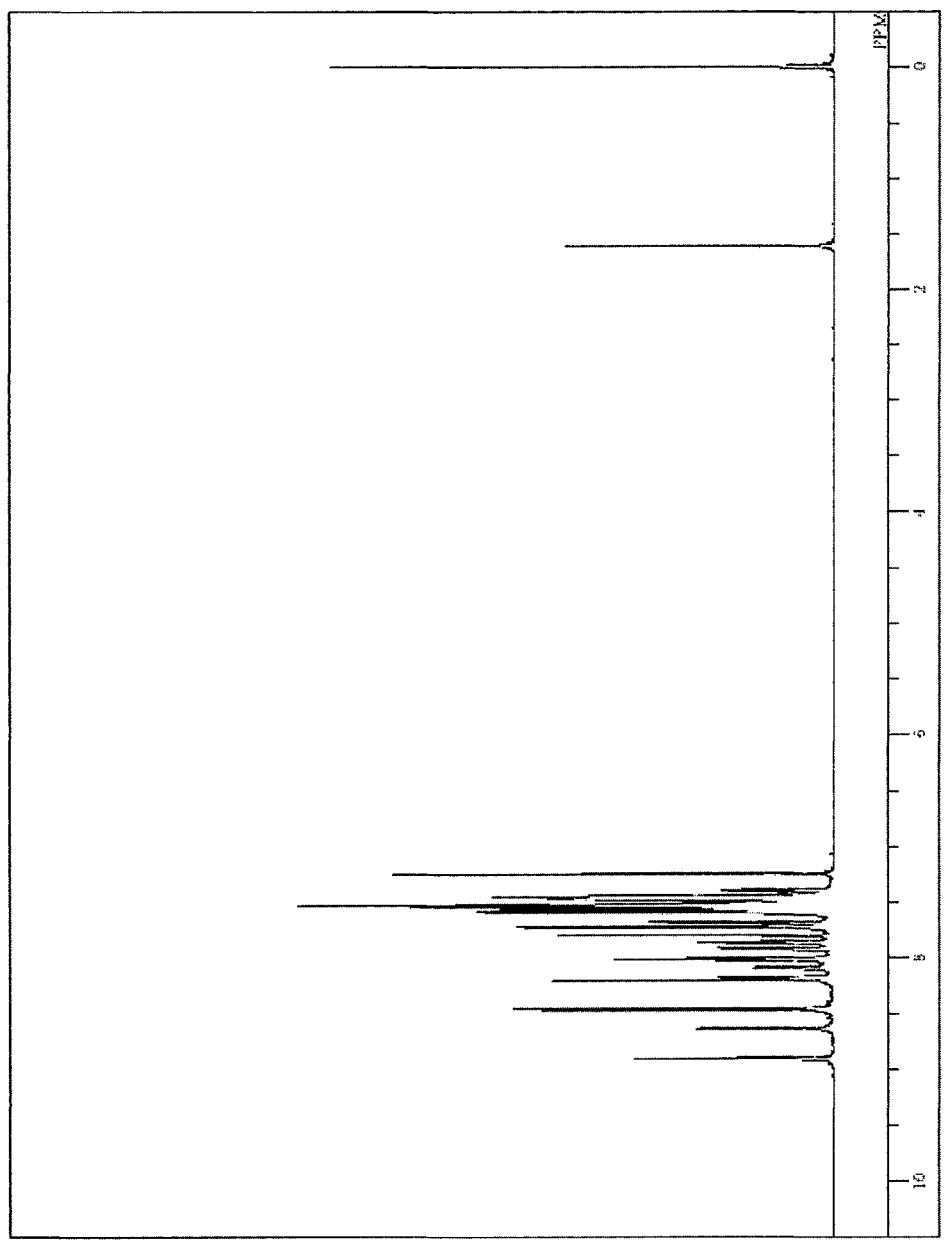
FIG. 14 is a ¹H-NMR chart of a compound (compound 54) of Example 14.

The obtained yellow powder was identified for its structure by the NMR. FIG. 14 shows the results of the $^1$H-NMR measurement.

The following 32 signals of hydrogen were detected by the $^1$H-NMR (CDCl$_3$).

δ(ppm) = 8.90 (1H)
8.64 (1H)
8.47 (2H)
8.20 (1H)
8.17 (1H)
8.09 (1H)
8.02 (3H)
7.91 (1H)
7.81 (1H)
7.73 (2H)
7.69 (1H)
7.61 – 7.41 (16H)

Example 15

Synthesis of a 4,6-bis(4-phenanthren-9-yl)-2-{4-(pyridin-3-yl)phenyl}-2H-benzotriazole (Synthesis of a Compound 110)

(Chemical 110)

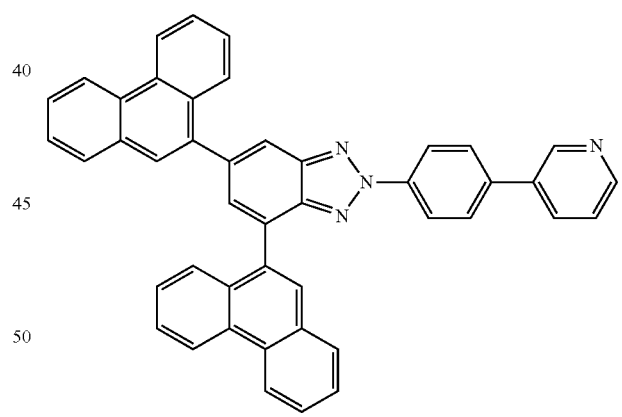

| | |
|---|---|
| The 4,6-dibromo-2-{4-(pyridin-3-yl)phenyl}-2H-benzotriazole synthesized in Example 7 | 2.0 g, |
| Phenanthren-9-ylboronic acid | 3.5 g, |
| 2M Potassium carbonate aqueous solution | 6 ml, |
| Toluene | 20 ml, |
| Ethanol | 4 ml, and |
| Tetrakistriphenylphosphine palladium (0) | 0.1 g, | were put into the reaction vessel purged with nitrogen, and were heated and refluxed for 4.5 hours with stirring.

The organic layer was picked up by the separating operation, concentrated under a reduced pressure and was refined by the column chromatography to obtain 2.1 g of a yellow powder of 4,6-bis(phenanthren-9-yl)-2-{4-(pyridin-3-yl)phenyl}-2H-benzotriazole (compound 110) (yield, 72.3%).

Figure 15:
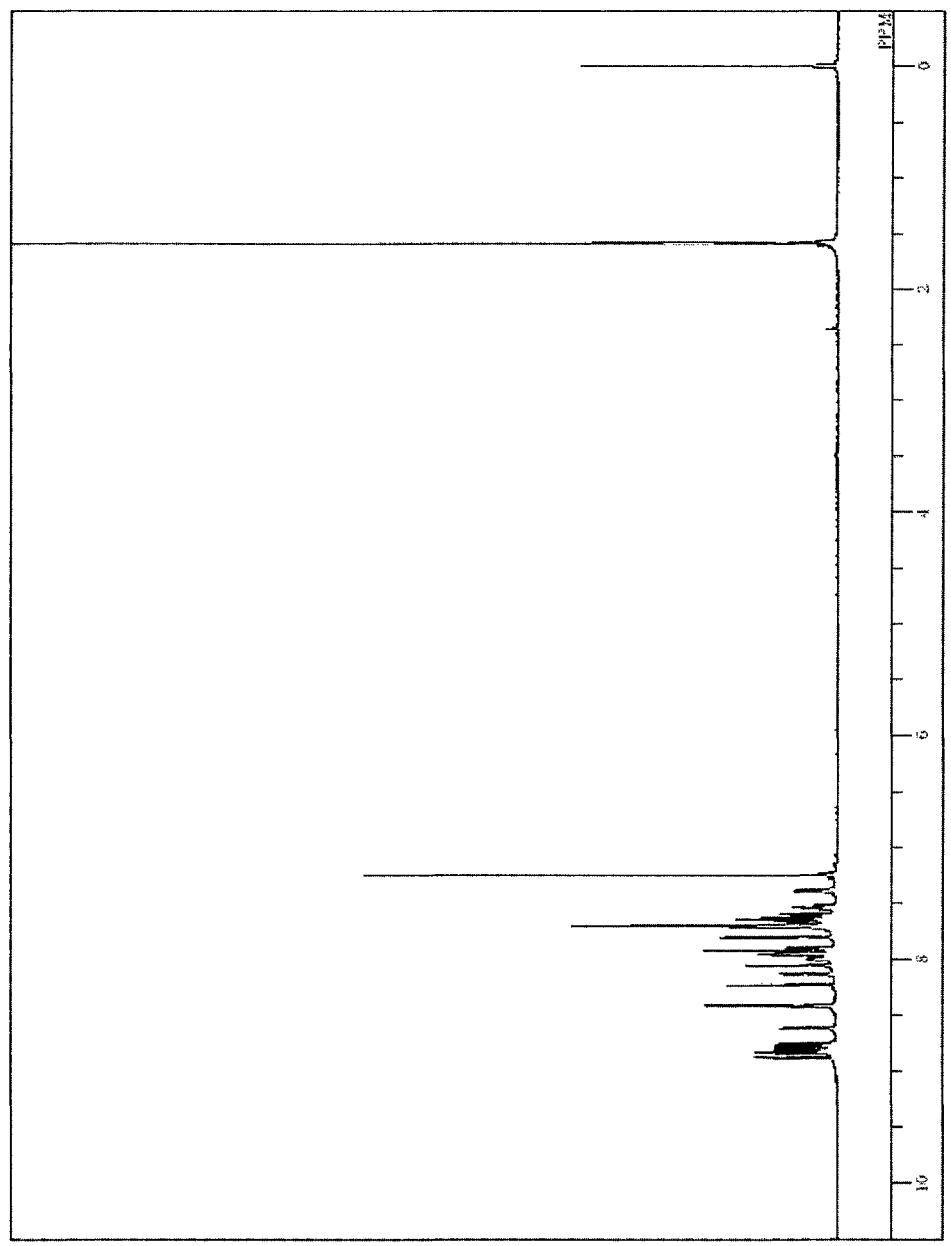
FIG. 15 is a ¹H-NMR chart of a compound (compound 110) of Example 15.

The obtained yellow powder was identified for its structure by the NMR. FIG. 15 shows the results of the $^1$H-NMR measurement.

The following 28 signals of hydrogen were detected by the $^1$H-NMR (CDCl$_3$).

δ(ppm) = 8.88 (1H)
8.81 (1H)
8.76 (2H)
8.62 (1H)
8.43 (2H)
8.23 (1H)
8.14 (1H)
8.06 (1H)
7.96 – 7.92 (4H)
7.84 (1H)
7.71 – 7.76 (9H)
7.73 (2H)
7.54 (1H)
7.26 (1H)

Example 16

Synthesis of a 4,6-bis(9-phenyl-9H-carbazol-3-yl)-2-{4-(pyridin-3-yl)phenyl}-2H-benzotriazole (Synthesis of a Compound 112)

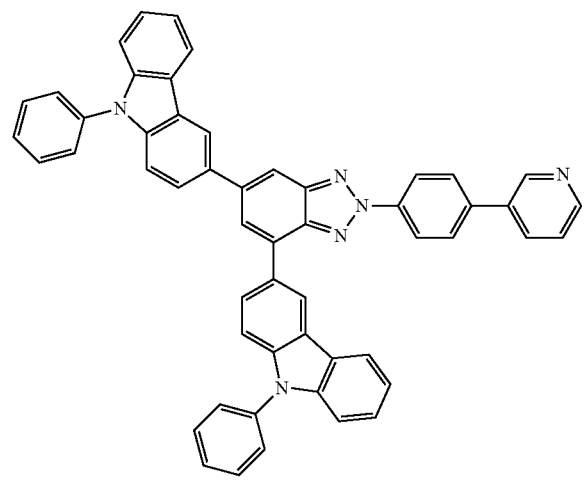

(Compound 112)

| | |
|---|---|
| The 4,6-dibromo-2-{4-(pyridin-3-yl)phenyl}-2H-benzotriazole synthesized in Example 7 | 2.5 g, |
| 9-Phenyl-9H-carbazol-3-ylboronic acid | 4.5 g, |
| 2M Potassium carbonate aqueous solution | 25.0 ml, |
| Toluene | 20 ml, |
| Ethanol | 5 ml, and |
| Tetrakistriphenylphosphine palladium (0) | 0.1 g, | were put into the reaction vessel purged with nitrogen, and were heated and refluxed for 4.5 hours with stirring.

The organic layer was picked up by the separating operation, concentrated under a reduced pressure and was refined by the column chromatography to obtain 3.7 g of a yellow powder of 4,6-bis(9-phenyl-9H-carbazol-3-yl)-2-{4-(pyridin-3-yl)phenyl}-2H-benzotriazole (compound 112) (yield, 83.4%).

Figure 16:
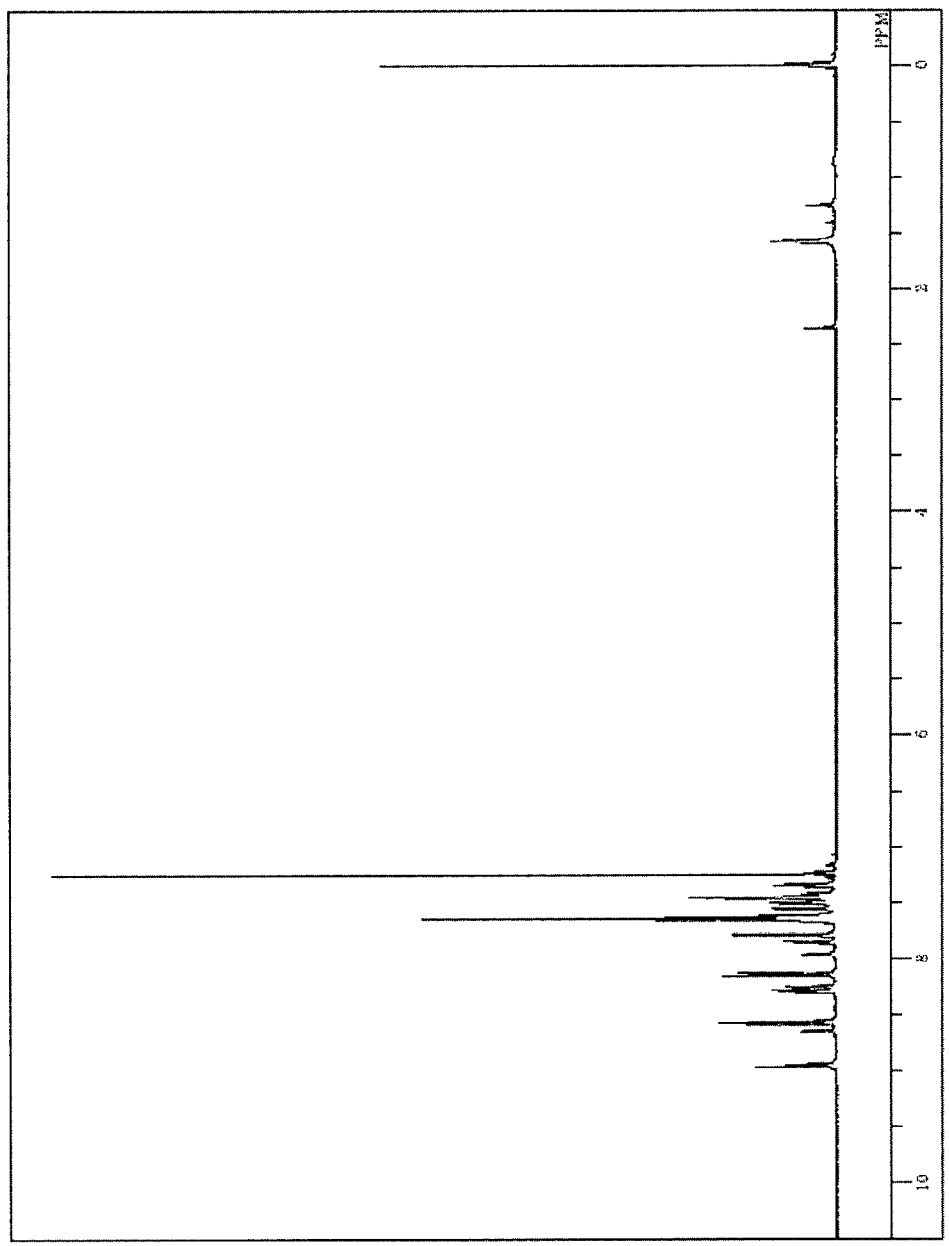
FIG. 16 is a ¹H-NMR chart of a compound (compound 112) of Example 16.

The obtained yellow powder was identified for its structure by the NMR. FIG. 16 shows the results of the $^1$H-NMR measurement.

The following 34 signals of hydrogen were detected by the $^1$H-NMR (CDCl$_3$).

δ(ppm) = 8.96 (2H)
8.66 (1H)
8.60 – 8.56 (3H)
8.30 (2H)
8.26 (1H)
8.16 (2H)
7.97 (1H)
7.87 (1H)
7.80 (2H)
7.64 (8H)
7.57 (1H)
7.52 (2H)
7.45 (6H)
7.35 (2H)

Example 17

Synthesis of a 5-[10-{3-(naphthalen-1-yl)phenyl}anthracen-9-yl]-2-{4-(pyridin-3-yl)phenyl}-2H-benzotriazole (Synthesis of a Compound 18)

(Compound 18)

| | |
|---|---|
| The 5-bromo-2-{4-(pyridin-3-yl)phenyl}-2H-benzotriazole synthesized in Example 1 | 3.5 g, |
| 10-{3-(naphthalen-1-yl)anthracen-9-ylboronic acid | 3.7 g, |
| 2M Potassium carbonate aqueous solution | 12 ml, |
| Toluene | 26 ml, |
| Ethanol | 7 ml, and |
| Tetrakistriphenylphosphine palladium (0) | 0.5 g, | were put into the reaction vessel purged with nitrogen, and were heated and refluxed for 8.5 hours with stirring.

The organic layer was picked up by the separating operation, concentrated under a reduced pressure and was refined by the column chromatography to obtain 2.8 g of a yellow powder of 5-[10-{3-(naphthalen-1-yl)phenyl}anthracen-9-yl]-2-{4-(pyridin-3-yl)phenyl}-2H-benzotriazole (compound 18) (yield, 53.40).

Figure 17:
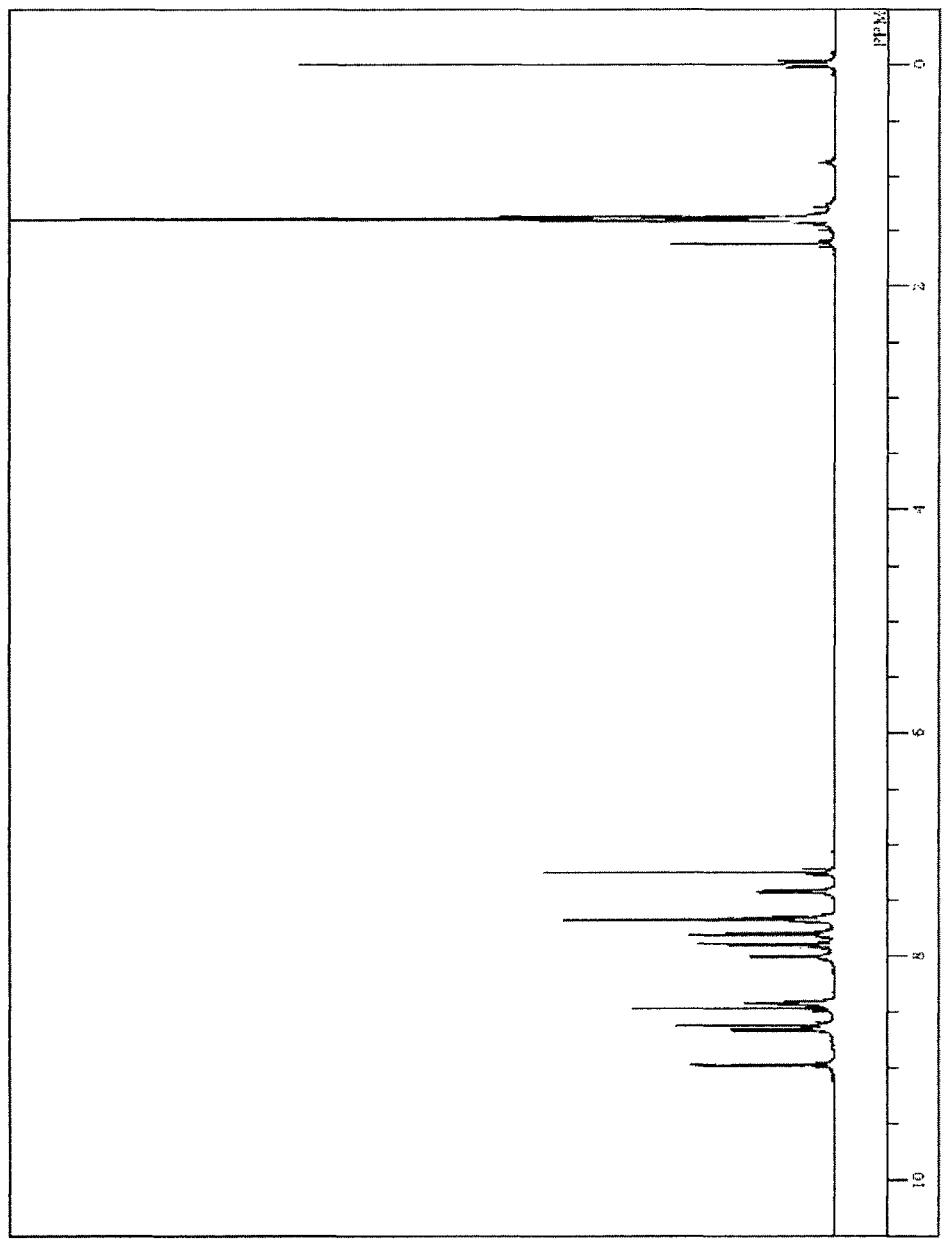
FIG. 17 is a ¹H-NMR chart of a compound (compound 18) of Example 17.

The obtained yellow powder was identified for its structure by the NMR. FIG. 17 shows the results of the ¹H-NMR measurement.

The following 30 signals of hydrogen were detected by the ¹H-NMR (CDCl₃).

$\delta$(ppm) = 8.97 (1H)
8.67 (1H)
8.57 (2H)
8.17 – 8.08 (3H)
7.98 – 7.68 (12H)
7.60 – 7.49 (5H)
7.40 (4H)
7.26 (2H)

Example 18

Synthesis of a 5-{4-(10-phenylanthracen-9-yl)phenyl)-2-{4-(pyridin-3-yl)phenyl}-2H-benzotriazole (Synthesis of a Compound 82)

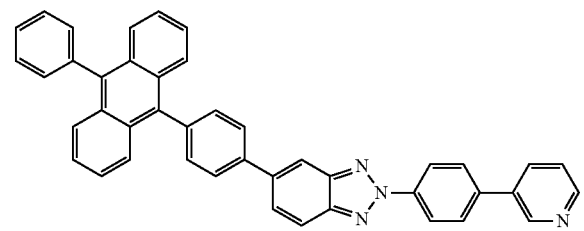
(Compound 82)

| | |
|---|---|
| The 5-bromo-2-{4-(pyridin-3-yl)phenyl}-2H-benzotriazole synthesized in Example 1 | 1.6 g, |
| 4-(10-Phenylanthracen-9-yl)phenylboronic acid | 1.6 g, |
| 2M Potassium carbonate aqueous solution | 6 ml, |
| Toluene | 16 ml, |
| Ethanol | 4 ml, and |
| Tetrakistriphenylphosphine palladium (0) | 0.2 g, | were put into the reaction vessel purged with nitrogen, and were heated and refluxed for 8.5 hours with stirring.

The organic layer was picked up by the separating operation, concentrated under a reduced pressure and was refined by the column chromatography to obtain 1.0 g of a yellow powder of 5-{4-(10-phenylanthracen-9-yl)phenyl}-2-{4-(pyridin-3-yl)phenyl}-2H-benzotriazole (compound 82) (yield, 40.0%).

Figure 18:
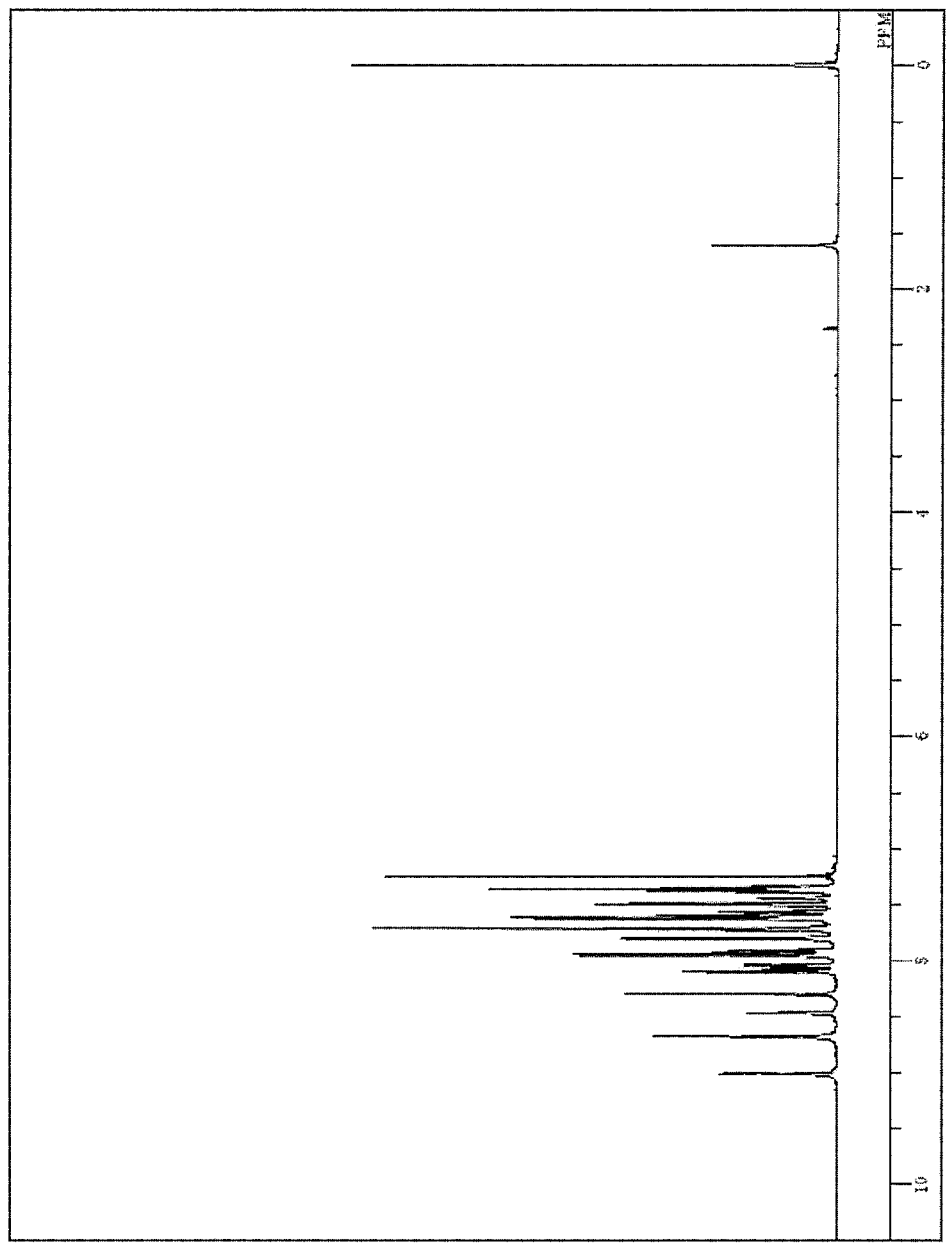
FIG. 18 is a ¹H-NMR chart of a compound (compound 82) of Example 18.

The obtained yellow powder was identified for its structure by the NMR. FIG. 18 shows the results of the ¹H-NMR measurement.

The following 28 signals of hydrogen were detected by the ¹H-NMR (CDCl₃).

$\delta$(ppm) = 9.01 (1H)
8.69 (2H)
8.48 (1H)
8.30 (1H)
8.11 (1H)
8.05 (1H)
7.95 (2H)
7.91 (1H)
7.81 (2H)
7.73 – 7.44 (8H)
7.51 (3H)
7.45 (1H)
7.37 (4H)

Example 19

Synthesis of a 4,6-bis(phenanthren-2-yl)-2-{4-(pyridin-3-yl)phenyl}-2H-benzotriazole (Synthesis of a Compound 111)

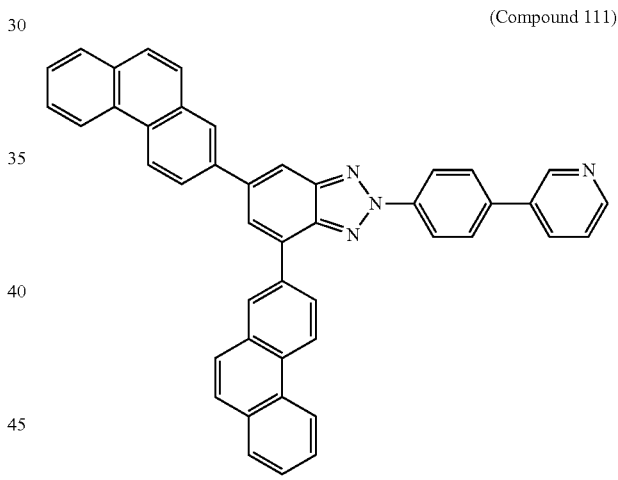
(Compound 111)

| | |
|---|---|
| The 4,6-dibromo-2-{4-(pyridin-3-yl)phenyl}-2H-benzotriazole synthesized in Example 7 | 2.8 g, |
| Phenanthren-9-ylboronic acid | 4.9 g, |
| 2M Potassium carbonate aqueous solution | 10 ml, |
| Toluene | 24 ml, |
| Ethanol | 6 ml, and |
| Tetrakistriphenylphosphine palladium (0) | 0.4 g, | were put into the reaction vessel purged with nitrogen, and were heated and refluxed for 4.5 hours with stirring.

The organic layer was picked up by the separating operation, concentrated under a reduced pressure and was refined by the column chromatography to obtain 1.0 g of a yellow powder of 4,6-bis(phenanthren-2-yl)-2-{4-(pyridin-3-yl)phenyl}-2H-benzotriazole (compound 111) (yield, 24.5%).

Figure 19:
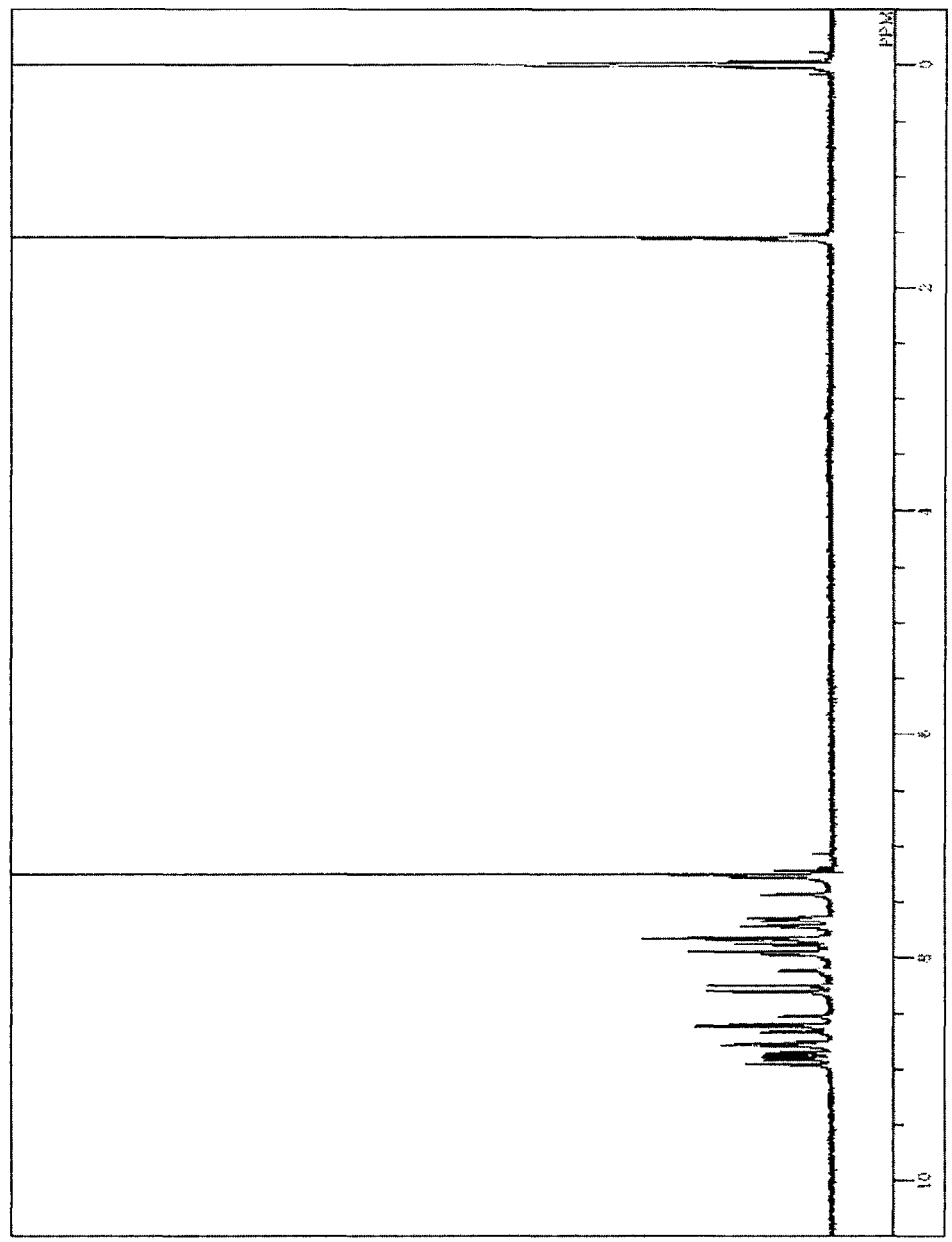
FIG. 19 is a ¹H-NMR chart of a compound (compound 111) of Example 19.

The obtained yellow powder was identified for its structure by the NMR. FIG. 19 shows the results of the ¹H-NMR measurement.

The following 28 signals of hydrogen were detected by the ¹H-NMR (CDCl₃).

δ(ppm) = 8.96 (1H)
8.91 (1H)
8.87 (1H)
8.79 (3H)
8.67 (1H)
8.62 (2H)
8.54 (1H)
8.31 (2H)
8.25 (1H)
8.13 (1H)
7.95 (4H)
7.89 (1H)
7.84 (3H)
7.73 (2H)
7.66 (2H)
7.45 (2H)

Example 20

Synthesis of a 5-{10-(quinolin-3-yl)anthracen-9-yl}]-2-{4-(pyridin-3-yl)phenyl}-2H-benzotriazole (Synthesis of a Compound 113)

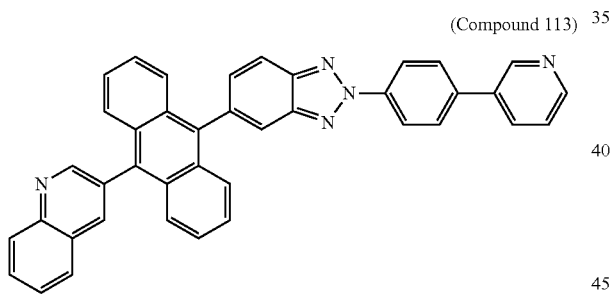

(Compound 113)

| | |
|---|---|
| The 5-bromo-2-{4-(pyridin-3-yl)phenyl}-2H-benzotriazole synthesized in Example 1 | 7.0 g, |
| Bispinacolatodiboron | 6.58 g, |
| {1,1'-Bis(diphenylphosphino)ferrocene} palladium dichloride | 0.33 g, |
| Potassium acetate | 5.87 g, and |
| Dioxane | 70 ml, | were put into the reaction vessel purged with nitrogen, and were heated at 85° C. for 5 hours with stirring. The reaction solution was cooled down to room temperature and to which water was added. Thereafter, the organic layer was picked up by using toluene.

The organic layer was concentrated under a reduced pressure and was refined by the column chromatography to obtain 6.4 g of a yellow powder of 2-{4-(pyridin-3-yl)phenyl}-5-(4,4,5,5-tetramethyl-[1,3,2]dioxaboran-2-yl)-2H-benzotriazole (yield 80.60).

| | |
|---|---|
| The above 2-{4-(pyridin-3-yl)phenyl}-5-(4,4,5,5-tetramethyl-[1,3,2]dioxaboran-2-yl)-2H-benzotriazole | 1.4 g, |
| 3-(10-Bromoanthracen-9-yl)quinoline | 1.2 g, |
| 2M Potassium carbonate aqueous solution | 5 ml, |
| Toluene | 12 ml, |
| Ethanol | 3 ml, and |
| Tetrakistriphenylphosphine palladium (0) | 0.4 g, | were put into the reaction vessel purged with nitrogen, and were heated and refluxed at 70° C. for 15.5 hours with stirring. The organic solvent was distilled off, chloroform and water were added thereto, and the organic layer was picked up by the separating operation.

The organic layer was concentrated under a reduced pressure, dissolved in toluene, refined by the adsorption by using NH silica gel, and was, thereafter, refined by the column chromatography to obtain 0.6 g of a yellow powder of 5-{10-(quinolin-3-yl)anthracen-9-yl}-2-{4-(pyridin-3-yl)phenyl}-2H-benzotriazole (compound 113) (yield, 61.0%).

Figure 20:
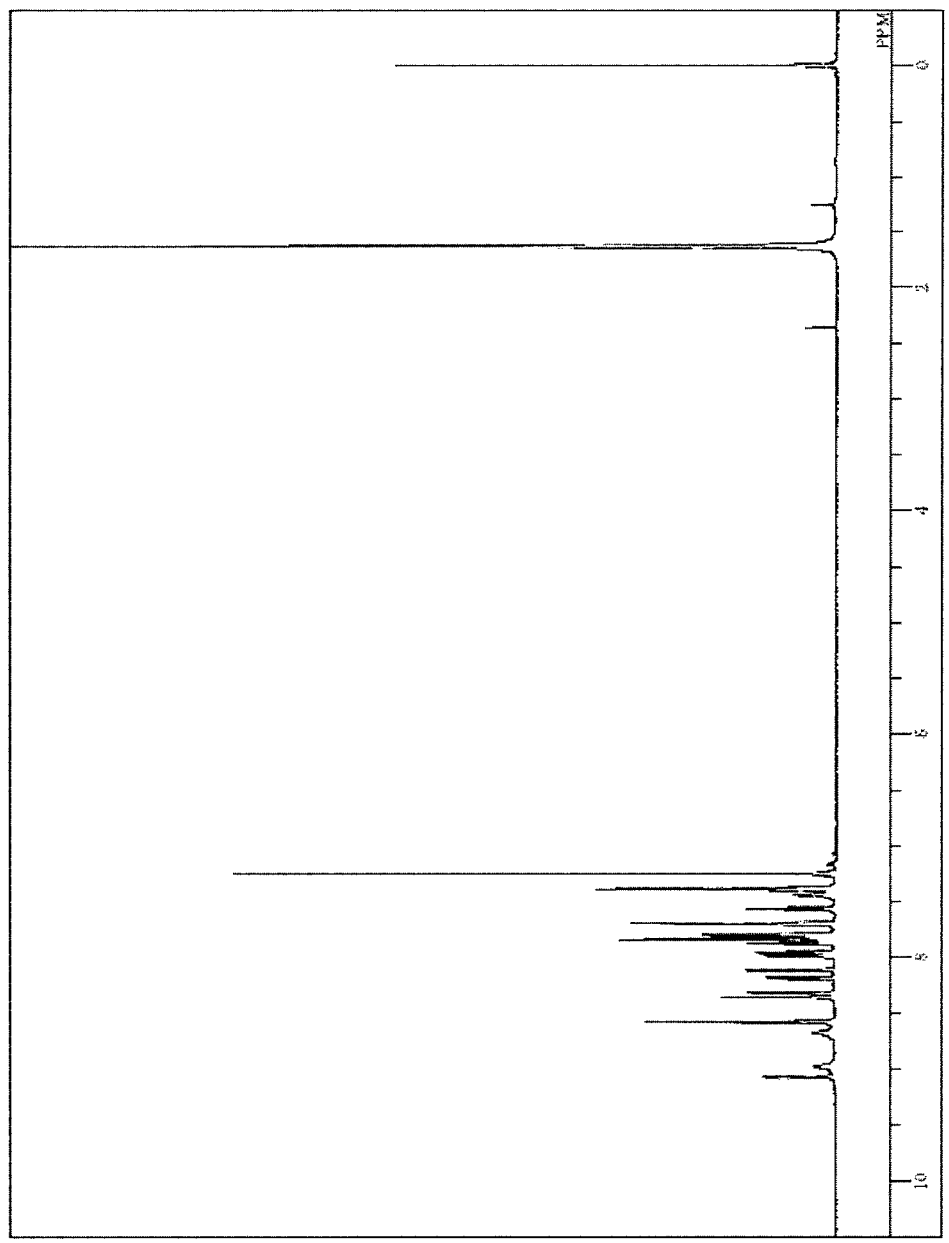
FIG. 20 is a ¹H-NMR chart of a compound (compound 113) of Example 20.

The obtained yellow powder was identified for its structure by the NMR. FIG. 20 shows the results of the ¹H-NMR measurement.

The following 25 signals of hydrogen were detected by the ¹H-NMR (CDCl₃).

δ(ppm) = 9.07 (1H)
8.98 (1H)
8.68 (1H)
8.59 (1H)
8.57 (1H)
8.36 (1H)
8.33 (1H)
8.19 (1H)
8.12 (1H)
8.00 (1H)
7.97 (1H)
7.95 (1H)
7.85 (2H)
7.81 (2H)
7.71 (3H)
7.57 (1H)
7.47 (1H)
7.40 (4H)

Example 21

By using a highly sensitive differential scanning calorimeter (DSC3100S manufactured by Bruker AXS Co.), the compounds of the present invention obtained in the above Examples were measured for their melting points and glass transition points. The results were as follows:

| Example compounds | Melting points | Glass transition points |
|---|---|---|
| Compound 4 | 292° C. | 118° C. |
| Compound 5 | 233° C. | 106° C. |
| Compound 8 | 325° C. | 151° C. |
| Compound 10 | 281° C. | 144° C. |

| Example compounds | Melting points | Glass transition points |
|---|---|---|
| Compound 14 | 312° C. | 148° C. |
| Compound 15 | not measured | 137° C. |
| Compound 30 | 246° C. | 129° C. |
| Compound 46 | 243° C. | 109° C. |
| Compound 106 | 287° C. | 139° C. |
| Compound 108 | 303° C. | 150° C. |
| Compound 26 | 322° C. | 132° C. |
| Compound 66 | 157° C. | 133° C. |
| Compound 62 | 263° C. | 109° C. |
| Compound 54 | 180° C. | 147° C. |
| Compound 110 | 203° C. | 144° C. |
| Compound 112 | 188° C. | 160° C. |
| Compound 18 | 256° C. | 145° C. |
| Compound 82 | 359° C. | 148° C. |
| Compound 111 | 197° C. | 138° C. |
| Compound 113 | 319° C. | 148° C. |

As will be understood from the above results, the compounds of the present invention have glass transition points which are not lower than 100° C. indicating that the thin films formed by using the compounds of the invention maintain stability (remain stable).

Example 22

By using the compounds of the invention obtained in the above Examples, films were vapor-deposited in a thickness of 100 nm on an ITO substrate and were measured for their work functions in the atmosphere by using a photoelectron spectroscope (Model AC-3 manufactured by Riken Keiki Co.). The results were as follows:

| Example compounds | Work functions |
|---|---|
| Compound 30 | 6.35 eV |
| Compound 46 | 6.21 eV |
| Compound 4 | 5.95 eV |

| Example compounds | Work functions |
|---|---|
| Compound 6 | 5.98 eV |
| Compound 8 | 6.03 eV |
| Compound 10 | 6.05 eV |
| Compound 14 | 5.96 eV |
| Compound 15 | 6.03 eV |
| Compound 18 | 6.03 eV |
| Compound 26 | 6.05 eV |
| Compound 54 | 6.25 eV |
| Compound 62 | 6.12 eV |
| Compound 66 | 6.10 eV |
| Compound 82 | 5.95 eV |
| Compound 110 | 6.13 eV |
| Compound 112 | 5.78 eV |

As described above, the compounds of the present invention have values larger than a work function of 5.4 eV possessed by general hole-transporting materials such as NPD, TPD and the like, and have large hole-blocking powers.

Example 23

An organic EL device of a layer structure shown in FIG. 21 was fabricated by vapor-depositing a hole injection layer 3, a hole-transporting layer 4, a luminous layer 5, a hole-blocking layer 6, an electron-transporting layer 7, an electron injection layer 8 and a cathode (aluminum electrode) 9 in this order on a glass substrate 1 on which an ITO electrode has been formed in advance as a transparent anode 2.

Concretely, the glass substrate 1 on which the ITO film has been formed in a thickness of 150 nm was washed with an organic solvent and was, thereafter, washed on its surfaces by an oxygen plasma treatment. Thereafter, the glass substrate with the ITO electrode was placed in a vacuum evaporation machine, and the pressure therein was reduced down to 0.001 Pa or lower.

Next, as the hole injection layer 3, a compound 114 of the following structural formula was vapor-deposited at a deposition rate of 6 nm/min. in a thickness of 20 nm so as to cover the transparent anode 2.

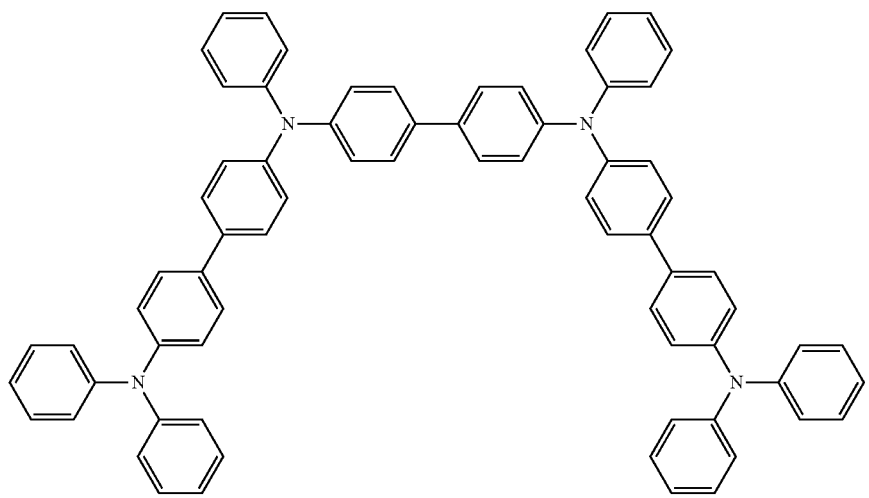

(Compound 114)

On the hole injection layer 3, a compound 115 of the following structural formula was vapor-deposited as the hole-transporting layer 4 at a deposition rate of 6 nm/min. in a thickness of 40 nm.

On the luminous layer 5, the compound 30 of the invention synthesized in Example 7 was vapor-deposited at a deposition rate of 6 nm/min. in a thickness of 30 nm to form the hole-blocking layer/electron-transporting layer 6 and 7.

(Compound 115)

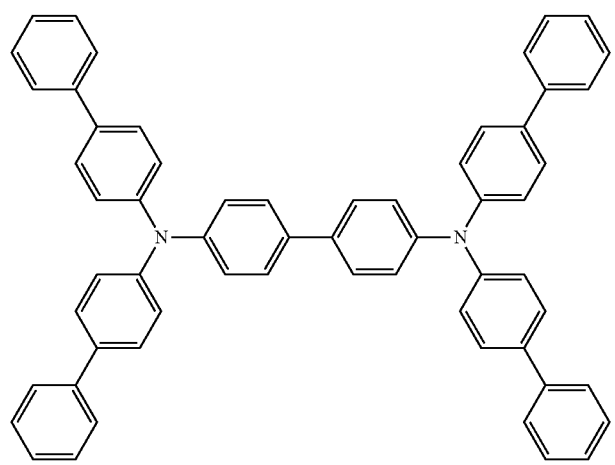

On the hole-transporting layer 4, the luminous layer 5 was formed in a thickness of 30 nm by two-way-depositing a compound 116 of the following structural formula and a compound 117 of the following structural formula at such deposition rates that the ratio of the deposition rates was compound 116:compound 117=5:95.

On the thus formed hole-blocking layer/electron-transporting layer 6 and 7, the electron injection layer 8 was formed in a thickness of 0.5 nm by vapor-depositing lithium fluoride at a deposition rate of 0.6 nm/min.

(Compound 116)

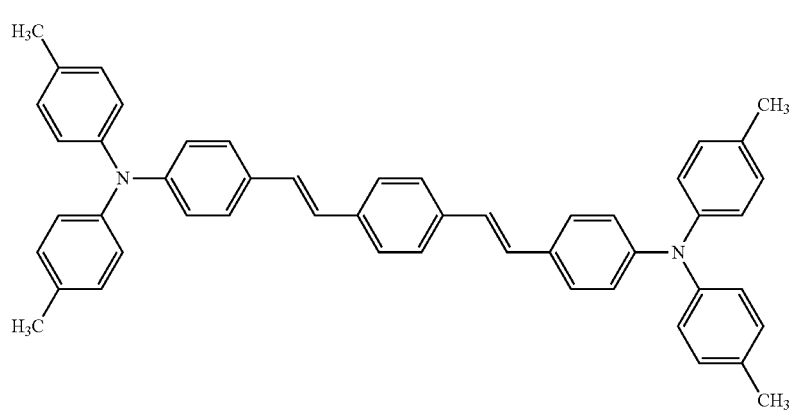

(Compound 117)

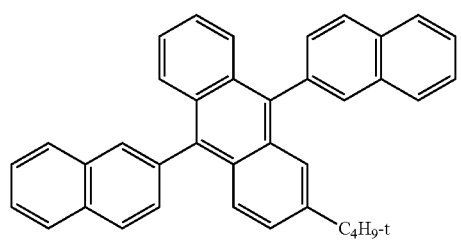

Finally, aluminum was vapor-deposited in a thickness of 150 nm to form the cathode 9. The thus fabricated organic EL device was measured for its properties in the atmosphere at normal temperature.

The organic EL device forming an organic layer (hole-blocking layer/electron-transporting layer) by using the compound 30 of the invention was impressed with a DC voltage to measure the luminous properties which were as shown in Table 1.

Example 24

An organic EL device was fabricated under the same conditions as in Example 23 but using the compound 46 of the invention synthesized in Example 8 as the material for forming the hole-blocking layer/electron-transporting layer 6 and 7. The organic EL device was measured for its properties in the atmosphere at normal temperature. The organic EL device was impressed with a DC voltage to measure the luminous properties which were as shown in Table 1.

Example 25

An organic EL device was fabricated under the same conditions as in Example 23 but using the compound 4 of the invention synthesized in Example 1 as the material for forming the hole-blocking layer/electron-transporting layer 6 and 7. The thus fabricated organic EL device was measured for its properties in the atmosphere at normal temperature. The thus fabricated organic EL device was impressed with a DC voltage to measure the luminous properties which were as shown in Table 1.

Example 26

An organic EL device was fabricated under the same conditions as in Example 23 but using the compound 5 of the invention synthesized in Example 2 as the material for forming the hole-blocking layer/electron-transporting layer 6 and 7. The thus fabricated organic EL device was measured for its properties in the atmosphere at normal temperature. The thus fabricated organic EL device was impressed with a DC voltage to measure the luminous properties which were as shown in Table 1.

Example 27

An organic EL device was fabricated under the same conditions as in Example 23 but using the compound 8 of the invention synthesized in Example 3 as the material for forming the hole-blocking layer/electron-transporting layer 6 and 7. The thus fabricated organic EL device was measured for its properties in the atmosphere at normal temperature. The thus fabricated organic EL device was impressed with a DC voltage to measure the luminous properties which were as shown in Table 1.

Example 28

An organic EL device was fabricated under the same conditions as in Example 23 but using the compound 10 of the invention synthesized in Example 4 as the material for forming the hole-blocking layer/electron-transporting layer 6 and 7. The thus fabricated organic EL device was measured for its properties in the atmosphere at normal temperature. The thus fabricated organic EL device was impressed with a DC voltage to measure the luminous properties which were as shown in Table 1.

Example 29

An organic EL device was fabricated under the same conditions as in Example 23 but using the compound 14 of the invention synthesized in Example 5 as the material for forming the hole-blocking layer/electron-transporting layer 6 and 7. The thus fabricated organic EL device was measured for its properties in the atmosphere at normal temperature. The thus fabricated organic EL device was impressed with a DC voltage to measure the luminous properties which were as shown in Table 1.

Example 30

An organic EL device was fabricated under the same conditions as in Example 23 but using the compound 15 of the invention synthesized in Example 6 as the material for forming the hole-blocking layer/electron-transporting layer 6 and 7. The thus fabricated organic EL device was measured for its properties in the atmosphere at normal temperature. The thus fabricated organic EL device was impressed with a DC voltage to measure the luminous properties which were as shown in Table 1.

Example 31

An organic EL device was fabricated under the same conditions as in Example 23 but using the compound 18 of the invention synthesized in Example 17 as the material for forming the hole-blocking layer/electron-transporting layer 6 and 7. The thus fabricated organic EL device was measured for its properties in the atmosphere at normal temperature. The thus fabricated organic EL device was impressed with a DC voltage to measure the luminous properties which were as shown in Table 1.

Example 32

An organic EL device was fabricated under the same conditions as in Example 23 but using the compound 66 of the invention synthesized in Example 12 as the material for forming the hole-blocking layer/electron-transporting layer 6 and 7. The thus fabricated organic EL device was measured for its properties in the atmosphere at normal temperature. The thus fabricated organic EL device was impressed with a DC voltage to measure the luminous properties which were as shown in Table 1.

Example 33

An organic EL device was fabricated under the same conditions as in Example 23 but using the compound 112 of the invention synthesized in Example 16 as the material for forming the hole-blocking layer/electron-transporting layer 6 and 7. The thus fabricated organic EL device was measured for its properties in the atmosphere at normal temperature. The thus fabricated organic EL device was impressed with a DC voltage to measure the luminous properties which were as shown in Table 1.

Comparative Example 1

For comparison, an organic EL device was fabricated under the same conditions as in Example 23 but using the compound 118 of the following structural formula disclosed in WO2003/060956 as the material for forming the hole-blocking layer/electron-transporting layer 6 and 7.

(Compound 118)

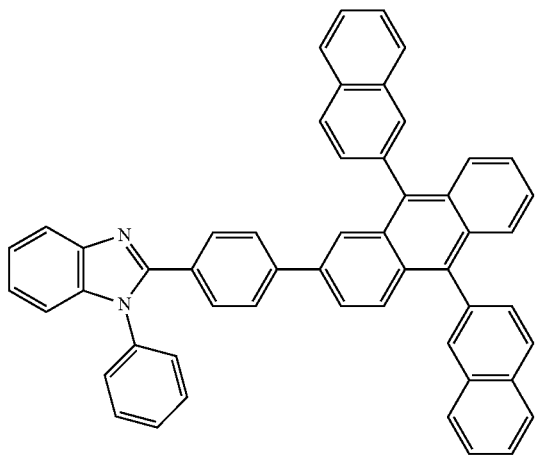

The thus fabricated organic EL device was measured for its properties in the atmosphere at normal temperature. The thus fabricated organic EL device was impressed with a DC voltage to measure the luminous properties which were as shown in Table 1.

TABLE 1

| | Compound | Voltage {V} (@10 mA/cm²) | Brightness [cd/m²] (@10 mA/cm²) | Luminous efficiency [cd/A] (@10 mA/cm²) | Power efficiency [lm/W] (@ 10 mA/cm²) |
|---|---|---|---|---|---|
| Ex. 23 | compound 30 | 4.79 | 893 | 8.91 | 5.86 |
| Ex. 24 | compound 46 | 4.69 | 830 | 8.28 | 5.56 |
| Ex. 25 | compound 4 | 4.57 | 1127 | 11.25 | 7.77 |
| Ex. 26 | compound 6 | 4.11 | 903 | 9.01 | 6.90 |
| Ex. 27 | compound 8 | 4.59 | 1106 | 11.03 | 7.58 |
| Ex. 28 | compound 10 | 4.86 | 933 | 9.31 | 6.03 |
| Ex. 29 | compound 14 | 4.54 | 1137 | 11.35 | 7.87 |
| Ex. 30 | compound 15 | 4.61 | 956 | 9.54 | 6.51 |
| Ex. 31 | compound 18 | 4.29 | 854 | 8.52 | 6.25 |
| Ex. 32 | compound 66 | 4.74 | 1043 | 10.40 | 6.90 |
| Ex. 33 | compound 112 | 4.92 | 819 | 8.19 | 5.23 |
| Comp. Ex. 1 | compound 118 | 5.95 | 792 | 7.92 | 4.19 |

As for the driving voltage at a current density of 10 mA/cm² as shown in Table 1, Examples 23 to 33 of the invention have driving voltages of as low as 4.11 to 4.92 V as compared to 5.95 V of the organic EL device (Comparative Example 1) that uses the compound 118 of the above structural formula. When a current is flown at a density of 10 mA/cm², further, the brightness and luminous efficiency are all improved. Moreover, Examples 23 to 33 all show power efficiencies of from 5.23 to 7.87 lm/W which are great improvements over 4.19 lm/W of Comparative Example 1.

It will, therefore, be learned that the organic EL device of the present invention features excellent luminous efficiency and power efficiency as compared to the device that uses the compound 118 of the above general formula that is a widely employed electron-transporting material, and is capable of achieving a conspicuous decrease in the practical driving voltage.

From a conspicuous decrease in the driving voltage attained by the organic EL device using the benzotriazole derivative of the present invention that has a benzotriazole ring structure and a pyridine structure, it is presumed that the rate of electron migration in the benzotriazole derivative is very larger than that of the compound 118 of the above structural formula that is a widely used electron-transporting material.

INDUSTRIAL APPLICABILITY

The benzotriazole derivative of the present invention has good electron injection property and excellent hole-blocking power, remains stable in its thin film state, and can be used as an excellent compound for fabricating the organic EL devices. Upon fabricating the organic EL devices by using the above compound, further, it is allowed to attain a high luminous efficiency and power efficiency while lowering the practical driving voltage and improving the durability. Its use can, therefore, be expanded to, for example, domestic appliances and illumination equipment.

DESCRIPTION OF SYMBOLS 1 glass substrate
2 transparent anode
3 hole-transporting layer
4 luminous layer
5 hole-blocking layer
6 electron-transporting layer
7 electron injection layer
8 cathode

The invention claimed is:
1. A benzotriazole derivative represented by the following general formula (1),

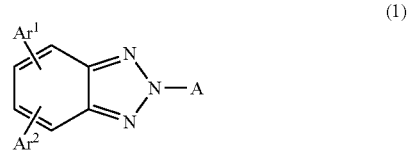

(1)

wherein,
Ar¹ is an aromatic hydrocarbon group or an aromatic heterocyclic group,
Ar² is a hydrogen atom, a deuterium atom, an aromatic hydrocarbon group or an aromatic heterocyclic group, and A is a monovalent group represented by the following formula (2),

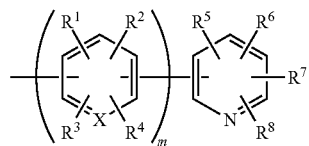
(2)

wherein, m is an integer of 1 or 2,

X is a carbon atom or a nitrogen atom, $R^1$ to $R^8$ are independently selected from hydrogen; deuterium; fluorine; chlorine; cyano; alkyl groups having 1 to 6 carbon atoms; aromatic hydrocarbon groups; or aromatic heterocyclic groups; and wherein when X is a nitrogen atom, none of the groups $R^1$ to $R^4$ are bonded to the nitrogen atom, and any one of $R^1$ to $R^4$ is not present, and when m is 2, a plurality of $R^1$ to $R^4$ and X may be the same or different from each other.

2. A benzotriazole derivative according to claim 1 represented by the following general formula (1-1),

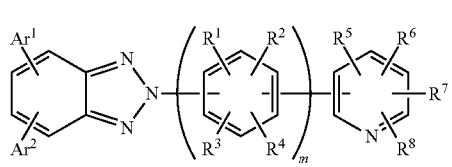
(1-1)

wherein, $Ar^1$, $Ar^2$, $R^1$ to $R^8$ and m are as defined in the above general formula (1).

3. A benzotriazole derivative according to claim 2 represented by the following general formula (1a),

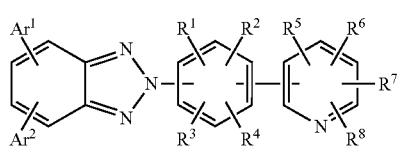
(1a)

wherein, $Ar^1$, $Ar^2$, $R^1$ to $R^8$ and m are as defined in the above general formula (1).

4. A benzotriazole derivative according to claim 3 represented by the following general formula (1a-1),

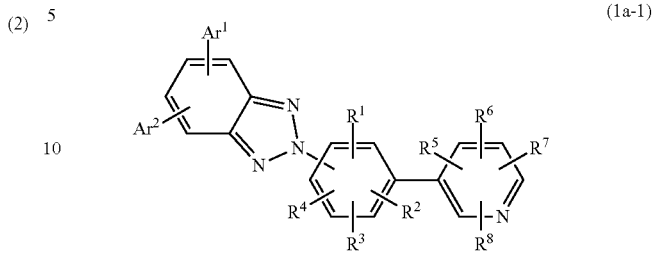
(1a-1)

wherein, $Ar^1$, $Ar^2$, $R^1$ to $R^8$ and m are as defined in the above general formula (1).

5. A benzotriazole derivative according to claim 3 represented by the following general formula (1a-2),

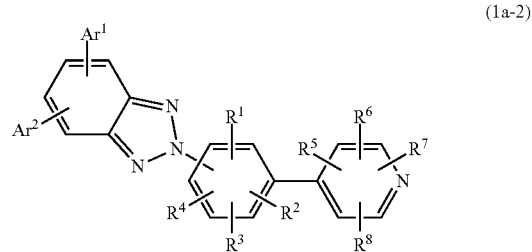
(1a-2)

wherein, $Ar^1$, $Ar^2$, $R^1$ to $R^8$ and m are as defined in the above general formula (1).

6. A benzotriazole derivative according to claim 3 represented by the following general formula (1a-3),

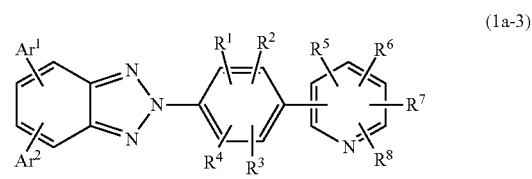
(1a-3)

wherein, $Ar^1$, $Ar^2$, $R^1$ to $R^8$ and m are as defined in the above general formula (1).

7. A benzotriazole derivative according to claim 3 represented by the following general formula (1a-4),

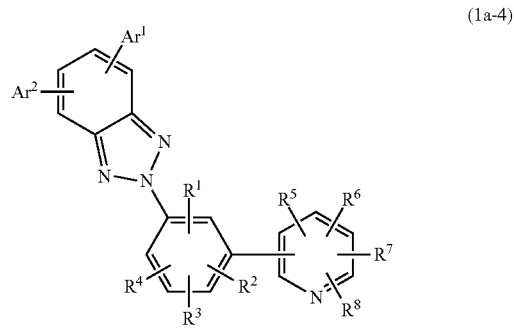
(1a-4)

wherein,

Ar$^1$, Ar$^2$, R$^1$ to R$^8$ and m are as defined in the above general formula (1).

8. An organic electroluminescent device having a pair of electrodes and at least one organic layer interposed therebetween, wherein at least one of the organic layers contains the benzotriazole derivative of claim 1.

9. The organic electroluminescent device according to claim 8, wherein the organic layer containing the benzotriazole derivative is an electron-transporting layer.

10. The organic electroluminescent device according to claim 8, wherein the organic layer containing the benzotriazole derivative is a hole-blocking layer.

11. The organic electroluminescent device according to claim 8, wherein the organic layer containing the benzotriazole derivative is a luminous layer, and the compound represented by the general formula (1) forms the luminous layer.

12. The organic electroluminescent device according to claim 8, wherein the organic layer containing the benzotriazole derivative is an electron injection layer.

* * * * *